US009924719B2

(12) United States Patent
Tanabe et al.

(10) Patent No.: US 9,924,719 B2
(45) Date of Patent: Mar. 27, 2018

(54) PYRIDAZINE COMPOUND

(71) Applicant: Sumitomo Chemical Company, Limited, Tokyo (JP)

(72) Inventors: Takamasa Tanabe, Takarazuka (JP); Yoshihiko Nokura, Takarazuka (JP); Ryota Maehata, Takarazuka (JP); Kohei Orimoto, Takarazuka (JP); Yuji Nakajima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/515,879

(22) PCT Filed: Sep. 29, 2015

(86) PCT No.: PCT/JP2015/077420
§ 371 (c)(1),
(2) Date: Mar. 30, 2017

(87) PCT Pub. No.: WO2016/052455
PCT Pub. Date: Apr. 7, 2016

(65) Prior Publication Data
US 2017/0295787 A1 Oct. 19, 2017

(30) Foreign Application Priority Data
Oct. 3, 2014 (JP) .................. 2014-204515

(51) Int. Cl.
C07D 237/14 (2006.01)
A01N 43/58 (2006.01)
C07D 401/04 (2006.01)

(52) U.S. Cl.
CPC ........... *A01N 43/58* (2013.01); *C07D 237/14* (2013.01); *C07D 401/04* (2013.01)

(58) Field of Classification Search
CPC ...................................................... A01N 43/58
See application file for complete search history.

(56) References Cited

FOREIGN PATENT DOCUMENTS

| JP | S591469 A | 1/1984 |
| JP | H1192456 A | 4/1999 |
| JP | 200139954 | 2/2001 |
| JP | 2003313169 A | 11/2003 |
| JP | 201360420 A | 4/2013 |
| WO | 2013027660 A1 | 2/2013 |

OTHER PUBLICATIONS

Vippagunta et al. (2001).*
Int'l Preliminary Report on Patentability dated Apr. 4, 2017 in Int'l Application No. PCT/JP2015/077420.
Int'l Search Report dated Dec. 22, 2015 in Int'l Application No. PCT/JP2015/077420.
STN International, Benzenesulfonamide, N-(1,1-dimethylethyl)-2-[6-(1-methylethoxy)-3-pyridazinyl]-, File Registry [online], entered STN: Jun 6, 2014, [retrieved on Dec. 9, 2015], CAS Registry No. 1609752-12-6.

* cited by examiner

*Primary Examiner* — Paul V Ward
(74) *Attorney, Agent, or Firm* — Panitch Schwarze Belisario & Nadel LLP

(57) ABSTRACT

A pyridazine compound represented by formula (1):

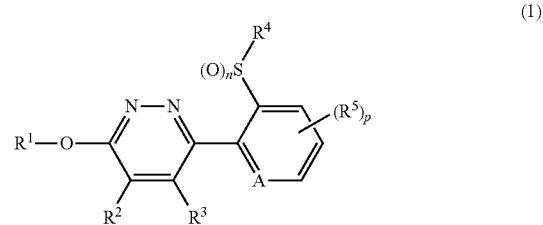

(1)

wherein A represents a nitrogen atom or a $CR^6$, $R^1$ represents a C2-C10 alkyl group having one or more halogen atoms, etc., $R^2$ and $R^3$ represent independently of each other a hydrogen atom, etc., $R^4$ represents a C1-C6 chain hydrocarbon group optionally having one or more halogen atoms, $R^5$ represents a C1-C6 chain hydrocarbon group optionally having one or more halogen atoms, etc., $R^6$ represents a hydrogen atom, etc., n represents 0, 1, or 2, and p represents 0, 1, or 2, has an excellent efficacy for controlling harmful arthropods.

13 Claims, No Drawings

PYRIDAZINE COMPOUND

CROSS-REFERENCE TO RELATED APPLICATION

This application is a Section 371 of International Application No. PCT/JP2015/077420, filed Sep. 29, 2015, which was published in the Japanese language on Apr. 7, 2016, under International Publication No. WO 2016/052455 A1, and the disclosure of which is incorporated herein by reference.

TECHNICAL FIELD

The present invention relates to a certain class of pyridazine compound and use of said compound for controlling harmful arthropods.

BACKGROUND ART

To date, some compounds for controlling harmful arthropods have been developed and come into practical use.

Also, a certain class of heterocyclic compound has been known (see Patent Document 1).

CITATION LIST

Patent Document

Patent Document 1: JP 2003-313169 A

SUMMARY OF THE INVENTION

Problems to be Solved By Invention

An object of the present invention is to provide a compound having an excellent efficacy for controlling harmful arthropods and a method for controlling harmful arthropods using said compound.

Means to Solve Problems

[1] A piridazine compound represented by formula (1):

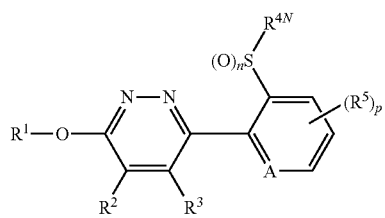

wherein,

A represents a nitrogen atom or a $CR^6$;

$R^1$ represents a C2-C10 alkyl group, a C3-C10 alkenyl group, a C3-C10 alkynyl group, a (C1-C5 alkyl)-O—(C2-C5 alkyl) group, a (C3-C5 alkenyl)-O—(C2-C5 alkyl) group, a (C3-C5 alkynyl)-O—(C2-C5 alkyl) group, a (C1-C5 alkyl)-S(O)$_m$—(C2-C5 alkyl) group, a (C3-C5 alkenyl)-S(O)$_m$—(C2-C5 alkyl) group, a (C3-C5 alkynyl)-S(O)$_m$—(C2-C5 alkyl) group, or a (C1-C5 alkyl)-C(O)—(C1-C5 alkyl) group (wherein $R^1$ has one or more halogen atoms);

$R^2$ and $R^3$ represent independently of each other a hydrogen atom, a C1-C6 alkyl group optionally having one or more halogen atoms, a C2-C6 alkoxycarbonyl group, a cyano group, or a halogen atom;

$R^4$ represents a C1-C6 chain hydrocarbon group optionally having one or more halogen atoms;

$R^5$ represents a C1-C6 chain hydrocarbon group optionally having one or more halogen atoms, a phenyl group optionally having one or more atoms or groups selected from Group A, a 5-membered aromatic heterocyclic group selected from Group B (wherein said 5-membered aromatic heterocyclic group may optionally have one or more atoms or groups selected from Group A), a 6-membered aromatic heterocyclic group selected from Group C (wherein said 6-membered aromatic heterocyclic group may optionally have one or more atoms or groups selected from Group A), a 3 to 7 membered nonaromatic heterocyclic group selected from Group D (wherein the 3 to 7 membered nonaromatic heterocyclic group may optionally have one or more atoms or groups selected from the group consisting of a halogen atom and a C1-C6 alkyl group), a $OR^7$, a $NR^8R^9$, a $NR^8C(O)R^{10}$, a $NR^8C(O)OR^{11}$, a $NR^8C(O)NR^{12}R^{13}$, a $N=CHNR^{12}R^{13}$, a $N=S(O)_xR^{12}R^{13}$, a $S(O)_yR^{12}$, a $C(O)OR^8$, a cyano group, or a halogen atom;

$R^6$ represents a hydrogen atom, or a halogen atom;

$R^7$ represents a hydrogen atom, a C1-C6 alkyl group, a C3-C6 alkenyl group, a C3-C6 alkynyl group, a (C1-C3 alkyl)-O—(C1-C3 alkyl) group, a (C1-C3 alkyl)-S(O)$_y$—(C1-C3 alkyl) group, a C3-C7 cycloalkyl group, a (C3-C7 cycloalkyl)-(C1-C3 alkyl) group (wherein said C1-C6 alkyl group, said C3-C6 alkenyl group, said C3-C6 alkynyl group, said (C1-C3 alkyl)-O—(C1-C3 alkyl) group, said (C1-C3 alkyl)-S(O)$_y$—(C1-C3 alkyl) group, said C3-C7 cycloalkyl group, and said (C3-C7 cycloalkyl)-(C1-C3 alkyl) group may optionally have one or more halogen atoms), or a phenyl C1-C3 alkyl group (wherein the phenyl moiety in saide phenyl C1-C3 alkyl group may optionally have one or more atoms or groups selected from Group A);

$R^8$ represents a hydrogen atom, a C1-C6 alkyl group optionally having one or more halogen atoms, a C3-C6 alkenyl group optionally having one or more halogen atoms, or a C3-C6 alkynyl group optionally having one or more halogen atoms;

$R^9$ represents a hydrogen atom, a C1-C6 alkyl group, a C3-C6 alkenyl group, a C3-C6 alkynyl group, a (C1-C3 alkyl)-O—(C1-C3 alkyl) group, a (C1-C3 alkyl)-S(O)$_y$—(C1-C3 alkyl) group, a C3-C7 cycloalkyl group, a (C3-C7 cycloalkyl)-(C1-C3 alkyl) group (wherein said C1-C6 alkyl group, said C3-C6 alkenyl group, said C3-C6 alkynyl group, said (C1-C3 alkyl)-O—(C1-C3 alkyl) group, said (C1-C3 alkyl)-S(O)$_y$—(C1-C3 alkyl) group, said C3-C7 cycloalkyl group, and said (C3-C7 cycloalkyl)-(C1-C3 alkyl) group may optionally have one or more halogen atoms), a cyano C1-C6 alkyl group, a phenyl C1-C3 alkyl group (wherein the phenyl moiety in said phenyl C1-C3 alkyl group may optionally have one or more atoms or groups selected from Group A), or a (5 or 6 membered heteroaryl)C1-C3 alkyl group (wherein the 5 or 6 membered heteroaryl moiety in said (5 or 6 membered heteroaryl)C1-C3 alkyl group may optionally have one or more atoms or groups selected from Group A);

$R^{10}$ represents a hydrogen atom, a C1-C6 alkyl group, a C3-C6 alkenyl group, a C3-C6 alkynyl group, a C3-C7 cycloalkyl group, a (C3-C7 cycloalkyl)-(C1-C3 alkyl) group (wherein said C1-C6 alkyl group, said C3-C6 alkenyl group, said C3-C6 alkynyl group, said C3-C7 cycloalkyl group, and said (C3-C7 cycloalkyl)-(C1-C3 alkyl) group may optionally have one or more halogen atoms), or a phenyl C1-C3 alkyl group (wherein the phenyl moiety in said phenyl C1-C3 alkyl group may optionally have one or more atoms or substituents selected from Group A);

$R^{11}$ represents a C1-C6 alkyl group optionally having one or more halogen atoms, a C3-C6 alkenyl group optionally having one or more halogen atoms, a C3-C6 alkynyl group optionally having one or more halogen atoms, a C3-C7 cycloalkyl group optionally having one or more halogen atoms, a (C3-C7 cycloalkyl)-(C1-C3 alkyl) group optionally having one or more halogen atoms (wherein said (C3-C7 cycloalkyl)-(C1-C3 alkyl) group may optionally have one or more halogen atoms), or a phenyl C1-C3 alkyl group (wherein the phenyl moiety in said phenyl C1-C3 alkyl group may optionally have one or more atoms or groups selected from Group A);

$R^{12}$ and $R^{13}$ represent independently of each other a C1-C6 alkyl group optionally having one or more halogen atoms;

$R^{14}$ represents a hydrogen atom, a C1-C6 alkyl group optionally having one or more halogen atoms, a C2-C6 alkylcarbonyl group optionally having one or more halogen atoms, or a C2-C6 alkoxycarbonyl group optionally having one or more halogen atoms;

n represents 0, 1, or 2;

m represents 0, 1, or 2;

p represents 0, 1, 2, or 3 (wherein when p represents 2 or 3, a plurality of $R^5$ may be identical or different);

x represents 0 or 1;

y represents 0, 1, or 2;

Group A: a group consisting of a C1-C6 alkyl group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a cyano group, and a halogen atom;

Group B:

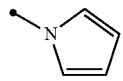
B-1

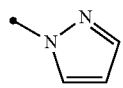
B-2

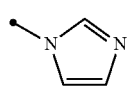
B-3

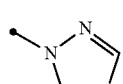
B-4

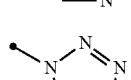
B-5

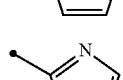
B-6

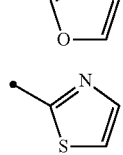
B-7

-continued

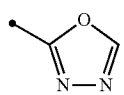
B-8

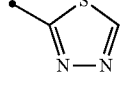
B-9

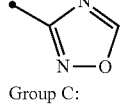
B-10

Group C:

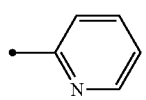
C-1

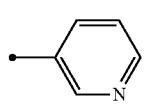
C-2

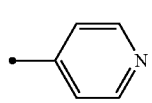
C-3

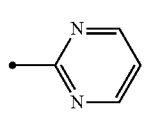
C-4

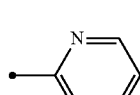
C-5

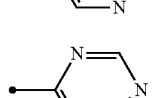
C-6

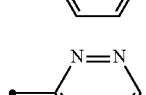
C-7

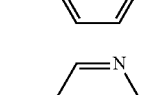
C-8

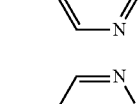
C-9

Group D:

D-1

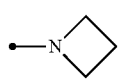
D-2

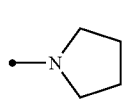
D-3

-continued

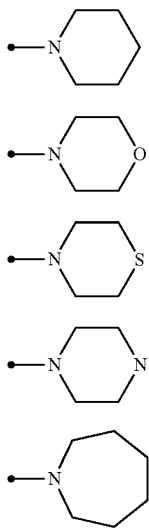

D-4

D-5

D-6

D-7

D-7

(hereinafter, a pyridazine compound represented by formula (1) is refered to as "the compound of the present invention").

[2] The compound according to [1], wherein A represents $CR^6$.

[3] The compound according to [1], wherein A represents a nitrogen atom.

[4] The compound according to any one of [1] to [3], wherein $R^4$ represents a C1-C6 alkyl group optionally having one or more halogen atoms.

[5] The compound according to any one of [1] to [3], wherein $R^4$ represents an ethyl group.

[6] The compound according to any one of [1] to [3], wherein $R^1$ represents a C2-C10 haloalkyl group;

$R^2$ and $R^3$ represent independently of each other a hydrogen atom, a C1-C3 alkyl group optionally having one or more halogen atoms, or a halogen atom;

$R^4$ represents a C1-C6 alkyl group optionally having one or more halogen atoms;

$R^5$ represents a C1-C6 alkyl group optionally having one or more halogen atoms; and p represents 0 or 1.

[7] The compound according to any one of [1] to [3], wherein $R^1$ represents a C2-C10 haloalkyl group;

$R^2$ and $R^3$ represent each a hydrogen atom;

$R^4$ represents a C1-C6 alkyl group optionally having one or more halogen atoms;

$R^5$ represents a C1-C6 alkyl group optionally having one or more halogen atoms; and p represents 0 or 1.

[8] The compound according to any one of [1] to [3], wherein $R^1$ represents a C3-C6 alkyl having four or more fluorine atoms;

$R^2$ and $R^3$ represent each a hydrogen atom;

$R^4$ represents an ethyl group;

$R^5$ represents a C1-C6 alkyl group optionally having one or more halogen atoms; and p represents 0 or 1.

[9] An N-oxide compound represented by formula (1-N):

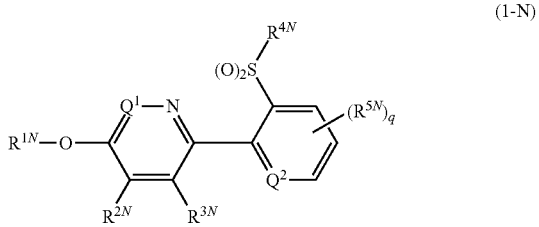

(1-N)

wherein $Q^1$ represents a $N^+$—$O^-$ or a nitrogen atom, $Q^2$ represents a $N^+$—$O^-$, a $CR^{6N}$, or a nitrogen atom, wherein at least one of $Q^1$ and $Q^2$ represents an $N^+$—$O^-$;

$R^{6N}$ represents a hydrogen atom, or a halogen atom;

$R^{1N}$ represents a C2-C10 haloalkyl group;

$R^{2N}$ and $R^{3N}$ represent independently of each other a hydrogen atom, a C1-C3 alkyl group optionally having one or more halogen atoms, or a halogen group;

$R^{4N}$ represents a C1-C6 alkyl group optionally having one or more halogen atoms;

$R^{5N}$ represents a C1-C6 alkyl group optionally having one or more halogen atoms; and q represents 0 or 1

(hereinafter, refered to as "N-oxide compound").

[10] A composition for controlling a harmful arthropod, comprising the compound according to any one of [1] to [9], and an inert carrier.

[11] A method for controlling a harmful arthropod, comprising applying an effective amount of the compound according to any one of [1] to [9] to a harmful arthropod or a habitat where a harmful arthropod lives.

Effect of Invention

The present compound has an excellent control efficacy against harmful arthropods and is thus useful as an active ingredient of an agent for controlling harmful arthropods.

MODE FOR CARRYING OUT THE INVENTION

The group(s) as described herein is/are explained as follows by means of examples.

The expression of "optionally having one or more atoms or groups selected from Group A" as used herein represents that when two or more atoms or groups selected from Group A are present, these atoms or groups selected from Group A may be identical to or different from each other.

The expression of "optionally having one or more halogen atoms" as used herein represents that when two or more halogen atoms are present, these halogen atoms may be identical to or different from each other.

The expression of "having one or more halogen atoms" as used herein represents that when two or more halogen atoms are present, the halogen atoms may be identical to or different from each other.

The term of "heterocyclic group" as used herein represents a group containing one or more atoms selected from the group consisting of a nitrogen atom, an oxygen atom, and a sulfur atom as a ring constituent atom other than a carbon atom, and includes an aromatic heterocyclic group and a non-aromatic heterocyclic group.

Examples of the term of "aromatic heterocyclic group" as used herein include, a 5-membered aromatic heterocyclic group such as 2-furyl group, 3-furyl group, 2-thienyl group, 3-thienyl group, 3-pyrazolyl group, 4-pyrazolyl group, 5-pyrazolyl group, 1-pyrrolyl group, 1-pyrazolyl group, 1-imidazolyl group and 1,2,4-triazol-1-yl group; and a 6-membered aromatic heterocyclic group in which a carbon atom of the heterocyclic group is attached to the rest of the molecule, such as 2-pyridyl group, 3-pyridyl group, and 4-pyridyl group.

Examples of the term of "non-aromatic heterocyclic group" as used herein include aziridin-1-yl group, azetidin-1-yl group, pyrrolidin-1-yl group, 3,3,4,4-tetrafluoropyrrolidin-1-yl group, tetrahydrofuran-2-yl group, tetrahydrofuran-3-yl group, piperidin-1-yl group, morpholin-4-yl group, thiomorpholin-4-yl group, and azepan-1-yl group.

The term of "5 or 6 membered heteroaryl" as used herein represents a 5-membered aromatic heterocyclic group or a 6-membered aromatic heterocyclic group.

Examples of the term of "C2-C10 alkyl group" as used herein include ethyl group, isopropyl group, propyl group, and butyl group.

Examples of the "C2-C10 haloalkyl group" as used herein include 2-fluoroethyl group, 2,2-difluoroethyl group, 2,2,2-trifluoroethyl group, 2,2,2-trichloroethyl group, pentafluoroethyl group, heptafluoroisopropyl group, 2,2,3,3-tetrafluoropropyl group, 2,2,3,3,3-pentafluoropropyl group, and 2,2,3,4,4,4-hexafluoroburyl group.

Examples of the term of "C3-C10 alkenyl group" as used herein include 2-propenyl group, and 3-butenyl group.

Examples of the term of "C3-C10 haloalkenyl group" as used herein include 3,3-difluoro-2-propenyl group, 3,3-difluoro-2-propenyl group, and 4,4-difluoro-3-butenyl group.

Examples of the term of "C3-C10 alkynyl group" as used herein include 2-propynyl group, and 2-butynyl group.

Examples of the term of "C3-C10 haloalkynyl group" as used herein include 3-chloro-2-propynyl group, 3-fluoro-2-propynyl group, and 4,4,4-trifluoro-2-butynyl group.

The term of "(C1-C5 alkyl)-O—(C2-C5 alkyl) group having one or more halogen atoms" as used herein represents a group having one or more halogen atoms in the C1-C5 alkyl moiety and/or C2-C5 alkyl moiety, and includes, for example, 2-(2,2,2-trifluoroethoxy)ethyl group, and 1,1,1-trifluoro-3-methoxypropan-2-yl group.

Examples of the term of "(C1-C5 alkyl)-O—(C2-C5 alkyl) group" as used herein includes 2-methoxyethyl group and 2-ethoxyethyl group.

The term of "(C3-C5 alkenyl)-O—(C2-C5 alkyl) group having one or more halogen atoms" as used herein represents a group having one or more halogen atoms in the C3-C5 alkenyl moiety and/or C2-C5 alkyl moiety, and includes, for example, 2-(3,3-difluoro-2-propenyloxy)ethyl group.

The term of "(C3-C5 alkenyl)-O—(C2-C5 alkyl) group" as used herein includes, for example, 2-(2-propenyl)oxyethyl group.

The term of "(C3-C5 alkynyl)-O—(C2-C5 alkyl) group having one or more halogen atoms" as used herein represents a group having one or more halogen atoms in the C3-C5 alkynyl moiety and/or C2-C5 alkyl moiety, and includes, for example, 2-(4,4,4-trifluoro-2-butynyloxy)ethyl group.

The term of "(C3-C5 alkynyl)-O—(C2-C5 alkyl) group" as used herein includes, for example, 2-(2-butyloxy)ethyl group.

The term of "(C1-C5 alkyl)-S(O)$_m$—(C2-C5 alkyl) group having one or more halogen atoms" as used herein represents a group having one or more halogen atoms in the C1-C5 alkyl moiety and/or C2-C5 alkyl moiety, and includes, for example, 2-(trifluoromethylthio)ethyl group, 2-(trifluoromethylsulfinyl) ethyl group, 2-(trifluoromethylsulfonyl)ethyl group, 2-(2,2,2-trifluoroethylthio)ethyl group, 2-(2,2,2-trifluoroethanesulfinyl)ethyl group, and 2-(2,2,2-trifluoroethanesulfonyl) ethyl group.

The term of "(C1-C5 alkyl)-S(O)$_m$—(C2-C5 alkyl) group" as used herein includes, for example, 2-(methylthio)ethyl group, and 2-(methylsulfonyl)ethyl group.

The term of "(C1-C3 alkyl)-S(O)$_y$—(C1-C3 alkyl) group optionally having one or more halogen atoms" as used herein represents a group having one or more halogen atoms in the C1-C3 alkyl moiety and/or C1-C3 alkyl moiety, and includes, for example, methylthiomethyl group, trifluoromethylthiomethyl group, methanesulfinylmethyl group, trifluoromethanesulfonylmethyl group, methanesulfonylmethyl group, 2-(methylthio)ethyl group, and ethylthiomethyl group.

The term of "(C1-C3 alkyl)-S(O)$_y$—(C1-C3 alkyl) group" as used herein includes, for example, methylthiomethyl group, methanesulfinylmethyl group, methanesulfonylmethyl group, 2-(methylthio)ethyl group, and ethylthiomethyl group.

The term of "(C3-C5 alkenyl)-S(O)$_m$—(C2-C5 alkyl) group having one or more halogen atoms" as used herein represents a group having one or more halogen atoms in the C3-C5 alkenyl moiety and/or C2-C5 alkyl moiety, and includes, for example, 2-(3,3-difluoro-2-propenylthio)ethyl group.

The term of "(C3-C5 alkenyl)-S(O)$_m$—(C2-C5 alkyl) group" as used herein includes, for example, 2-(2-propenylthio) ethyl group.

The term of "(C3-C5 alkynyl)-S(O)$_m$—(C2-C5 alkyl) group having one or more halogen atoms" as used herein represents a group having one or more halogen atoms in the C3-C5 alkynyl moiety and/or C2-C5 alkyl moiety, and includes, for example, 2-(4,4,4-trifluoro-2-butynylthio)ethyl group.

The term of "(C3-C5 alkynyl)-S(O)$_m$—(C2-C5 alkyl) group" as used herein includes, for example, 2-(2-butynylthio) ethyl group.

The term of "(C1-C5 alkyl)-C(O)—(C1-C5 alkyl) group having one or more halogen atoms" as used herein represents a group having one or more halogen atoms in either one of the C1-05 alkyl moieties or both of the C1-C5 alkyl moieties, and includes, for example, (3,3,3-trifluoro-2-oxopropyl group.

The term of "(C1-05 alkyl)-C(O)—(C1-C5 alkyl) group" as used herein includes, for example, 2-oxopropyl group, and 3,3-dimethyl-2-oxobutyl group.

Examples of the term of "C1-C6 chain hydrocarbon group optionally having one or more halogen atoms" as used herein include a C1-C6 alkyl group optionally having one or more halogen atoms such as methyl group, ethyl group, propyl group, isopropyl group, butyl group, isobutyl group, sec-butyl group, tert-butyl group, pentyl group, neopentyl group, hexyl group, trifluoromethyl group, tr±chloromethyl group, 2-fluoroethyl group, 2,2-difluoroethyl group, 2,2,2-trifluoroethyl group and pentafluoroethyl group;

a C2-C6 alkenyl group optionally having one or more halogen atoms such as vinyl group, 1-propenyl group, 2-propenyl group, 1-methylvinyl group, 2-methyl-1-propenyl group, 1-butenyl group, 2-butenyl group, 3-butenyl group, 1-pentenyl group, 1-hexenyl group, 1,1-difluoroallyl group and pentafluoroallyl group; and a C2-C6 alkynyl group optionally having one or more halogen atoms such as ethynyl group, propargyl group, 2-butynyl group, 3-butynyl group, 1-pentynyl group, 1-hexynyl group and 4,4,4-trifluoro-2-butynyl group.

Examples of the "phenyl group optionally having one or more atoms or groups selected from Group A" as used herein include phenyl group, 2-fluorophenyl group, 4-fluorophenyl group, 2,3-difluorophenyl group, 2,3,4,5,6-pentafluorophenyl group, 4-chlorophenyl group, 4-bromophenyl group, 4-iodophenyl group, 4-(trifluoromethyl)phenyl group, 4-(trifluoromethoxy)phenyl group, 4-(trifluoromethylsulfanyl) phenyl group, 4-cyanophenyl group, 4-(methylsulfinyl)phenyl group, and 4-(methylsulfonyl) phenyl group.

Examples of the "5-membered aromatic heterocyclic group selected from Group B (wherein said 5-membered aromatic heterocyclic group may optionally have one or more atoms or groups selected from Group A)" as used herein include pyrrol-1-yl group, 2-chloropyrrol-1-yl group, pyrazol-1-yl group, 3-(trifluoromethyl)pyrazol-1-yl group, 4-chloroimidazol-1-yl group, 1,2,4-triazol-1-yl group, 3-methoxy-1,2,4-triazol-1-yl group, 3-methylthio-1,2,4-triazol-1-yl group, 1,2,3-triazol-1-yl group, oxazol-2-yl group, thiazol-2-yl group, 1,3,4-oxadiazol-2-yl group, 1,3,4-thiadiazol-2-yl group, and 1,2,4-oxadiazol-3-yl group.

Examples of the "6-membered aromatic heterocyclic group selected from Group C (wherein said 6-membered aromatic heterocyclic group may optionally have one or more atoms or groups selected from Group A)" as used herein include pyridin-2-yl group, pyridin-3-yl group, pyridin-4-yl group, 4-trifluoromethylpyridin-2-yl group, 2-chloropyridin-5-yl group, pyrimidin-2-yl group, pyrazin-2-yl group, pyrimidin-4-yl group, pyridazin-3-yl group, pyrimidin-5-yl group, and pyridazin-4-yl group.

Examples of the term of "3 to 7 membered nonaromatic heterocyclic group selected from Group D (wherein said 3 to 7 membered nonaromatic heterocyclic group optionally has one or more atoms or groups selected from the group consisting of a halogen atom and a C1-C6 alkyl group)" as used herein include, for example, aziridin-1-yl group, azetidin-1-yl group, pyrrolidin-1-yl group, 3,3,4,4-tetrafluoropyrrolidin-1-yl group, piperidin-1-yl group, 4,4-dimethylpiperidin-1-yl group, and azepan-1-yl group.

Examples of the term of "C3-C7 cycloalkyl group optionally having one or more halogen atoms" as used herein include cyclopropyl group, 2,2-difluorocyclopropan-1-yl group, cyclobutanyl group, cyclopentanyl group, cyclohexyl group, and cycloheptanyl group.

Examples of the term of "C3-C7 cycloalkyl group" as used herein include cyclopropyl group, cyclopentanyl group, cyclohexyl group, and cycloheptanyl group.

The term of "(C3-C7 cycloalkyl)-(C1-C3 alkyl) group (wherein the (C3-C7 cycloalkyl)-(C1-C3 alkyl) group may optionally have one or more halogen atoms" as used herein represents a group having one or more halogen atoms in the C3-C7 cycloalkyl moiety, and includes, for example, cyclopropylmethyl group, 2-(cyclopropyl)ethyl group, (2,2-difluorocyclopropyl)methyl group, and cyclopentylmethyl group.

Examples of the "(C3-C7 cycloalkyl)-(C1-C3 alkyl) group" as used herein include cyclopropylmethyl group, 2-(cyclopropyl)ethyl group, and cyclopenthylmethyl group.

Examples of the term of "phenyl C1-C3 alkyl group (wherein the phenyl moiety in said phenyl C1-C3 alkyl group may optionally have one or more atoms or groups selected from Group A)" include benzyl group, 2-fluorobenzyl group, 4-chlorobenzyl group, 4-(trifluoromethyl)benzyl group, and 2-[4-(trifluoromethyl)phenyl]ethyl group.

Examples of the term of "(5 or 6 membered heteroaryl) C1-C3 alkyl group (wherein the 5 or 6 membered heteroaryl moiety in said (5 or 6 membered heteroaryl)C1-C3 alkyl group may optionally have one or more atoms or groups selected from Group A)" as used herein include, for example, a C1-C3 alkyl group having one 5-membered aromatic heterocyclic group such as (1-methylpyrrol-3-yl)methyl group, (oxazol-2-yl)methyl group, (tetrahydrofuran-3-yl)methyl group, (tetrahydrofuran-2-yl)methyl group, 2-(1,2,4-triazol-1-yl)ethyl group and (2-chlorothiazol-5-yl) methyl group; and a C1-C3 alkyl group having one 6-membered aromatic heterocyclic group such as (pyridin-2-yl)methyl group, (pyridin-4-yl)methyl group, (pyrimidin-2-yl)methyl group, (pyrimidin-4-yl)methyl group, 2-(2-chloropyridin-5-yl) ethyl group and [2-(trifluoromethyl)pyridin-2-yl]methyl group.

Examples of the term of "C2-C6 alkoxycarbonyl group" as used herein include methoxycarbonyl group, and ethoxycarbonyl group.

The term of "(C1-C3 alkyl)-O—(C1-C3 alkyl) group optionally having one or more halogen atoms" as used herein represents a group having one or more halogen atoms in either one of the C1-C3 alkyl moieties or both of the C1-C3 alkyl moieties, and includes, for example, methoxymethyl group, ethoxymethyl group, and 2-(methoxy)ethyl group.

Examples of the term of "C1-C6 alkoxyl group optionally having one or more halogens" as used herein include trifluoromethoxy group, and 2,2,2-trifluoroethoxy group.

The term of "halogen atom" as used herein represents fluorine atom, chlorine atom, bromine atom, and iodine atom.

Examples of the compound of the present invention include the following compounds.

A compound represented by formula (1), wherein $R^4$ represents a C1-C6 alkyl group or a C1-C6 haloalkyl group;

A compound represented by formula (1), wherein $R^4$ represents a C1-C6 alkyl group;

A compound represented by formula (1), wherein $R^4$ represents a C1-C6 haloalkyl group;

A compound represented by formula (1), wherein $R^4$ represents a C2-C6 alkyl group;

A compound represented by formula (1), wherein $R^4$ represents a C2-C6 haloalkyl group;

A compound represented by formula (1), wherein $R^4$ represents a methyl group, an ethyl group, a propyl group, an isopropyl group, a trifluoromethyl group, or a 2,2,2-trifluoroethyl group;

A compound represented by formula (1), wherein $R^4$ represents an ethyl group;

A compound represented by formula (1), wherein n represents 0, 1, or 2;

A compound represented by formula (1), wherein represents 0;

A compound represented by formula (1), wherein n represents 1;

A compound represented by formula (1), wherein represents 2;

A compound represented by formula (1), wherein p represents 0, 1, 2, or 3;

A compound represented by formula (1), wherein p represents 0 or 1;

A compound represented by formula (1), wherein p represents 0;

A compound represented by formula (1), wherein $R^2$ and $R^3$ represent independently of each other a hydrogen atom, a C1-C6 alkyl group optionally having one or more halogen atoms, a C2-C6 alkoxycarbonyl group, a cyano group, or a halogen atom;

A compound represented by formula (1), wherein $R^2$ and $R^3$ represent independently of each other a hydrogen atom, a C1-C6 alkyl group optionally having one or more halogen atoms, or a halogen atom;

A compound represented by formula (1), wherein $R^2$ and $R^3$ represent independently of each other a hydrogen atom, or a C1-C6 alkyl group optionally having one or more halogen atoms;

A compound represented by formula (1), wherein $R^2$ and $R^3$ represent each a hydrogen atom;

A compound represented by formula (1), wherein A represents a nitrogen atom, or a $CR^6$, and $R^6$ represents a hydrogen atom or a halogen atom;

A compound represented by formula (1), wherein A represents a nitrogen atom, or a CH;

A compound represented by formula (1), wherein A represents N;

A compound represented by formula (1), wherein p represents 0 or 1, and when p represents 1, $R^5$ represents a C1-C6 chain hydrocarbon group optionally having one or more halogen atoms, a phenyl group optionally having one or more atoms or groups selected from Group A, a 5-membered aromatic heterocyclic group selected from Group B (wherein the 5 membered aromatic heterocyclic group may optionally have one or more atoms or groups selected from Group A), a 6 membered aromatic heterocyclic group selected from Group C (wherein the 6-membered aromatic heterocyclic group may optionally have one or more atoms or groups selected from Group A), a 3 to 7 membered nonaromatic heterocyclic group selected from Group D (wherein the 3 to 7 membered nonaromatic heterocyclic group may optionally have one or more atoms or groups selected from the group consisting of a halogen atom and a C1-C6 alkyl group), a $OR^7$, a $NR^8R^9$, a $NR^8C(O)R^{19}$, a $NR^8C(O)OR^{11}$, a $NR^8C(O)NR^{12}R^{13}$, a $N=CHNR^{12}R^{13}$, a $N=S(O)_xR^{12}R^{13}$, a $S(O)_yR^{12}$, a $C(O)OR^8$, a cyano group, or a halogen atom;

A compound represented by formula (1), wherein p represents 0 or 1, and when p represents 1, $R^5$ represents a C1-C6 chain hydrocarbon group optionally having one or more halogen atoms, a 5 membered aromatic heterocyclic group selected from Group B (wherein the 5 membered aromatic heterocyclic group may optionally have one or more atoms or groups selected from Group A), a 6 membered aromatic heterocyclic group selected from Group C (wherein the 6 membered aromatic heterocyclic group may optionally have one or more atoms or groups selected from Group A), a 3 to membered nonaromatic heterocyclic group selected from Group D (wherein the 3 to 7 membered nonaromatic heterocyclic group may optionally have one or more atoms or groups selected from the group consisting of a halogen atom and a C1-C6 alkyl group), a $OR^7$, a $NR^8R^9$, a $S(O)_yR^{12}$, or a halogen atom;

A compound represented by formula (1), wherein p represents 0 or 1, and when p represents 1, $R^5$ represents a C1-C6 chain hydrocarbon group optionally having one or more halogen atoms, a $OR^7$, a $NR^8R^9$, a $S(O)_yR^{12}$, or a halogen atom;

A compound represented by formula (1), wherein p represents 0 or 1, and when p represents 1, $R^5$ represents a C1-C6 haloalkyl group;

A compound represented by formula (1), wherein p represents 0 or 1, and when p represents 1, $R^5$ represents a trifluoromethyl group;

A compound represented by formula (1), wherein $R^1$ represents a C2-C10 chain hydrocarbon group having one or more halogen atoms;

A compound represented by formula (1), wherein $R^1$ represents a C2-C10 haloalkyl group, a C3-C10 haloalkenyl group, or a C3-C10 haloalkynyl group;

A compound represented by formula (1), wherein $R^1$ represents a C2-C10 haloalkyl group;

A compound represented by formula (1), wherein $R^1$ represents a C2-C10 alkyl group having two or more halogen atoms;

A compound represented by formula (1), wherein $R^1$ represents a C2-C10 alkyl group having two or more fluorine atoms;

A compound represented by formula (1), wherein $R^1$ represents a 2,2-difluoroethyl group, a 2,2,2-trifluoroethyl group, 2,2,2-trichloroethyl group, 2,2-difluoropropyl group, 2,2,3,3-tetrafluoropropyl group, 2,2,3,3,3-pentafluoropropyl group, 1,1,1,3,3,3-hexafluoro-2-propyl group, 2,2-(bistrifluoromethyl)-propyl group, 2,2,3,4,4,4-hexafluorobutyl group, 2,2,3,3,4,4,4-heptafluorobutyl group, 2,2,3,3,4,4,5,5,5-nonafluoropentyl group, 2,2,3,3,4,4,5,5,6,6,6-undecafluorohexyl group, 3,3,3-trifluoro-2-propyl group, 3,3,4,4,4-pentafluoro-2-butyl group, or 3,3,4,4,5,5,5-heptafluoro-2-pentyl group;

A compound represented by formula (1), wherein $R^6$ represents a hydrogen atom or a halogen atom;

A compound represented by formula (1), wherein $R^6$ represents a halogen atom;

A compound represented by formula (1), wherein $R^6$ represents a hydrogen atom;

A compound represented by formula (1), wherein A represents a nitrogen atom or a CH, $R^1$ represents a C2-C6 alkyl group having two or more fluorine atoms, $R^2$ and $R^3$ represent independently of each other a hydrogen atom, a C1-C6 alkyl group optionally having one or more halogen atoms, or a halogen group, $R^4$ represents a C1-C6 alkyl group, and p represents 0 or 1, and when p represents 1, $R^5$ represents a C1-C6 alkyl group optionally having one or more halogen atoms;

A compound represented by formula (1), wherein A represents a nitrogen atom or a CH, $R^1$ represents a C2-C6 alkyl group having two or more fluorine atoms, $R^2$ and $R^3$ represent independently of each other a hydrogen atom, a C1-C6 alkyl group optionally having one or more halogen atoms, or a halogen group, $R^4$ represents an ethyl group, and p represents 0 or 1, and when p represents 1, $R^5$ represents a C1-C6 alkyl group optionally having one or more halogen atoms;

A compound represented by formula (1), wherein A represents a nitrogen atom or a CH, $R^1$ represents a C2-C10 alkyl group having two or more fluorine atoms, $R^2$ and $R^3$ represent a hydrogen atom, $R^4$ represents an ethyl group, and p represents 0 or 1, $R^5$ represents a C1-C6 alkyl group optionally having one or more halogen atoms.

A compound represented by formula (1-1):

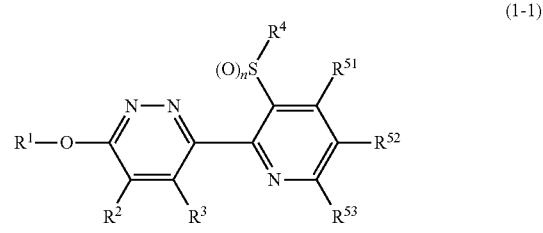

wherein
R¹ represents a C2-C10 alkyl group, a C3-C10 alkenyl group, a C3-C10 alkynyl group, a (C1-C5 alkyl)-O—(C2-C5 alkyl) group, a (C3-C5 alkenyl)-O—(C2-C5 alkyl) group, a (C3-C5 alkynyl)-O—(C2-C5 alkyl) group, a (C1-C5 alkyl)-S(O)$_m$—(C2-C5 alkyl) group, a (C3-C5 alkenyl)-S(O)$_m$—(C2-C5 alkyl) group, a (C3-C5 alkynyl)-S(O)$_m$—(C2-C5 alkyl) group, or a (C1-C5 alkyl)-C(O)—(C1-C5 alkyl) group (wherein R¹ has one or more halogen atoms);

R² and R³ represent independently of each other a hydrogen atom, a C1-C6 alkyl group optionally having one or more halogen atoms, a C2-C6 alkoxycarbonyl group, a cyano group, or a halogen group;

R⁴ represents a C1-C6 chain hydrocarbon group optionally having one or more halogen atoms;

R⁵¹, R⁵², and R⁵³ represent independently of each other a hydrogen atom, a C1-C6 chain hydrocarbon group optionally having one or more halogen atoms, a phenyl group optionally having one or more atoms or groups selected from Group A, a 5 membered aromatic heterocyclic group selected from Group B (wherein the 5 membered aromatic heterocyclic group may optionally have one or more atoms or groups selected from Group A), a 6 membered aromatic heterocyclic group selected from Group C (wherein the 6 membered aromatic heterocyclic group may optionally have one or more atoms or groups selected from Group A), a 3 to 7 membered nonaromatic heterocyclic group selected from Group D (wherein the 3 to 7 membered nonaromatic heterocyclic group may optionally have one or more atoms or groups selected from the group consisting of a halogen atom and a C1-C6 alkyl group), a OR⁷, a NR⁸R⁹, a NR⁸C(O) R¹⁰, a NR⁸C(O) OR¹¹, a NR⁸C(O) NR¹²R¹³, a N═CHNR¹²R¹³, a N═S(O)$_x$R¹²R¹³, a S(O)$_y$R¹², a C(O) OR⁸, a cyano group, or a halogen atom;

n represents 0, 1, or 2;
m represents 0, 1, or 2;
x represents 0 or 1; and
y represents 0, 1, or 2.

A compound represented by formula (1-1), wherein
R¹ represents a C2-C10 haloalkyl group;
R² and R³ represent independently of each other a hydrogen atom, a C1-C6 alkyl group optionally having one or more halogen atoms, or a halogen group;
R⁴ represents a C1-C6 alkyl group optionally having one or more halogen atoms;
R⁵¹, R⁵², and R⁵³ represent independently of each other a hydrogen atom, a C1-C6 chain hydrocarbon group optionally having one or more halogen atoms, a 5 membered aromatic heterocyclic group selected from Group B (wherein the 5 membered aromatic heterocyclic group may optionally have one or more atoms or groups selected from Group A), a 6 membered aromatic heterocyclic group selected from Group C (wherein the 6 membered aromatic heterocyclic group may optionally have one or more atoms or groups selected from Group A), a 3 to 7 membered nonaromatic heterocyclic group selected from Group D (wherein the 3 to 7 membered nonaromatic heterocyclic group may optionally have one or more atoms or groups selected from the group consisting of a halogen atom and a C1-C6 alkyl group), a OR⁷, a NR⁸R⁹, a S(O)$_y$R¹², or a halogen atom;

A compound represented by formula (1-1), wherein R¹ represents a C2-C10 haloalkyl group, R² and R³ represent each a hydrogen atom, R⁴ represents an ethyl group, R⁵¹, R⁵², and R⁵³ represent independently of each other a hydrogen atom, or a C1-C6 alkyl group optionally having one or more halogen atoms;

A compound represented by formula (1-1), wherein R¹ represents a C2-C6 alkyl group having two or more fluorine atoms, R² and R³ represent each a hydrogen atom, R⁴ represents an ethyl group, R⁵¹, R⁵², and R⁵³ represent independently of each other a hydrogen atom, or a C1-C6 alkyl group optionally having one or more halogen atoms.

A compound represented by formula (1-2):

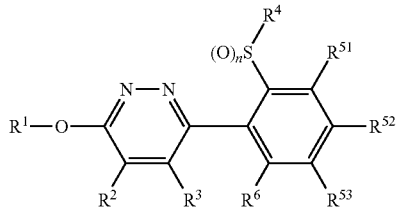

(1-2)

wherein
R¹ represents a C2-C10 alkyl group, a C3-O10 alkenyl group, a C3-C10 alkynyl group, a (C1-C5 alkyl)-O—(C2-C5 alkyl) group, a (C3-C5 alkenyl)-O—(C2-C5 alkyl) group, a (C3-C5 alkynyl)-O—(C2-C5 alkyl) group, a (C1-C5 alkyl)-S(O)$_m$—(C2-C5 alkyl) group, a (C3-C5 alkenyl)-S(O)$_m$—(C2-C5 alkyl) group, a (C3-C5 alkynyl)-S(O)$_m$—(C2-C5 alkyl) group, or a (C1-C5 alkyl-C(O)—(C1-C5 alkyl) group (wherein R¹ has one or more halogen atoms);

R² and R³ represent independently of each other a hydrogen atom, a C1-C6 alkyl group optionally having one or more halogen atoms, a C2-C6 alkoxycarboxyl group, a cyano group, or a halogen group;

R⁴ represents a C1-C6 chain hydrocarbon group optionally having one or more halogen atoms;

R⁵ represents a C1-C6 chain hydrocarbon group optionally having one or more halogen atoms, a phenyl group optionally having one or more atoms or groups selected from Group A, a 5 membered aromatic heterocyclic group selected from Group B (wherein the 5 membered aromatic heterocyclic group may optionally have one or more atoms or groups selected from Group A), a 6 membered aromatic heterocyclic group selected from Group C (wherein the 6 membered aromatic heterocyclic group may optionally have one or more atoms or groups selected from Group A), a 3 to 7 membered nonaromatic heterocyclic group selected from Group D (wherein the 3 to 7 membered nonaromatic heterocyclic group may optionally have one or more atoms or groups selected from the group consisting of a halogen atom and a C1-C6 alkyl group), a OR⁷, a NR⁸R⁹, a NR⁸C(O)R¹⁹, a NR⁸C(O) OR¹¹, a NR⁸C(O) NR¹²R¹³, a N═CHNR¹²R¹³, a N═S(O)$_x$R¹²R¹³, a S(O)$_y$R¹², a C(O) OR⁸, a cyano group, or a halogen atom;

R⁶ represents a hydrogen atom, or a halogen atom;
n represents 0, 1, or 2;
m represents 0, 1, or 2;
x represents 0 or 1; and
y represents 0, 1, or 2.

A compound represented by formula (1-2), wherein
R¹ represents a C2-C10 haloalkyl group;
R² and R³ represent independently of each other a hydrogen atom, a C1-C6 alkyl group optionally having one or more halogen atoms, or a halogen group;
R⁴ represents a C1-C6 alkyl group optionally having one or more halogen atoms;
R⁵¹, R⁵², and R⁵³ represent independently of each other a hydrogen atom, a C1-C6 chain hydrocarbon group optionally having one or more halogen atoms, a 5 membered aromatic heterocyclic group selected from Group B (wherein the 5 membered aromatic heterocyclic group may optionally have one or more atoms or groups selected from Group A), a 6 membered aromatic heterocyclic group selected from Group C (wherein the 6 membered aromatic heterocyclic group may optionally have one or more atoms or groups selected from Group A), a 3 to 7-membered nonaromatic heterocyclic group selected from Group D (wherein the 3 to 7 membered nonaromatic heterocyclic group may optionally have one or more atoms or groups selected from the group consisting of a halogen atom and a C1-C6 alkyl group), a $OR^7$, a $NR^8R^9$, a $S(O)_yR^{12}$, or a halogen atom; and $R^6$ represents a hydrogen atom, or a halogen atom;

A compound represented by formula (1-2), wherein $R^1$ represents a C2-C10 haloalkyl group, $R^2$ and $R^3$ represent each a hydrogen atom, $R^4$ represents an ethyl group, $R^{51}$, $R^{52}$, and $R^{53}$ represent independently of each other a hydrogen atom, or a C1-C6 alkyl group optionally having one or more halogen atoms, and $R^6$ represents a hydrogen atom;

A compound represented by formula (1-2), wherein $R^1$ represents a C2-C6 alkyl group having two or more fluorine atoms, $R^2$ and $R^3$ represent each a hydrogen atom, $R^4$ represents an ethyl group, $R^{51}$, $R^{52}$, and $R^{53}$ represent independently of each other a hydrogen atom, or a C1-C6 alkyl group optionally having one or more halogen atoms, $R^6$ represents a hydrogen atom.

Examples of the N-oxide compound include the following compounds.

A compound represented by formula (1-N):

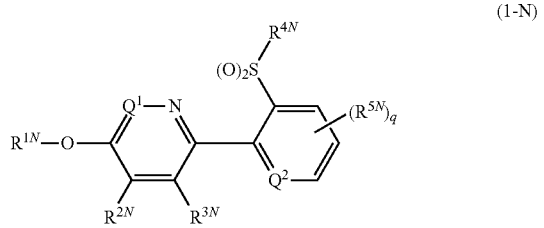

wherein
Q$^1$ represents a N$^+$—O$^-$ or a nitrogen atom,
Q$^2$ represents an N$^+$—O$^-$, a CR$^{6N}$, or a nitrogen atom, wherein at least one of Q$^1$ and Q$^2$ represents an N$^+$—O$^-$;
R$^{6N}$ represents a hydrogen atom, or a halogen atom;
R$^{1N}$ represents a C2-C10 haloalkyl group;
R$^{2N}$ and R$^{3N}$ represent independently of each other a hydrogen atom, a C1-C3 alkyl group optionally having one or more halogen atoms, or a halogen group;
R$^{4N}$ represents a C1-06 alkyl group optionally having one or more halogen atoms; and
q represents 0 or 1, wherein when q represents 1, R$^{5N}$ represents a C1-C6 alkyl group optionally having one or more halogen atoms.

A compound represented by formula (1-N), wherein
Q$^1$ represents a N$^+$—O$^-$;
Q$^2$ represents a N$^+$—O$^-$, a CH, a CF, or a nitrogen atom;
R$^{1N}$ represents a C2-C10 haloalkyl group;
R$^{2N}$ and R$^{3N}$ represent a hydrogen atom;
R$^{4N}$ represents a C1-C6 alkyl group optionally having one or more halogen atoms; and
q represents 0 or 1, wherein when q represents 1, R$^{5N}$ represents a C1-C6 alkyl group optionally having one or more halogen atoms.

A compound represented by formula (1-N), wherein
Q$^1$ represents a N$^+$—O$^-$;
Q$^2$ represents a nitrogen atom or a CH;
R$^{1N}$ represents a C2-C10 haloalkyl group;
R$^{2N}$ and R$^{3N}$ represent each a hydrogen atom;
R$^{4N}$ represents an ethyl group; and
q represents 0 or 1, wherein when q represents 1, R$^{5N}$ represents a C1-C6 alkyl group optionally having one or more halogen atoms.

A compound represented by formula (1-N), wherein
Q$^1$ represents an N$^+$—O$^-$;
Q$^2$ represents a nitrogen atom;
R$^{1N}$ represents a C2-C10 haloalkyl group;
R$^{2N}$ and R$^{3N}$ represent each a hydrogen atom;
R$^{4N}$ represents an ethyl group; and
q represents 0 or 1, wherein when q represents 1, R$^{5N}$ represents a C1-C6 alkyl group optionally having one or more halogen atoms.

A compound represented by formula (1-N1):

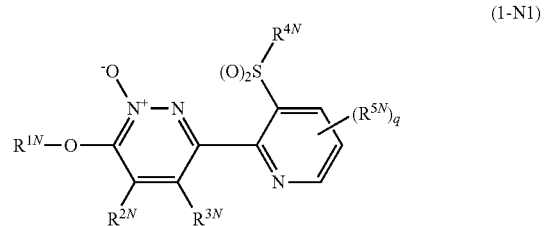

wherein
R$^{1N}$ represents a C2-C10 haloalkyl group;
R$^{2N}$ and R$^{3N}$ represent independently of each other a hydrogen atom, a C1-C3 alkyl group optionally having one or more halogen atoms, or a halogen group;
R$^{4N}$ represents a C1-C6 alkyl group optionally having one or more halogen atoms;
R$^{5N}$ represents a C1-C6 alkyl group optionally having one or more halogen atoms; and
q represents 0 or 1.

A compound represented by formula (1-N1), wherein
R$^{1N}$ represents a C2-C10 haloalkyl group;
R$^{2N}$ and R$^{3N}$ represent each a hydrogen atom;
R$^{4N}$ represents a C1-C6 alkyl group optionally having one or more halogen atoms;
R$^{5N}$ represents a C1-C6 alkyl group optionally having one or more halogen atoms; and
q represents 0 or 1.

A compound represented by formula (1-N1), wherein
R$^{1N}$ represents a C3-C6 alkyl group having two or more fluorine atoms;
R$^{2N}$ and R$^{3N}$ represent each a hydrogen atom;
R$^{4N}$ represents an ethyl group;
R$^{5N}$ represents a C1-C6 alkyl group optionally having one or more halogen atoms; and
q represents 0 or 1.

A compound represented by formula (1-N2):

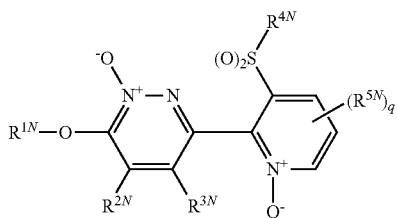

(1-N2)

wherein $R^{1N}$ represents a C2-C10 haloalkyl group;

$R^{2N}$ and $R^{3N}$ represent independently of each other a hydrogen atom, a C1-C3 alkyl group optionally having one or more halogen atoms, or a halogen group;

$R^{4N}$ represents a C1-C6 alkyl group optionally having one or more halogen atoms;

$R^{5N}$ represents a C1-C6 alkyl group optionally having one or more halogen atoms; and q represents 0 or 1.

A compound represented by formula (1-N2), wherein $R^{1N}$ represents a C2-C10 haloalkyl group;

$R^{2N}$ and $R^{3N}$ represent each a hydrogen atom;

$R^{4N}$ represents a C1-C6 alkyl group optionally having one or more halogen atoms;

$R^{5N}$ represents a C1-C6 alkyl group optionally having one or more halogen atoms; and q represents 0 or 1.

A compound represented by formula (1-N2), wherein $R^{1N}$ represents a C3-C6 alkyl group having two or more fluorine atoms;

$R^{2N}$ and $R^{3N}$ represent a hydrogen atom;

$R^{4N}$ represents an ethyl group;

$R^{5N}$ represents a C1-C6 alkyl group optionally having one or more halogen atoms; and q represents 0 or 1.

A compound represented by formula (1-N3):

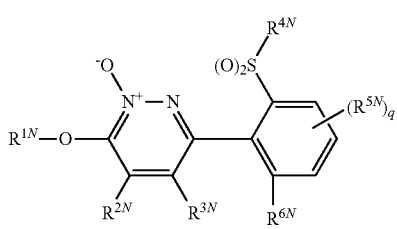

(1-N3)

wherein $R^{1N}$ represents a C2-C10 haloalkyl group;

$R^{2N}$ and $R^{3N}$ represent independently of each other a hydrogen atom, a C1-C3 alkyl group optionally having one or more halogen atoms, or a halogen group;

$R^{4N}$ represents a C1-C6 alkyl group optionally having one or more halogen atoms;

$R^{5N}$ represents a C1-C6 alkyl group optionally having one or more halogen atoms;

q represents 0 or 1; and $R^{6N}$ represents a hydrogen atom, or a halogen atom.

A compound represented by formula (1-N3), wherein $R^{1N}$ represents a C2-C10 haloalkyl group;

$R^{2N}$ and $R^{3N}$ represent each a hydrogen atom;

$R^{4N}$ represents a C1-C6 alkyl group optionally having one or more halogen atoms;

$R^{5N}$ represents a C1-C6 alkyl group optionally having one or more halogen atoms;

q represents 0 or 1; and $R^{6N}$ represents a hydrogen atom, or a fluorine atom.

A compound represented by formula (1-N3), wherein $R^{1N}$ represents a C3-C6 alkyl group having two or more fluorine atoms;

$R^{2N}$ and $R^{3N}$ represent each a hydrogen atom;

$R^{4N}$ represents an ethyl atom;

$R^{5N}$ represents a C1-C6 alkyl group optionally having one or more halogen atoms; and q represents 0 or 1.

Next, a process for preparing the present compound is described.

The present compound and the immediate compound can be prepared, for example, according to the following (Processe 1) to (Process 12).

Process 1

The present compound (1b) represented by formula (1) wherein n is 1 (hereinafter, referred to as "Present compound (1b)") and the present compound (1c) wherein n is 2 (hereinafter, referred to as "Present compound (1c)") may be prepared by reacting the present compound (1a) wherein n is 0 (hereinafter, referred to as "Present compound (1a)") with an oxidizing agent.

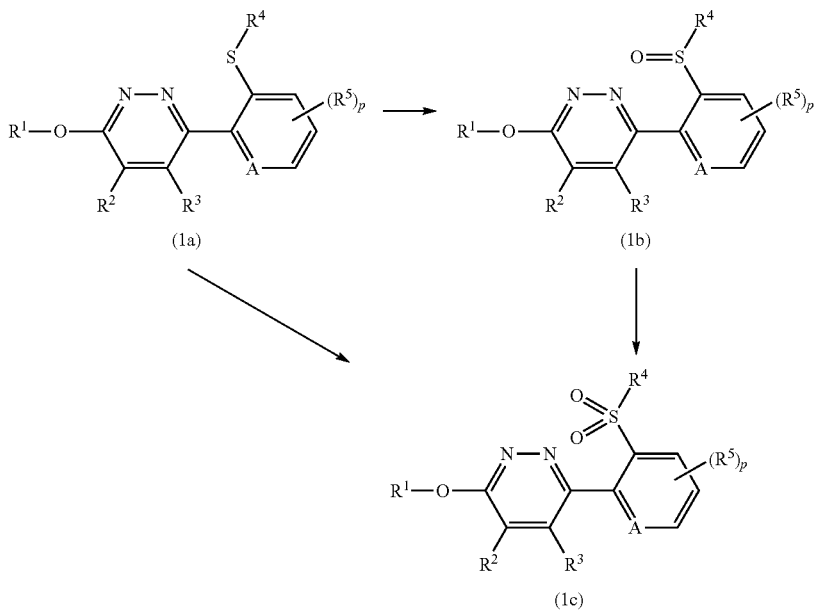

wherein the symbols are the same as those defined in the formula (1).

First, a process for preparing Present compound (1b) from Present compound (1a) is described.

The reaction is usually carried out in the presence of a solvent.

Examples of the solvent to be used in the reaction include halogenated aliphatic hydrocarbons (hereinafter, collectively referred to as "halogenated aliphatic hydrocarbons") such as dichloromethane and chloroform; nitriles (hereinafter, collectively referred to "nitriles") such as acetonitrile; alcohols (hereinafter, collectively referred to as "alcohols") such as methanol and ethanol; acetic acid; water; and mixed solvents thereof.

Examples of the oxidizing agent to be used in the reaction includes sodium periodate, m-chloroperoxybenzoic acid (hereinafter, referred to as "mCPBA"), and hydrogen peroxide.

When hydrogen peroxide is used as the oxidizing agent, a base or a catalyst may be added as needed.

Examples of the base to be used in the reaction include sodium carbonate.

Examples of the catalyst to be used in the reaction include tungstic acid, and sodium tungstate.

In the reaction, the oxidizing agent is used usually within a range of 1 to 1.2 molar ratio(s), as opposed to 1 mole of Present compound (1a).

In the reaction, the base is used usually within a range of 0.01 to 1 molar ratio(s), as opposed to 1 mole of Present compound (1a).

In the reaction, the catalyst is used usually within a range of 0.01 to 0.5 molar ratios, as opposed to 1 mole of Present compound (1a).

A reaction temperature in the reaction is usually within a range of −20 to 80° C. A reaction period in the reaction is usually within a range of 0.1 to 12 hours.

When the reaction is completed, the reaction mixture is extracted with organic a solvent, and the organic layer is optionally washed with an aqueous solution of a reducing agent such as sodium sulfite and sodium thiosulfate, and an aqueous solution of a base such as sodium hydrogen carbonate. The resulting organic layer is dried and concentrated to give Present compound (1b). The obtained Present compound (1b) may be further purified with a chromatography, and recrystallization, etc.

Next, a process for preparing Present compound (1c) from Present compound (1b) is explained.

The reaction is usually carried out in the presence of a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide.

When hydrogen peroxide is used as the oxidizing agent, a base or a catalyst may be added as needed.

Examples of the base to be used include sodium carbonate.

Examples of the catalyst to be used include sodium tungstate.

In the reaction, the oxidizing agent is used usually within a range of 1 to 4 molar ratio(s) as opposed to 1 mole of Present compound (1b). Preferably, the oxidizing agent is used within a range of 1 to 2 molar ratio(s) as opposed to 1 mole of Present compound (1b).

In the reaction, the base is used usually within a range of 0.01 to 1 molar ratio(s) as opposed to 1 mole of Present compound (1b).

In the reaction, the catalyst is used usually within a range of 0.01 to 0.5 molar ratios as opposed to 1 mole of Present compound (1b).

A reaction temperature in the reaction is usually within a range of −20 to 120° C. A reaction period in the reaction is usually within a range of 0.1 to 12 hours.

When the reaction is completed, the reaction mixture is extracted with an organic solvent, and the organic layer is optionally washed with an aqueous solution of a reducing agent such as sodium sulfite and sodium thiosulfate, and an aqueous solution of a base such as sodium hydrogen carbonate. The resulting organic layer is dried and concentrated to give Present compound (1c). The obtained Present compound (1c) may be further purified with a chromatography, and recrystallization, etc.

Also, Present compound (1c) may be prepared in one step (one-spot) by reacting Present compound (1a) with an oxidizing agent.

The reaction is usually carried out in the presence of a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide.

When hydrogen peroxide is used as oxidizing agent, a base or a catalyst may be added as needed.

Examples of the base to be used include sodium carbonate.

Examples of the catalyst to be used include tungstate, and sodium tungstate, etc.

In the reaction, the oxidizing agent is used usually within a range of 2 to 5 molar ratios as opposed to 1 mole of Present compound (1a).

In the reaction, the base is used usually within a range of 0.01 to 1 molar ratio(s) as opposed to 1 mole of Present compound (1a).

In the reaction, the catalyst is used usually within a range of 0.01 to 0.5 molar ratios as opposed to 1 mole of Present compound (1a).

A reaction temperature in the reaction is usually within a range of $-20$ to $120°$ C. A reaction period in the reaction is usually within a range of 0.1 to 12 hours.

When the reaction is completed, the reaction mixture is extracted with an organic solvent, and the organic layer is optionally washed with an aqueous solution of a reducing agent such as sodium sulfite and sodium thiosulfate, and an aqueous solution of a base such as sodium hydrogen carbonate. The resulting organic layer is dried and concentrated to give Present compound (1c). The obtained Present compound (1c) may be further purified with a chromatography, and recrystallization, etc.

Process 2

Present compound (1a) may be prepared by reacting a compound represented by formula (M1) (hereinafter, referred to as "Compound (M1)") with a compound represented by formula (R1) (hereinafter, referred to as "Compound (R1)") in the presence of a base.

wherein V represents a halogen atom, and the other symbols are the same as those defined in the formula (1).

The reaction is usually carried out in the presence of a solvent.

Examples of the solvent to be used in the reaction include ethers (hereinafter, referred to as "ethers") such as tetrahydrofuran (hereinafter, referred to as "THF"), ethyleneglycol dimethyl ether, methyl tert-butyl ether, and 1,4-dioxane; aromatic hydrocarbons (hereinafter, referred to as "aromatic hydrocarbons") such as toluene and xylene; nitrils; polar aprotic solvents (hereinafter, referred to as "polar aprotic solvents") such as N,N-dimethylformamide (hereinafter, referred to as "DMF"), N-methyl pyrrolidone (hereinafter, referred to as "NMP") and dimethyl sulfoxide (hereinafter, referred to "DMSO"); water; and mixed solvents thereof.

Examples of the base to be used in the reaction include alkali metal carbonates (hereinafter, referred to as "alkali metal carbonates") such as sodium carbonate and potassium carbonate; and alkali metal hydrides (hereinafter, referred to as "alkali metal hydrides") such as sodium hydride.

In the reaction, Compound (R1) is usually used within a range of in 1 to 10 molar ratio(s) as opposed to 1 mole of Compound (M1). Preferably, Compound (R1) is used within a range of in 1.0 to 1.1 molar ratio(s), and the base is used within a range of 1 to 2 molar ratio(s) as opposed to 1 mole of Compound (M1).

A reaction temperature in the reaction is usually within a range of $-20$ to $150°$ C. A reaction period in the reaction is usually within a range of 0.5 to 24 hours.

When the reaction is completed, the reaction mixture is extracted with an organic solvent, and the resulting organic layer is worked up such as drying and concentration to give Present compound (1a). The obtained Present compound (1a) may be further purified with a chromatography, and recrystallization, etc.

In the reaction, V is preferably a fluorine atom or a chlorine atom.

Process 3

Present compound (1) may be prepared by reacting a compound represented by formula (M2) (hereinafter, referred to as "Compound (M2)") with a compound represented by formula (R2) (hereinafter, referred to as "Compound (R2)") in the presence of a base.

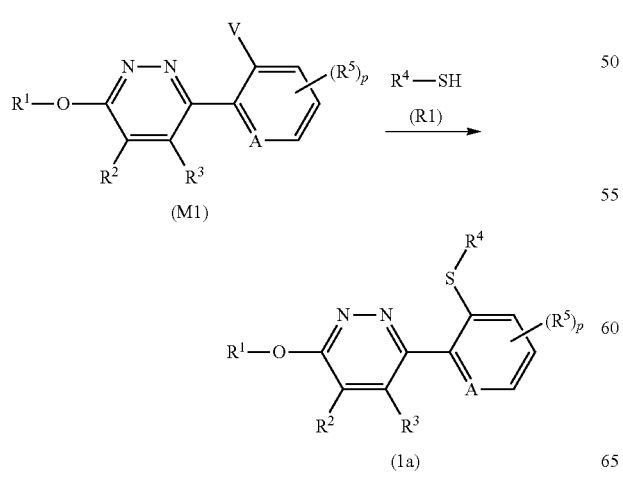

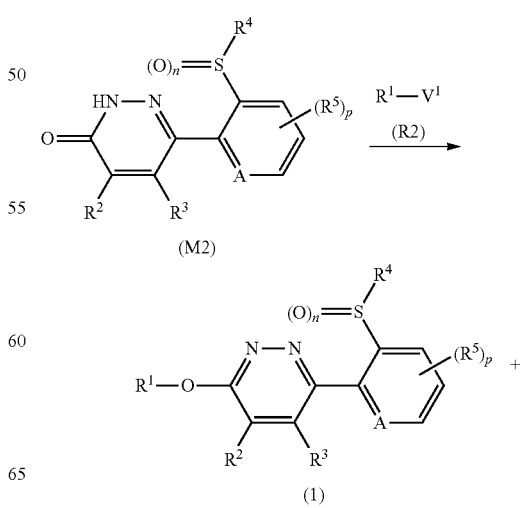

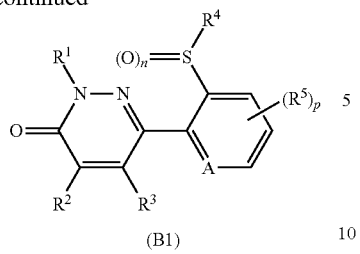

(B1)

wherein V¹ represents a halogen atom, a methylsulfonyloxy group, a trifluoromethylsulfonyloxy group, a nonafluorobutanesulfonyloxy group, or a para-toluenesulfonyloxy group, and the other symbols are the same as those defined in the formula (1).

The reaction is usually carried out in the presence of a solvent.

Examples of the solvent to be used in the reaction include ethers, halogenated aliphatic hydrocarbons, aromatic hydrocarbons, polar aprotic solvents, and mixed solvents thereof.

Examples of the base to be used in the reaction include organic bases (hereinafter, referred to as "organic bases") such as triethylamine, diisopropylethylamine, pyridine and 4-dimethylaminopyridine; alkali metal hydrides; or alkali metal carbonates.

In the reaction, Compound (R2) is usually used within a range of in 1 to 10 molar ratio(s), and the base is used within a range of 0.1 to 5 molar ratio(s), as opposed to 1 mole of Compound (M2).

A reaction temperature in the reaction is usually within a range of −20 to 120° C. A reaction period in the reaction is usually within a range of 0.1 to 24 hours.

In the reaction, the compound represented by formula (B1) may be produced as a by-product.

When the reaction is completed, the reaction mixture is extracted with an organic solvent, and the resulting organic layer is concentrated; the reaction mixture is added to water, and the resulting solid is collected through filtration; or the solid in the reaction mixture is collected through filtration to obtain Present compound (1). The obtained Present compound (1) may be further purified with a chromatography, and recrystallization, etc.

Process 4

Present compound (1) may be prepared by reacting a compound represented by formula (M3) (hereinafter, referred to as "Compound (M3)") with a compound represented by formula (R3) (hereinafter, referred to as "Compound (R3)") in the nresence of a base.

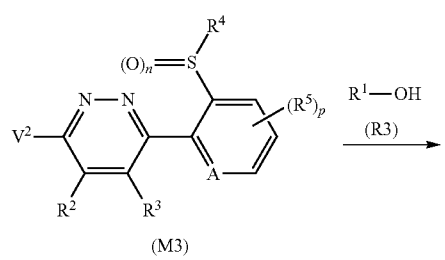

(M3)

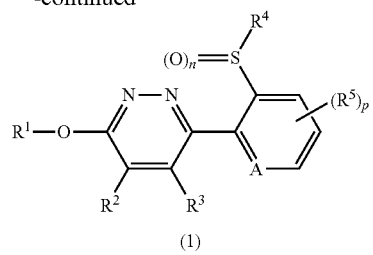

(1)

wherein V² represents a halogen atom or a methylsulfonyl group, and the other symbols are the same as those defined in the formula (1).

The reaction is usually carried out in the presence of a solvent.

Examples of the solvent to be used in the reaction include ethers, aromatic hydrocarbons, nitrils, polar aprotic solvents, water, and mixed solvents thereof.

Examples of the base to be used in the reaction include alkali metal carbonates, and alkali metal hydrides.

In the reaction, Compound (R3) is usually used within a range of in 1 to 100 molar ratio(s), and the base is used within a range of 1 to 10 molar ratio(s), as opposed to 1 mole of Compound (M3). Preferably, Compound (R3) is used within a range of in 1.0 to 1.5 molar ratio(s), and the base is used within a range of 1.0 to 2.0 molar ratio(s), as opposed to 1 mole of Compound (M3).

A reaction temperature in the reaction is usually within a range of −20 to 150° C. A reaction period in the reaction is usually within a range of 0.5 to 24 hours.

When the reaction is completed, the reaction mixture is extracted with an organic solvent, and the resulting organic layer is worked up such as drying and concentration to give Present compound (1). The obtained Present compound (1) may be further purified with a chromatography, and recrystallization, etc.

In the reaction, V² is preferably a chlorine atom, or a methylsulfonyl group.

Process 5

Compound (M1) may be prepared by reacting a compound represented by formula (M4) (hereinafter, referred to as "Compound (M4)") with a compound represented by formula (R2) (hereinafter, referred to as "Compound (R2)") in the presence of a base.

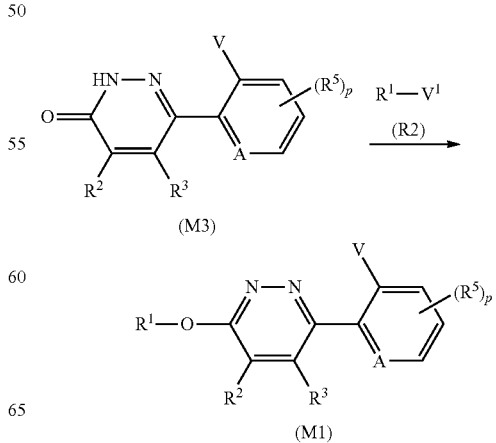

(M3)

(M1)

-continued

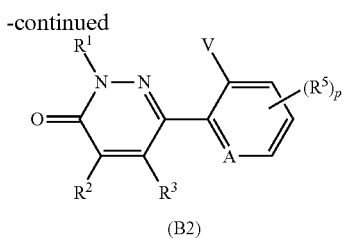

(B2)

wherein the symbols are the same as those defined in the formula (1).

The reaction may be carried out according to the similar method to that described in Process 3 by using Compound (M4) instead of Compound (M2).

In the reaction, a compound represented by formula (B2) may be produced as a by-product.

Process 6

Compound (M1) may be prepared by reacting a compound represented by formula (M6) (hereinafter, referred to as "Compound (M6)") with a compound represented by formula (M7) (hereinafter, referred to as "Compound (M7)") in the presence of a metal catalyst.

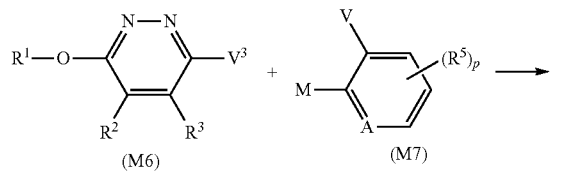

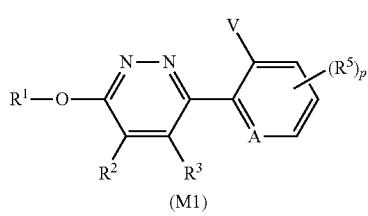

(M1)

wherein $V^3$ represents a halogen atom, M represents 9-borabicyclo[3.3.1]nona-9-yl group, —B(OH)$_2$, 4,4,5,5-tetramethyl-1,3,2-dioxaborolan-2-yl group, —SnBu$_3$, —ZnCl, —MgCl, or MgBr; and the other symbols are the same as those defined above.

Compound (M6) may be prepared according to a similar method to that described in US patent application publication No. 2010/0261727.

Compound (M7) may be prepared according to a similar method to that described in International Publication No. 03/024961 or Organic Process Research & DevelopMent, 2004, 8, 192-200.

The reaction is usually carried out in the presence of a solvent.

Examples of the solvent to be used in the reaction include ethers, aromatic hydrocarbons, polar aprotic solvents, water, and mixed solvents thereof.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0) and palladium(II) acetate; nickel catalysts such as bis(cyclooctadiene)nickel(0) and nickel(II) chloride; and copper catalyst such as copper(I) iodide and copper(I) chloride.

In the reaction, a ligand, a base and an inorganic halogenated compound may be added as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-(dicyclohexylphosphino)-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline, etc.

Examples of the base to be used in the reaction include alkali metal hydrides, alkali metal carbonates, or organic bases.

Examples of the inorganic halogenated compounds to be used in the reaction include alkali metal fluorides such as potassium fluoride and sodium fluoride; and alkali metal chlorides such as lithium chloride and sodium chloride.

In the reaction, Compound (M7) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 5 molar ratios, and the inorganic halogenated compound is usually used within a range of 0.1 to 5 molar ratios, as opposed to 1 mole of Compound (M6).

A reaction temperature in the reaction is usually within a range of −20 to 200° C. A reaction period in the reaction is usually within a range of 0.1 to 24 hours.

When the reaction is completed, to the reaction mixtures is added water, and the reaction mixture is then extracted with an organic solvent, and the resulting organic layer is concentrated; the reaction mixture is added to water, and the resulting solid is collected through filtration; or the solid in the reaction mixture is collected through filtration to obtain Present compound (M1). The obtained Present compound (M1) may be further purified using a chromatography, and recrystallization, etc.

In the reaction, $V^3$ is preferably a chlorine atom, a bromine atom, or an iodine atom.

Process 7

A compound of Compound (M2) wherein n is 0 (M2a), a compound of Compound (M2) wherein n is 1 (M2b), and a compound of Compound (M2) wherein n is 2 (M2c) may be prepared according to a method described as follows.

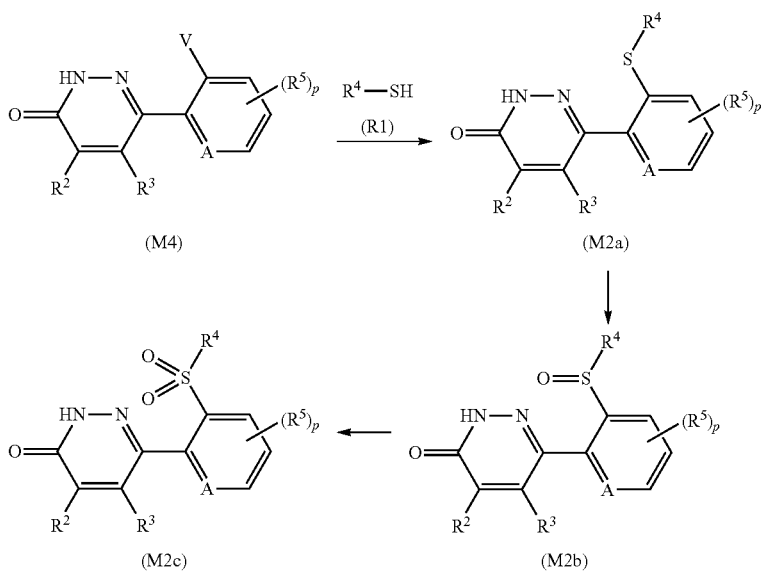

wherein V represents a halogen atom, and the other symbols are the same as those defined in the formula (1).

First, a process for preparing Compound (M2a) from Compound (M4) is described.

Compound (M2a) may be prepared according to the method described in Process 2 using Compound (M4) instead of Compound (M1).

Next, a process for preparing Compound (M2b) from Compound (M2a) and Compound (M2c) from Compound (M2b) is described.

Compound (M2b) may be prepared according to the method described in Process 1 using Compound (M2a) instead of Compound (1a).

Compound (M2c) may be prepared according to the method described in Process 1 using Compound (M2b) instead of Compound (1b).

Process 8

Compound (M2) may be prepared by reacting a compound represented by formula (M8) (hereinafter, referred to as "Compound (M8)") with a compound represented by formula (M4) (hereinafter, referred to as "Compound (M4)") in the presence of a base or an acid, and reacting the obtained compound with hydrazine.

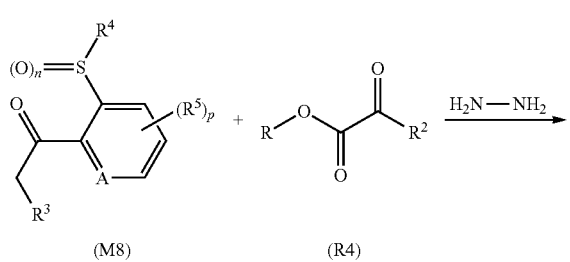

-continued

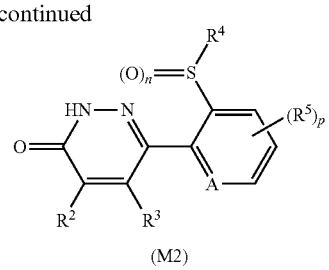

wherein R represents a hydrogen atom, a methyl group, or an ethyl group, and the other symbols are the same as those defined above.

Compound (M8) may be prepared according to a similar method to that described in Journal of American Chemical Society, 2012, 134(6), 2906-2909, or International Publication No. 2014/010990.

The reaction is usually carried out in the presence of a solvent.

Examples of the solvent to be used in the reaction include methanol, ethanol, ethers, polar aprotic solvents, water, and mixed solvents thereof.

Examples of the base to be used in the reaction include alkali metal hydroxides (hereinafter, referred to as "alkali metal hydroxides") such as sodium hydroxide and potassium hydroxide, alkali metal carbonates, or alkali metal hydrides.

Examples of the acid to be used in the reaction include organic carbonic acids such as acetic acid and formic acid, and mineral acids such as hydrochloric acid and sulfuric acid.

In the reaction, Compound ($R^4$) is usually used within a range of 1 to 10 molar ratio(s), the base is usually used within a range of 1 to 10 molar ratios, the acid is usually used within a range of 1 to 10 molar ratio(s), and hydrazine is usually used within a range of 1 to 10 molar ratios, as opposed to 1 mole of Compound (M8).

A reaction temperature in the reaction is usually within a range of −20 to 150° C. A reaction period in the reaction is usually within a range of 0.5 to 24 hours.

When the reaction is completed, the reaction mixture is extracted with an organic solvent, and the organic layer is worked up such as drying and concentration to give Compound (M2). The obtained Compound (M2) may be further purified with a chromatography, and recrystallization, etc.

Process 9

A compound of Compound (M3) wherein n is 1 (M3b), and a compound of Compound (M3) wherein n is 2 (M3c) may be prepared by reacting a compound of Compound (M3) wherein n is 0 (M3a) with an oxidizing agent.

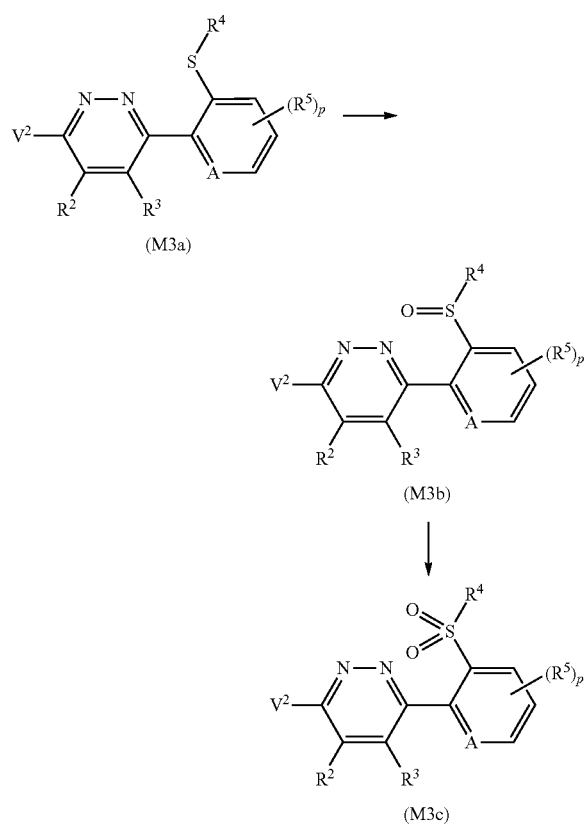

wherein the symbols are the same as those defined above.

Compound (M3b) may be prepared according to the method described in Process 1 using Compound (M3a) instead of Compound (1a).

Compound (M3c) may be prepared according to the method described in Process 1 using Compound (M3b) instead of Compound (1b).

Process 10

A compound of Compound (M3) wherein $V^2$ is a chlorine atom or a bromine atom (M3d), and a compound of Compound (M3) wherein $V^2$ is a methylsulfonyl (M3e) may be prepared according to a method described as follows.

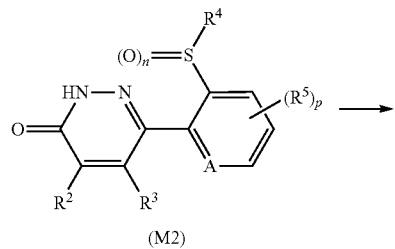

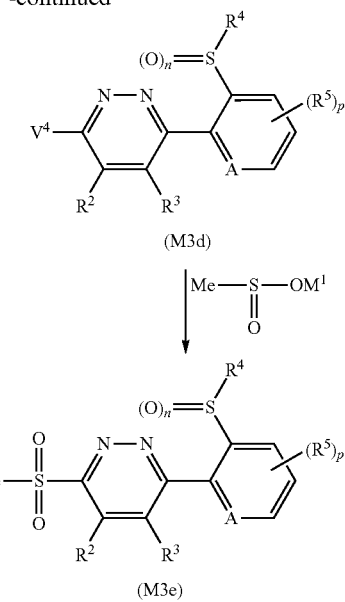

wherein $V^4$ represents a chlorine atom or a bromine atom, $M^1$ represents sodium, and the other symbols are the same as those defined above.

First, a process for preparing Compound (M3d) from Compound (M2) is described.

Compound (M3d) may be prepared by reacting Compound (M2) with a halogenating agent.

The reaction is usually carried out in the presence of a solvent.

Examples of the solvent to be used in the reaction include ethers, halogenated hydrocarbons, and aliphatic hydrocarbons.

Examples of the halogenating agent to be used in the reaction include thionyl chloride, phosphorus oxychloride, and phosphorus oxybromide, etc.

In the reaction, a catalyst may be added as needed.

Examples of the catalyst to be used in the reaction include DMF.

In the reaction, the halogenating agent is usually used within a range of 1 to 10 molar ratio(s), and the catalyst is usually used within a range of 0.01 to 0.1 molar ratio(s), as opposed to 1 mole of Compound (M2). Further, in the reaction, thionyl chloride and phosphorus oxychloride in the state of liquid may be used as a solvent.

A reaction temperature in the reaction is usually within a range of −20 to 150° C. A reaction period in the reaction is usually within a range of 0.5 to 24 hours.

When the reaction is completed, to the reaction mixture is added water after evaporating an excess of the halogenating agent under reduced pressure, and then the obtained mixture is extracted with an organic solvent, and the organic layer is worked up such as drying and concentration to give Compound (M3d). The obtained Compound (M3d) may be further purified with a chromatography, and recrystallization, etc.

Next, a process for preparing Compound (M3e) from Compound (M3d) is described.

Compound (M3e) may be prepared by reacting Compound (M3d) with sodium methanesulfinate.

The reaction is usually carried out in the presence of a solvent.

Examples of the solvent to be used in the reaction include polar aprotic solvents.

In the reaction, a catalyst may be added as needed.

Examples of the catalyst to be used in the reaction include quaternary ammonium salts such as tetrabutylammonium chloride, etc.

In the reaction, sodium methanesulfinate is usually used within a range of 1 to 10 molar ratio(s), and the catalyst is usually used within a range of 0.01 to 0.5 molar ratio(s), as opposed to 1 mole of Compound (M3d).

A reaction temperature in the reaction is usually within a range of −20 to 150° C. A reaction period in the reaction is usually within a range of 0.5 to 24 hours.

When the reaction is completed, the reaction mixture is extracted with an organic solvent, and the organic layer is worked up such as drying and concentration to give Compound (M3e). The obtained Compound (M3e) may be further purified with a chromatography, and recrystallization, etc.

Process 11

Compound (M4) may be prepared according to a method described as follows.

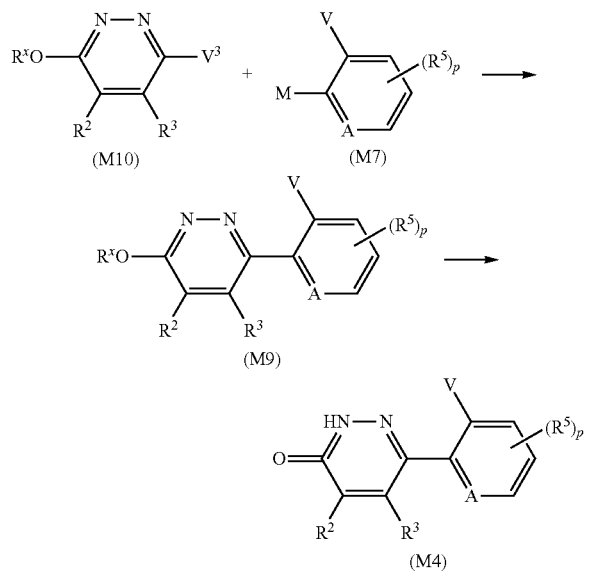

wherein $R^x$ represents a methyl group and an ethyl group, and the other symbols are the same as those defined above.

Compound, (M10) may be prepared according to a similar method to that described in US patent application publication No. 2010/0261727.

First, a process for preparing a compound represented by formula (M9) (hereinafter, referred to as "Compound (M9)") is described.

Compound (M9) may be prepared according to the method described in Process 6 using a compound represented by formula (M10) (hereinafter, referred to as "Compound (M10)") instead of Compound (M6).

Next, a process for preparing Compound (M4) from Compound (M9) is described.

Compound (M4) may be prepared by reacting Compound (M9) in the presence of an acid.

The reaction is usually carried out in the presence of a solvent.

Examples of the solvent to be used in the reaction include halogenated aliphatic hydrocarbons, aromatic hydrocarbons, nitrils, alcohols, acetic acid, water, and mixed solvents thereof.

Examples of the acid to be used in the reaction include mineral acids such as hydrochloric acid, boron halides such as boron trichloride and boron tribromide, and metal chlorides such as titanium chloride and aluminium chloride.

In the reaction, the acid is usually used within a range of 0.1 to 10 molar ratio(s) as opposed to 1 mole of Compound (M-9). In the reaction, when the mineral acid is used as an acid, the mineral acid can be also used as a solvent.

A reaction temperature in the reaction is usually within a range of −20 to 150° C. A reaction period in the reaction is usually within a range of 0.1 to 24 hours.

When the reaction is completed, to the reaction mixture is added water, and the reaction mixture is then extracted with an organic solvent, and the resulting organic layer is concentrated; the reaction mixture is added to water, and the resulting solid is collected through filtration; or the solid in the reaction mixture is collected through filtration to give Present compound (M4). The obtained Present compound (M4) may be further purified with a chromatography, and recrystallization, etc.

A compound of Compound (M8) wherein n is 0 (M8a), a compound of Compound (M8) wherein n is 1 (M8b), and a compound of Compound (M8) wherein n is 2 (M8c) may be prepared according to a method described as follows.

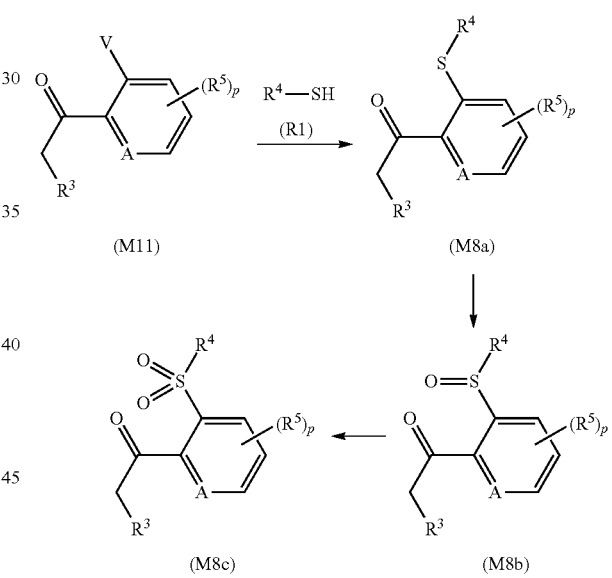

wherein the symbols are the same as those defined above.

Compound (M11) is a known compound, or may be prepared according to a known method or a similar method to that described in International Publication No. 2014/010990.

First, a process for preparing Compound (M8a) from a compound represented by formula (M11) (hereinafter, referred to as "Compound (M11)") is described.

Compound (M8a) may be prepared according to the method described in Process 2 using Compound (M11) instead of Compound (M1).

Next, a process for preparing Compound (M8b) from Compound (M8a) and Compound (M8c) from Compound (M8b) is described.

Compound (M8b) may be prepared according to the method described in Process 1 using Compound (M8a) instead of Compound (1a).

Compound (M8c) may be prepared according to the method described in Process 1 using Compound (M8b) instead of Compound (1b).

Process 13

An N-oxide compound represented by formula (N11) (hereinafter, referred to as "N-oxide compound (N11)"), an N-oxide compound represented by formula (N12) (hereinafter, referred to as "N-oxide compound (N12)"), and an N-oxide compound represented by formula (N13) (hereinafter, referred to as "N-oxide compound (N13)") may be prepared by reacting the present compound represented by formula (1dN) (hereinafter, referred to as "Present compound (1dN)") with an oxidizing agent.

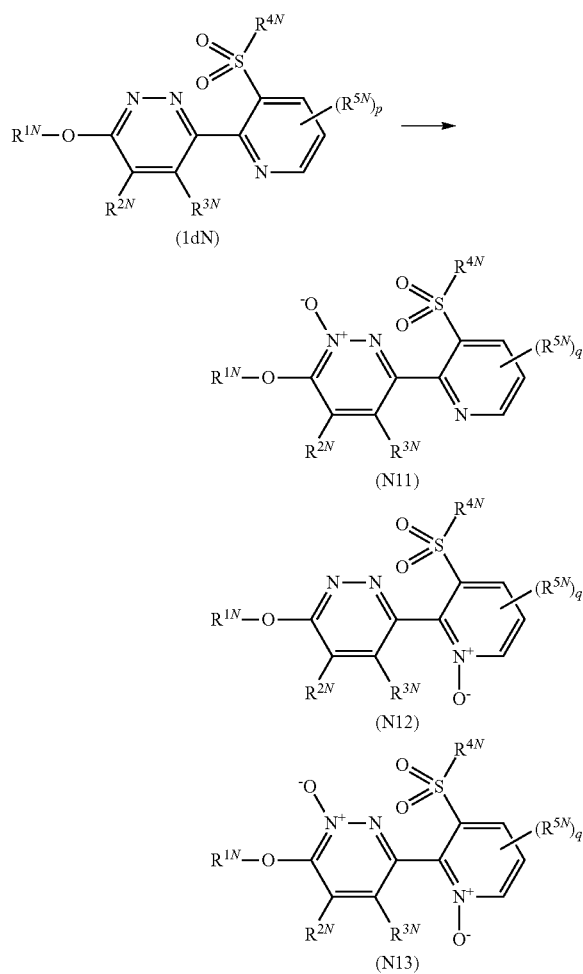

wherein the symbols are the same as those defined above.

The reaction is usually carried out in the presence of a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction includes sodium periodate, m-chloroperoxybenzoic acid (hereinafter, referred to as "mCPBA"), and hydrogen peroxide.

When hydrogen peroxide is used as the oxidizing agent, a catalyst may be added as needed.

Examples of the base to be used in the reaction include sodium carbonate.

Examples of the catalyst to be used in the reaction include tungstic acid, and sodium tungstate.

In the reaction, the oxidizing agent is used usually within a range of 1 to 20 molar ratio(s) as opposed to 1 mole of Present compound (1dN).

In the reaction, the catalyst is used usually within a range of 0.01 to 0.5 molar ratio(s) as opposed to 1 mole of Present compound (1dN).

A reaction temperature in the reaction is usually within a range of −20 to 80° C. A reaction period in the reaction is usually within a range of 0.1 to 24 hours.

When the reaction is completed, the reaction mixture is extracted with an organic solvent, and the organic layer is optionally washed with an aqueous solution of a reducing agent such as sodium sulfite and sodium thiosulfate, and an aqueous solution of a base such as sodium hydrogen carbonate. The resulting organic layer is dried and concentrated to give any one of N-oxide compound (N11), N-oxide compound (N12), or N-oxide compound (N13), or the mixture of N-oxide compounds (N11)-(N13). Any one of the obtained N-oxide compound (N11), N-oxide compound (N12), or N-oxide compound (N13), or the mixture of N-oxide compounds (N11)-(N13) may be further purified with a chromatography, and recrystallization, etc.

Process 14

An N-oxide compound represented by formula (N15) (hereinafter, referred to as "N-oxide compound (N15)") may be prepared by reacting the present compound represented by formula (1eN) (hereinafter, referred to as "Present compound (1eN)") with an oxidizing agent.

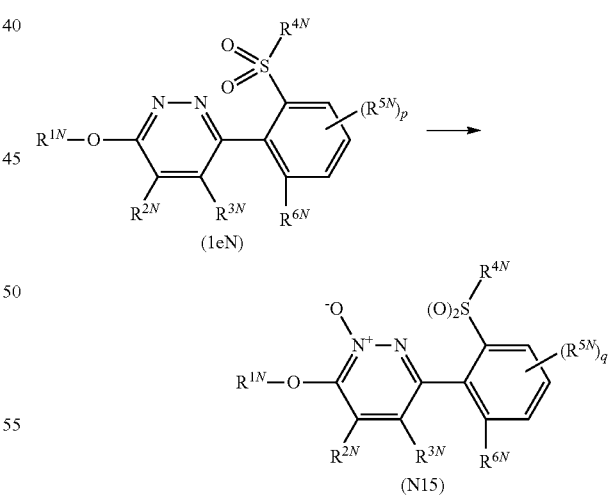

wherein the symbols are the same as those defined above.

The reaction may be carried out according to the method described in Reference Process 1 using Present compound (1eN) instead of Present compound (1dN).

Process 15

The N-oxide compound may be prepared according to a method described as follows.

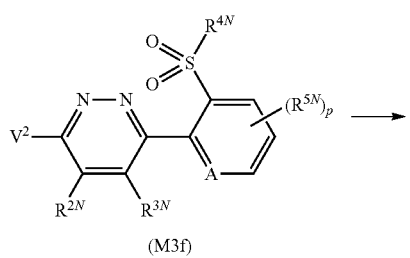

(M3f)

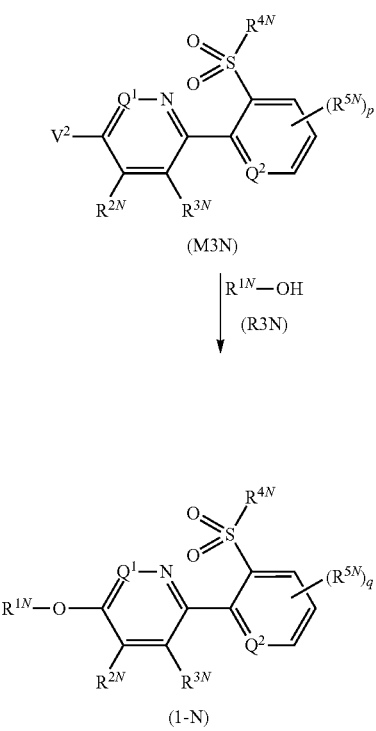

(1-N)

wherein the symbols are the same as those defined above.

First, a process for preparing a compound represented by formula (M3N) (hereinafter, referred to as "Compound (M3N)") is described. Compound (M3N) may be prepared by reacting a compound represented by formula (M3f) (hereinafter, referred to as "Compound (M3f)") with an oxidizing agent.

The reaction may be carried out according to the method described in Reference Process 1 using Compound (M3f) instead of Present compound (1dN).

Next, a process for preparing N-oxide compound (1-N) is described. N-oxide compound (1-N) may be prepared by reacting Compound (M3N) with a compound represented by formula (R3N) (hereinafter, referred to as "Compound (R3N)") in the presence of an oxidizing agent.

The reaction may be carried out according to the method described in Process 4 using Compound (M3N) instead of Compound (M3) and Compound (R3N) instead of Compound (R3).

Next, specific examples of the present compound are shown as follows.

A present compound represented by formula (1-1):

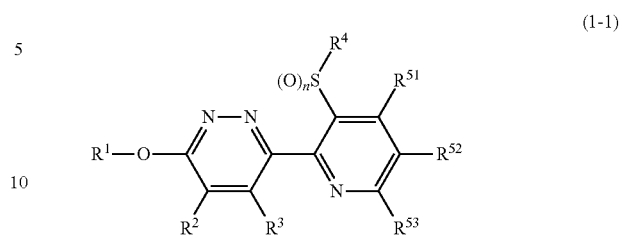

wherein $R^2$ and $R^3$ represent each a hydrogen atom, and $R^1$, $R^4$, n, $R^{51}$, $R^{52}$, and $R^{53}$ represent any one combination indicated in Table 1 to Table 10.

TABLE 1

| $R^1$ | $R^4$ | n | $R^{51}$ | $R^{52}$ | $R^{53}$ |
|---|---|---|---|---|---|
| $CF_2HCH_2$ | $CH_3CH_2$ | 2 | H | H | H |
| $CH_3CF_2$ | $CH_3CH_2$ | 2 | H | H | H |
| $CF_3CH_2$ | $CH_3CH_2$ | 2 | H | H | H |
| $CCl_3CH_2$ | $CH_3CH_2$ | 2 | H | H | H |
| $CF_2HCF_2$ | $CH_3CH_2$ | 2 | H | H | H |
| $CHClFCF_2$ | $CH_3CH_2$ | 2 | H | H | H |
| $CF_3CH_2CH_2$ | $CH_3CH_2$ | 2 | H | H | H |
| $CF_2HCF_2CH_2$ | $CH_3CH_2$ | 2 | H | H | H |
| $CF_3CF_2CH_2$ | $CH_3CH_2$ | 2 | H | H | H |
| $CBrF_2CF_2$ | $CH_3CH_2$ | 2 | H | H | H |
| $CF_3CFHCF_2$ | $CH_3CH_2$ | 2 | H | H | H |
| $CH_3CF_2CH_2$ | $CH_3CH_2$ | 2 | H | H | H |
| $CF_3CH(CH_3)$ | $CH_3CH_2$ | 2 | H | H | H |
| $CF_3C(CH_3)_2$ | $CH_3CH_2$ | 2 | H | H | H |
| $CH(CH_3)_2CH(CF_3)$ | $CH_3CH_2$ | 2 | H | H | H |
| $(CF_3)_2CH$ | $CH_3CH_2$ | 2 | H | H | H |
| $CH_3CH_2CH(CF_3)$ | $CH_3CH_2$ | 2 | H | H | H |
| $CF_3CCl_2CH_2$ | $CH_3CH_2$ | 2 | H | H | H |
| $CF_3CF_2CH(CH_3)$ | $CH_3CH_2$ | 2 | H | H | H |
| $CF_3CF_2CH(CH_2CH_3)$ | $CH_3CH_2$ | 2 | H | H | H |

TABLE 2

| $R^1$ | $R^4$ | n | $R^{51}$ | $R^{52}$ | $R^{53}$ |
|---|---|---|---|---|---|
| $C(CH_3)(CF_3)_2CH_2$ | $CH_3CH_2$ | 2 | H | H | H |
| $CF_3CFHCF_2CH_2$ | $CH_3CH_2$ | 2 | H | H | H |
| $CF_3(CF_2)_2CH_2$ | $CH_3CH_2$ | 2 | H | H | H |
| $CBrF_2CF_2CH_2CH_2$ | $CH_3CH_2$ | 2 | H | H | H |
| $CF_3CFHCF_2CH(CH_3)$ | $CH_3CH_2$ | 2 | H | H | H |
| $CF_3CH=CHCH_2$ | $CH_3CH_2$ | 2 | H | H | H |
| $CF_3(CF_2)_3CH_2$ | $CH_3CH_2$ | 2 | H | H | H |
| $CF_3(CF_2)_4CH_2$ | $CH_3CH_2$ | 2 | H | H | H |
| $CF_3(CF_2)_3CH_2CH_2$ | $CH_3CH_2$ | 2 | H | H | H |
| $CF(CF_3)_2CF_2CF_2CH_2CH_2$ | $CH_3CH_2$ | 2 | H | H | H |
| $CF_2H(CF_2)_3CH_2$ | $CH_3CH_2$ | 2 | H | H | H |
| $CF_2H(CF_2)_5CH_2$ | $CH_3CH_2$ | 2 | H | H | H |
| $CF_3(CF_2)_3CH_2CH_2CH_2$ | $CH_3CH_2$ | 2 | H | H | H |
| $CF_3CF_2(CH_2)_5CH_2$ | $CH_3CH_2$ | 2 | H | H | H |
| $CF_3(CF_2)_5CH_2CH_2$ | $CH_3CH_2$ | 2 | H | H | H |
| $CF_3(CF_2)_3CH_2(CH_2)_4CH_2$ | $CH_3CH_2$ | 2 | H | H | H |
| $CF_3(CF_2)_5CH_2CH_2$ | $CH_3CH_2$ | 2 | H | H | H |
| $CF(CF_3)_2CH_2(CH_2)_4CH_2$ | $CH_3CH_2$ | 2 | H | H | H |

TABLE 3

| $R^1$ | $R^4$ | n | $R^{51}$ | $R^{52}$ | $R^{53}$ |
|---|---|---|---|---|---|
| $CF_3OCFHCF_2$ | $CH_3CH_2$ | 2 | H | H | H |
| $CH_3OCH_2CF_2CH_2$ | $CH_3CH_2$ | 2 | H | H | H |
| $CF_3CH_2OCH_2CF_2CH_2$ | $CH_3CH_2$ | 2 | H | H | H |
| $CH_2FCF_2CH_2$ | $CH_3CH_2$ | 2 | H | H | H |

TABLE 3-continued

| R$^1$ | R$^4$ | n | R$^{51}$ | R$^{52}$ | R$^{53}$ |
|---|---|---|---|---|---|
| CH$_2$ClCF$_2$CH$_2$ | CH$_3$CH$_2$ | 2 | H | H | H |
| CH$_2$BrCF$_2$CH$_2$ | CH$_3$CH$_2$ | 2 | H | H | H |
| CH$_3$OCH$_2$(CF$_2$)$_2$CH$_2$ | CH$_3$CH$_2$ | 2 | H | H | H |
| CF$_3$CH$_2$OCH$_2$(CF$_2$)$_2$CH$_2$ | CH$_3$CH$_2$ | 2 | H | H | H |
| CH$_2$F(CF$_2$)$_2$CH$_2$ | CH$_3$CH$_2$ | 2 | H | H | H |
| CH$_2$Cl(CF$_2$)$_2$CH$_2$ | CH$_3$CH$_2$ | 2 | H | H | H |
| CH$_2$Br(CF$_2$)$_2$CH$_2$ | CH$_3$CH$_2$ | 2 | H | H | H |
| CH$_3$OCH$_2$(CF$_2$)$_3$CH$_2$ | CH$_3$CH$_2$ | 2 | H | H | H |
| CF$_3$CH$_2$OCH$_2$(CF$_2$)$_3$CH$_2$ | CH$_3$CH$_2$ | 2 | H | H | H |
| CH$_3$OCH$_2$(CF$_2$)$_3$CH$_2$ | CH$_3$CH$_2$ | 2 | H | H | H |
| CF$_3$CH$_2$OCH$_2$(CF$_2$)$_3$CH$_2$ | CH$_3$CH$_2$ | 2 | H | H | H |
| CH$_2$F(CF$_2$)$_3$CH$_2$ | CH$_3$CH$_2$ | 2 | H | H | H |
| CH$_2$Cl(CF$_2$)$_3$CH$_2$ | CH$_3$CH$_2$ | 2 | H | H | H |
| CH$_2$Br(CF$_2$)$_3$CH$_2$ | CH$_3$CH$_2$ | 2 | H | H | H |
| CH$_3$OCH$_2$(CF$_2$)$_4$CH$_2$ | CH$_3$CH$_2$ | 2 | H | H | H |
| CF$_3$CH$_2$OCH$_2$(CF$_2$)$_4$CH$_2$ | CH$_3$CH$_2$ | 2 | H | H | H |

TABLE 4

| R$^1$ | R$^4$ | n | R$^{51}$ | R$^{52}$ | R$^{53}$ |
|---|---|---|---|---|---|
| CH$_2$F(CF$_2$)$_4$CH$_2$ | CH$_3$CH$_2$ | 2 | H | H | H |
| CH$_2$Cl(CF$_2$)$_4$CH$_2$ | CH$_3$CH$_2$ | 2 | H | H | H |
| CH$_2$Br(CF$_2$)$_4$CH$_2$ | CH$_3$CH$_2$ | 2 | H | H | H |
| CF$_3$CF$_2$OCFHCF$_2$ | CH$_3$CH$_2$ | 2 | H | H | H |
| CF$_3$CF$_2$CF$_2$OCFHCF$_2$ | CH$_3$CH$_2$ | 2 | H | H | H |
| CF$_3$CF$_2$CF$_2$OCF(CF$_3$)CH$_2$ | CH$_3$CH$_2$ | 2 | H | H | H |
| CF$_3$CH$_2$OCH$_2$CH$_2$ | CH$_3$CH$_2$ | 2 | H | H | H |
| CH$_3$SCH$_2$CF$_2$CH$_2$ | CH$_3$CH$_2$ | 2 | H | H | H |
| CH$_3$S(O)CH$_2$CF$_2$CH$_2$ | CH$_3$CH$_2$ | 2 | H | H | H |
| CH$_3$S(O)$_2$CH$_2$CF$_2$CH$_2$ | CH$_3$CH$_2$ | 2 | H | H | H |
| CF$_3$CH$_2$SCH$_2$CF$_2$CH$_2$ | CH$_3$CH$_2$ | 2 | H | H | H |
| CF$_3$CH$_2$S(O)CH$_2$CF$_2$CH$_2$ | CH$_3$CH$_2$ | 2 | H | H | H |
| CF$_3$CH$_2$S(O)$_2$CH$_2$CF$_2$CH$_2$ | CH$_3$CH$_2$ | 2 | H | H | H |
| CF$_3$SCH$_2$CF$_2$CH$_2$ | CH$_3$CH$_2$ | 2 | H | H | H |
| CF$_3$S(O)CH$_2$CF$_2$CH$_2$ | CH$_3$CH$_2$ | 2 | H | H | H |
| CF$_3$S(O)$_2$CH$_2$CF$_2$CH$_2$ | CH$_3$CH$_2$ | 2 | H | H | H |
| CF$_3$SCH$_2$(CF$_2$)$_2$CH$_2$ | CH$_3$CH$_2$ | 2 | H | H | H |
| CF$_3$S(O)CH$_2$(CF$_2$)$_2$CH$_2$ | CH$_3$CH$_2$ | 2 | H | H | H |
| CF$_3$S(O)$_2$CH$_2$(CF$_2$)$_2$CH$_2$ | CH$_3$CH$_2$ | 2 | H | H | H |
| CF$_3$SCH$_2$(CF$_2$)$_3$CH$_2$ | CH$_3$CH$_2$ | 2 | H | H | H |

TABLE 5

| R$^1$ | R$^4$ | n | R$^{51}$ | R$^{52}$ | R$^{53}$ |
|---|---|---|---|---|---|
| CF$_3$S(O)CH$_2$(CF$_2$)$_3$CH$_2$ | CH$_3$CH$_2$ | 2 | H | H | H |
| CF$_3$S(O)$_2$CH$_2$(CF$_2$)$_3$CH$_2$ | CH$_3$CH$_2$ | 2 | H | H | H |
| CF$_3$SCH$_2$(CF$_2$)$_4$CH$_2$ | CH$_3$CH$_2$ | 2 | H | H | H |
| CF$_3$S(O)CH$_2$(CF$_2$)$_4$CH$_2$ | CH$_3$CH$_2$ | 2 | H | H | H |
| CF$_3$S(O)$_2$CH$_2$(CF$_2$)$_4$CH$_2$ | CH$_3$CH$_2$ | 2 | H | H | H |
| CF$_3$CH$_2$SCH$_2$CH$_2$ | CH$_3$CH$_2$ | 2 | H | H | H |
| CF$_3$CH$_2$S(O)CH$_2$CH$_2$ | CH$_3$CH$_2$ | 2 | H | H | H |
| CF$_3$CH$_2$S(O)$_2$CH$_2$CH$_2$ | CH$_3$CH$_2$ | 2 | H | H | H |
| CF$_3$SCH$_2$CH$_2$ | CH$_3$CH$_2$ | 2 | H | H | H |
| CF$_3$S(O)CH$_2$CH$_2$ | CH$_3$CH$_2$ | 2 | H | H | H |
| CF$_3$S(O)$_2$CH$_2$CH$_2$ | CH$_3$CH$_2$ | 2 | H | H | H |

TABLE 6

| R$^1$ | R$^4$ | n | R$^{51}$ | R$^{52}$ | R$^{53}$ |
|---|---|---|---|---|---|
| CF$_2$HCH$_2$ | CH$_3$CH$_2$ | 2 | H | CF$_3$ | H |
| CH$_3$CF$_2$ | CH$_3$CH$_2$ | 2 | H | CF$_3$ | H |
| CF$_3$CH$_2$ | CH$_3$CH$_2$ | 2 | H | CF$_3$ | H |
| CCl$_3$CH$_2$ | CH$_3$CH$_2$ | 2 | H | CF$_3$ | H |
| CF$_2$HCF$_2$ | CH$_3$CH$_2$ | 2 | H | CF$_3$ | H |
| CHClFCF$_2$ | CH$_3$CH$_2$ | 2 | H | CF$_3$ | H |
| CF$_3$CH$_2$CH$_2$ | CH$_3$CH$_2$ | 2 | H | CF$_3$ | H |
| CF$_2$HCF$_2$CH$_2$ | CH$_3$CH$_2$ | 2 | H | CF$_3$ | H |
| CF$_3$CF$_2$CH$_2$ | CH$_3$CH$_2$ | 2 | H | CF$_3$ | H |

TABLE 6-continued

| R$^1$ | R$^4$ | n | R$^{51}$ | R$^{52}$ | R$^{53}$ |
|---|---|---|---|---|---|
| CBrF$_2$CF$_2$ | CH$_3$CH$_2$ | 2 | H | CF$_3$ | H |
| CF$_3$CFHCF$_2$ | CH$_3$CH$_2$ | 2 | H | CF$_3$ | H |
| CH$_3$CF$_2$CH$_2$ | CH$_3$CH$_2$ | 2 | H | CF$_3$ | H |
| CF$_3$CH(CH$_3$) | CH$_3$CH$_2$ | 2 | H | CF$_3$ | H |
| CF$_3$C(CH$_3$)$_2$ | CH$_3$CH$_2$ | 2 | H | CF$_3$ | H |
| CH(CH$_3$)$_2$CH(CF$_3$) | CH$_3$CH$_2$ | 2 | H | CF$_3$ | H |
| (CF$_3$)$_2$CH | CH$_3$CH$_2$ | 2 | H | CF$_3$ | H |
| CH$_3$CH$_2$CH(CF$_3$) | CH$_3$CH$_2$ | 2 | H | CF$_3$ | H |
| CF$_3$CCl$_2$CH$_2$ | CH$_3$CH$_2$ | 2 | H | CF$_3$ | H |
| CF$_3$CF$_2$CH(CH$_3$) | CH$_3$CH$_2$ | 2 | H | CF$_3$ | H |
| CF$_3$CF$_2$CH(CH$_2$CH$_3$) | CH$_3$CH$_2$ | 2 | H | CF$_3$ | H |

TABLE 7

| R$^1$ | R$^4$ | n | R$^{51}$ | R$^{52}$ | R$^{53}$ |
|---|---|---|---|---|---|
| C(CH$_3$)(CF$_3$)$_2$CH$_2$ | CH$_3$CH$_2$ | 2 | H | CF$_3$ | H |
| CF$_3$CFHCF$_2$CH$_2$ | CH$_3$CH$_2$ | 2 | H | CF$_3$ | H |
| CF$_3$(CF$_2$)$_2$CH$_2$ | CH$_3$CH$_2$ | 2 | H | CF$_3$ | H |
| CBrF$_2$CF$_2$CH$_2$CH$_2$ | CH$_3$CH$_2$ | 2 | H | CF$_3$ | H |
| CF$_3$CFHCF$_2$CH(CH$_3$) | CH$_3$CH$_2$ | 2 | H | CF$_3$ | H |
| CF$_3$CH=CHCH$_2$ | CH$_3$CH$_2$ | 2 | H | CF$_3$ | H |
| CF$_3$(CF$_2$)$_3$CH$_2$ | CH$_3$CH$_2$ | 2 | H | CF$_3$ | H |
| CF$_3$(CF$_2$)$_4$CH$_2$ | CH$_3$CH$_2$ | 2 | H | CF$_3$ | H |
| CF$_3$(CF$_2$)$_3$CH$_2$CH$_2$ | CH$_3$CH$_2$ | 2 | H | CF$_3$ | H |
| CF(CF$_3$)$_2$CF$_2$CF$_2$CH$_2$CH$_2$ | CH$_3$CH$_2$ | 2 | H | CF$_3$ | H |
| CF$_2$H(CF$_2$)$_3$CH$_2$ | CH$_3$CH$_2$ | 2 | H | CF$_3$ | H |
| CF$_2$H(CF$_2$)$_5$CH$_2$ | CH$_3$CH$_2$ | 2 | H | CF$_3$ | H |
| CF$_3$(CF$_2$)$_3$CH$_2$CH$_2$CH$_2$ | CH$_3$CH$_2$ | 2 | H | CF$_3$ | H |
| CF$_3$CF$_2$(CH$_2$)$_5$CH$_2$ | CH$_3$CH$_2$ | 2 | H | CF$_3$ | H |
| CF$_3$(CF$_2$)$_5$CH$_2$CH$_2$CH$_2$ | CH$_3$CH$_2$ | 2 | H | CF$_3$ | H |
| CF$_3$(CF$_2$)$_3$CH$_2$(CH$_2$)$_4$CH$_2$ | CH$_3$CH$_2$ | 2 | H | CF$_3$ | H |
| CF$_3$(CF$_2$)$_5$CH$_2$CH$_2$ | CH$_3$CH$_2$ | 2 | H | CF$_3$ | H |
| CF(CF$_3$)$_2$CH$_2$(CH$_2$)$_4$CH$_2$ | CH$_3$CH$_2$ | 2 | H | CF$_3$ | H |
| CF$_3$OCFHCF$_2$ | CH$_3$CH$_2$ | 2 | H | CF$_3$ | H |
| CH$_3$OCH$_2$CF$_2$CH$_2$ | CH$_3$CH$_2$ | 2 | H | CF$_3$ | H |

TABLE 8

| R$^1$ | R$^4$ | n | R$^{51}$ | R$^{52}$ | R$^{53}$ |
|---|---|---|---|---|---|
| CF$_3$CH$_2$OCH$_2$CF$_2$CH$_2$ | CH$_3$CH$_2$ | 2 | H | CF$_3$ | H |
| CH$_2$FCF$_2$CH$_2$ | CH$_3$CH$_2$ | 2 | H | CF$_3$ | H |
| CH$_2$ClCF$_2$CH$_2$ | CH$_3$CH$_2$ | 2 | H | CF$_3$ | H |
| CH$_2$BrCF$_2$CH$_2$ | CH$_3$CH$_2$ | 2 | H | CF$_3$ | H |
| CH$_3$OCH$_2$(CF$_2$)$_2$CH$_2$ | CH$_3$CH$_2$ | 2 | H | CF$_3$ | H |
| CF$_3$CH$_2$OCH$_2$(CF$_2$)$_2$CH$_2$ | CH$_3$CH$_2$ | 2 | H | CF$_3$ | H |
| CH$_2$F(CF$_2$)$_2$CH$_2$ | CH$_3$CH$_2$ | 2 | H | CF$_3$ | H |
| CH$_2$Cl(CF$_2$)$_2$CH$_2$ | CH$_3$CH$_2$ | 2 | H | CF$_3$ | H |
| CH$_2$Br(CF$_2$)$_2$CH$_2$ | CH$_3$CH$_2$ | 2 | H | CF$_3$ | H |
| CH$_3$OCH$_2$(CF$_2$)$_3$CH$_2$ | CH$_3$CH$_2$ | 2 | H | CF$_3$ | H |
| CF$_3$CH$_2$OCH$_2$(CF$_2$)$_3$CH$_2$ | CH$_3$CH$_2$ | 2 | H | CF$_3$ | H |
| CH$_3$OCH$_2$(CF$_2$)$_3$CH$_2$ | CH$_3$CH$_2$ | 2 | H | CF$_3$ | H |
| CF$_3$CH$_2$OCH$_2$(CF$_2$)$_3$CH$_2$ | CH$_3$CH$_2$ | 2 | H | CF$_3$ | H |
| CH$_2$F(CF$_2$)$_3$CH$_2$ | CH$_3$CH$_2$ | 2 | H | CF$_3$ | H |
| CH$_2$Cl(CF$_2$)$_3$CH$_2$ | CH$_3$CH$_2$ | 2 | H | CF$_3$ | H |
| CH$_2$Br(CF$_2$)$_3$CH$_2$ | CH$_3$CH$_2$ | 2 | H | CF$_3$ | H |
| CH$_3$OCH$_2$(CF$_2$)$_4$CH$_2$ | CH$_3$CH$_2$ | 2 | H | CF$_3$ | H |
| CF$_3$CH$_2$OCH$_2$(CF$_2$)$_4$CH$_2$ | CH$_3$CH$_2$ | 2 | H | CF$_3$ | H |
| CH$_2$F(CF$_2$)$_4$CH$_2$ | CH$_3$CH$_2$ | 2 | H | CF$_3$ | H |
| CH$_2$Cl(CF$_2$)$_4$CH$_2$ | CH$_3$CH$_2$ | 2 | H | CF$_3$ | H |

TABLE 9

| R$^1$ | R$^4$ | n | R$^{51}$ | R$^{52}$ | R$^{53}$ |
|---|---|---|---|---|---|
| CH$_2$Br(CF$_2$)$_4$CH$_2$ | CH$_3$CH$_2$ | 2 | H | CF$_3$ | H |
| CF$_3$CF$_2$OCFHCF$_2$ | CH$_3$CH$_2$ | 2 | H | CF$_3$ | H |
| CF$_3$CF$_2$CF$_2$OCFHCF$_2$ | CH$_3$CH$_2$ | 2 | H | CF$_3$ | H |
| CF$_3$CF$_2$CF$_2$OCF(CF$_3$)CH$_2$ | CH$_3$CH$_2$ | 2 | H | CF$_3$ | H |
| CF$_3$CH$_2$OCH$_2$CH$_2$ | CH$_3$CH$_2$ | 2 | H | CF$_3$ | H |

TABLE 9-continued

| R$^1$ | R$^4$ | n | R$^{51}$ | R$^{52}$ | R$^{53}$ |
|---|---|---|---|---|---|
| CH$_3$SCH$_2$CF$_2$CH$_2$ | CH$_3$CH$_2$ | 2 | H | CF$_3$ | H |
| CH$_3$S(O)CH$_2$CF$_2$CH$_2$ | CH$_3$CH$_2$ | 2 | H | CF$_3$ | H |
| CH$_3$S(O)$_2$CH$_2$CF$_2$CH$_2$ | CH$_3$CH$_2$ | 2 | H | CF$_3$ | H |
| CF$_3$CH$_2$SCH$_2$CF$_2$CH$_2$ | CH$_3$CH$_2$ | 2 | H | CF$_3$ | H |
| CF$_3$CH$_2$S(O)CH$_2$CF$_2$CH$_2$ | CH$_3$CH$_2$ | 2 | H | CF$_3$ | H |
| CF$_3$CH$_2$S(O)$_2$CH$_2$CF$_2$CH$_2$ | CH$_3$CH$_2$ | 2 | H | CF$_3$ | H |
| CF$_3$SCH$_2$CF$_2$CH$_2$ | CH$_3$CH$_2$ | 2 | H | CF$_3$ | H |
| CF$_3$S(O)CH$_2$CF$_2$CH$_2$ | CH$_3$CH$_2$ | 2 | H | CF$_3$ | H |
| CF$_3$S(O)$_2$CH$_2$CF$_2$CH$_2$ | CH$_3$CH$_2$ | 2 | H | CF$_3$ | H |
| CF$_3$SCH$_2$(CF$_2$)$_2$CH$_2$ | CH$_3$CH$_2$ | 2 | H | CF$_3$ | H |
| CF$_3$S(O)CH$_2$(CF$_2$)$_2$CH$_2$ | CH$_3$CH$_2$ | 2 | H | CF$_3$ | H |
| CF$_3$S(O)$_2$CH$_2$(CF$_2$)$_2$CH$_2$ | CH$_3$CH$_2$ | 2 | H | CF$_3$ | H |
| CF$_3$SCH$_2$(CF$_2$)$_3$CH$_2$ | CH$_3$CH$_2$ | 2 | H | CF$_3$ | H |
| CF$_3$S(O)CH$_2$(CF$_2$)$_3$CH$_2$ | CH$_3$CH$_2$ | 2 | H | CF$_3$ | H |
| CF$_3$S(O)$_2$CH$_2$(CF$_2$)$_3$CH$_2$ | CH$_3$CH$_2$ | 2 | H | CF$_3$ | H |

TABLE 10

| R$^1$ | R$^4$ | n | R$^{51}$ | R$^{52}$ | R$^{53}$ |
|---|---|---|---|---|---|
| CF$_3$SCH$_2$(CF$_2$)$_4$CH$_2$ | CH$_3$CH$_2$ | 2 | H | CF$_3$ | H |
| CF$_3$S(O)CH$_2$(CF$_2$)$_4$CH$_2$ | CH$_3$CH$_2$ | 2 | H | CF$_3$ | H |
| CF$_3$S(O)$_2$CH$_2$(CF$_2$)$_4$CH$_2$ | CH$_3$CH$_2$ | 2 | H | CF$_3$ | H |
| CF$_3$CH$_2$SCH$_2$CH$_2$ | CH$_3$CH$_2$ | 2 | H | CF$_3$ | H |
| CF$_3$CH$_2$S(O)CH$_2$CH$_2$ | CH$_3$CH$_2$ | 2 | H | CF$_3$ | H |
| CF$_3$CH$_2$S(O)$_2$CH$_2$CH$_2$ | CH$_3$CH$_2$ | 2 | H | CF$_3$ | H |
| CF$_3$SCH$_2$CH$_2$ | CH$_3$CH$_2$ | 2 | H | CF$_3$ | H |
| CF$_3$S(O)CH$_2$CH$_2$ | CH$_3$CH$_2$ | 2 | H | CF$_3$ | H |
| CF$_3$S(O)$_2$CH$_2$CH$_2$ | CH$_3$CH$_2$ | 2 | H | CF$_3$ | H |

The present compound represented by formula (1-1) wherein R$^2$ represents a methyl group, R$^3$ represents a hydrogen group, and R$^1$, R$^4$, n, R$^{51}$, R$^{52}$, and R$^{53}$ represent any combination indicated in Table 1 to Table 10.

The present compound represented by formula (1-1) wherein R$^2$ represents a trifluoromethyl group, R$^3$ represents a hydrogen group, and R$^1$, R$^4$, n, R$^{51}$, R$^{52}$, and R$^{53}$ represent any combination indicated in Table 1 to Table 10.

The present compound represented by formula (1-1) wherein R$^2$ represents a chlorine group, R$^3$ represents a hydrogen group, and R$^1$, R$^4$, n, R$^{51}$, R$^{52}$, and R$^{53}$ represent any combination indicated in Table 1 to Table 10.

The present compound represented by formula (1-1) wherein R$^2$ represents a fluorine group, R$^3$ represents a hydrogen group, and R$^1$, R$^4$, n, R$^{51}$, R$^{52}$, and R$^{53}$ represent any combination indicated in [Table 1 to Table 10.

The present compound represented by formula (1-1) wherein R$^2$ represents a hydrogen group, R$^3$ represents a methyl group, and R$^1$, R$^4$, n, R$^{51}$, R$^{52}$, and R$^{53}$ represent any combination indicated in Table 1 to Table 10.

The present compound represented by formula (1-1) wherein R$^2$ represents a chlorine group, R$^3$ represents a trifluoromethyl group, and R$^1$, R$^4$, n, R$^{51}$, R$^{52}$, and R$^{53}$ represent any combination indicated in Table 1 to Table 10.

The present compound represented by formula (1-1) wherein R$^2$ represents a hydrogen group, R$^3$ represents a chlorine group, and R$^1$, R$^4$, n, R$^{51}$, R$^{52}$, and R$^{53}$ represent any combination indicated in Table 1 to Table 10.

The present compound represented by formula (1-1) wherein R$^2$ represents a hydrogen group, R$^3$ represents a fluorine group, R$^1$, R$^4$, n, R$^{51}$, R$^{52}$, and R$^{53}$ represent any combination indicated in Table 1 to Table 10.

A present compound represented by formula (1-2):

$$(1\text{-}2)$$

wherein R$^2$ and R$^3$ represent each a hydrogen atom, R$^6$ represents a hydrogen, and R$^1$, R$^4$, n, R$^{51}$, R$^{52}$, and R$^{53}$ represent any one combination indicated in Table 1 to Table 10.

The present compound represented by formula (1-2) wherein R$^2$ represents a methyl group, R$^3$ represents a hydrogen group, R$^6$ represents a hydrogen, and R$^1$, R$^4$, n, R$^{51}$, R$^{52}$, and R$^{53}$ represent any one combination indicated in Table 1 to Table 10.

The present compound represented by formula (1-2) wherein R$^2$ represents a trifluoromethyl group, R$^3$ represents a hydrogen group, R$^6$ represents a hydrogen, and R$^1$, R$^4$, n, R$^{51}$, R$^{52}$, and R$^{53}$ represent any one combination indicated in Table 1 to Table 10.

The present compound represented by formula (1-2) wherein R$^2$ represents a chlorine group, R$^3$ represents a hydrogen group, R$^6$ represents a hydrogen, and R$^1$, R$^4$, n, R$^{51}$, R$^{52}$, and R$^{53}$ represent any one combination indicated in Table 1 to Table 10.

The present compound represented by formula (1-2) wherein R$^2$ represents a fluorine group, R$^3$ represents a hydrogen group, R$^6$ represents a hydrogen, and R$^1$, R$^4$, n, R$^{51}$, R$^{52}$, and R$^{53}$ represent any one combination indicated in Table 1 to Table 10.

The present compound represented by formula (1-2) wherein R$^2$ represents a hydrogen group, R$^3$ represents a methyl group, R$^6$ represents a hydrogen, and R$^1$, R$^4$, n, R$^{51}$, R$^{52}$, and R$^{53}$ represent any one combination indicated in Table 1 to Table 10.

The present compound represented by formula (1-2) wherein R$^2$ represents a chlorine group, R$^3$ represents a trifluoromethyl group, R$^6$ represents a hydrogen, and R$^1$, R$^4$, n, R$^{51}$, R$^{52}$, and R$^{53}$ represent any one combination indicated in Table 1 to Table 10.

The present compound represented by formula (1-2) wherein R$^2$ represents a hydrogen group, R$^3$ represents a chlorine group, R$^6$ represents a hydrogen, and R$^1$, R$^4$, n, R$^{51}$, R$^{52}$, and R$^{53}$ represent any one combination indicated in Table 1 to Table 10.

The present compound represented by formula (1-2) wherein R$^2$ represents a hydrogen group, R$^3$ represents a fluorine group, R$^6$ represents a hydrogen, and R$^1$, R$^4$, n, R$^{51}$, R$^{52}$, and R represent any one combination indicated in Table 1 to Table 10.

The present compound represented by formula (1-2) wherein R$^2$ represents a methyl group, R$^3$ represents a hydrogen group, R$^6$ represents a fluorine atom, and R$^1$, R$^4$, n, R$^{51}$, R$^{52}$, and R$^{53}$ represent any one combination indicated in Table 1 to Table 10.

The present compound represented by formula (1-2) wherein R$^2$ represents a trifluoromethyl group, R$^3$ represents a hydrogen group, R$^6$ represents a fluorine atom, and R$^1$, R$^4$, n, R$^{51}$, R$^{52}$, and R$^{53}$ represent any one combination indicated in Table 1 to Table 10.

The present compound represented by formula (1-2) wherein $R^2$ represents a chlorine group, $R^3$ represents a hydrogen group, $R^6$ represents a fluorine atom, and $R^1$, $R^4$, n, $R^{51}$, $R^{52}$, and $R^{53}$ represent any one combination indicated in Table 1 to Table 10.

The present compound represented by formula (1-2) wherein $R^2$ represents a fluorine group, $R^3$ represents a hydrogen group, $R^6$ represents a fluorine atom, and $R^1$, $R^4$, n, $R^{51}$, $R^{52}$, and $R^{53}$ represent any one combination indicated in Table 1 to Table 10.

The present compound represented by formula (1-2) wherein $R^2$ represents a hydrogen atom, $R^3$ represents a methyl group, $R^6$ represents a fluorine, and $R^1$, $R^4$, n, $R^{51}$, $R^{52}$, and $R^{53}$ represent any one combination indicated in Table 1 to Table 10.

The present compound represented by formula (1-2) wherein $R^2$ represents a chlorine group, $R^3$ represents a trifluoromethyl group, $R^6$ represents a fluorine atom, and $R^1$, $R^4$, n, $R^{51}$, $R^{52}$, and $R^{53}$ represent any one combination indicated in Table 1 to Table 10.

The present compound represented by formula (1-2) wherein $R^2$ represents a hydrogen group, $R^3$ represents a chlorine group, $R^6$ represents a fluorine atom, and $R^1$, $R^4$, n, $R^{51}$, $R^{52}$, and $R^{53}$ represent any one combination indicated in Table 1 to Table 10.

The present compound represented by formula (1-2) wherein $R^2$ represents a hydrogen group, $R^3$ represents a fluorine group, $R^6$ represents a fluorine atom, and $R^1$, $R^4$, n, $R^{51}$, $R^{52}$, and $R^{53}$ represent any one combination indicated in Table 1 to Table 10.

Next, specific examples of the N-oxide compound are shown as follows.

A present compound represented by formula (1-N11):

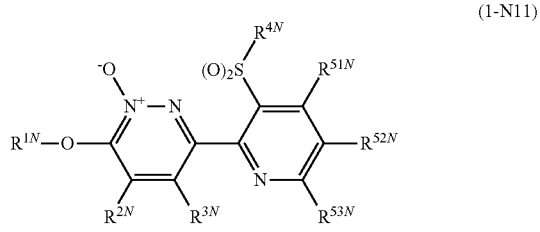

(1-N11)

wherein $R^{2N}$ and $R^{3N}$ represent each a hydrogen atom, and $R^{1N}$, $R^{4N}$, $R^{51N}$, $R^{52N}$, and $R^{53N}$ represent any one combination indicated in Table 11 to Table 16.

TABLE 11

| $R^{1N}$ | $R^{4N}$ | $R^{51N}$ | $R^{52N}$ | $R^{53N}$ |
|---|---|---|---|---|
| $CF_2HCH_2$ | $CH_3CH_2$ | H | H | H |
| $CH_3CF_2$ | $CH_3CH_2$ | H | H | H |
| $CF_3CH_2$ | $CH_3CH_2$ | H | H | H |
| $CCl_3CH_2$ | $CH_3CH_2$ | H | H | H |
| $CF_2HCF_2$ | $CH_3CH_2$ | H | H | H |
| $CHClFCF_2$ | $CH_3CH_2$ | H | H | H |
| $CF_3CH_2CH_2$ | $CH_3CH_2$ | H | H | H |
| $CF_2HCF_2CH_2$ | $CH_3CH_2$ | H | H | H |
| $CF_3CF_2CH_2$ | $CH_3CH_2$ | H | H | H |
| $CBrF_2CF_2$ | $CH_3CH_2$ | H | H | H |
| $CF_3CFHCF_2$ | $CH_3CH_2$ | H | H | H |
| $CH_3CF_2CH_2$ | $CH_3CH_2$ | H | H | H |
| $CF_3CH(CH_3)$ | $CH_3CH_2$ | H | H | H |
| $CF_3C(CH_3)_2$ | $CH_3CH_2$ | H | H | H |
| $CH(CH_3)_2CH(CF_3)$ | $CH_3CH_2$ | H | H | H |
| $(CF_3)_2CH$ | $CH_3CH_2$ | H | H | H |

TABLE 11-continued

| $R^{1N}$ | $R^{4N}$ | $R^{51N}$ | $R^{52N}$ | $R^{53N}$ |
|---|---|---|---|---|
| $CH_3CH_2CH(CF_3)$ | $CH_3CH_2$ | H | H | H |
| $CF_3CCl_2CH_2$ | $CH_3CH_2$ | H | H | H |
| $CF_3CF_2CH(CH_3)$ | $CH_3CH_2$ | H | H | H |
| $CF_3CF_2CH(CH_2CH_3)$ | $CH_3CH_2$ | H | H | H |

TABLE 12

| $R^{1N}$ | $R^{4N}$ | $R^{51N}$ | $R^{52N}$ | $R^{53N}$ |
|---|---|---|---|---|
| $C(CH_3)(CF_3)_2CH_2$ | $CH_3CH_2$ | H | H | H |
| $CF_3CFHCF_2CH_2$ | $CH_3CH_2$ | H | H | H |
| $CF_3(CF_2)_2CH_2$ | $CH_3CH_2$ | H | H | H |
| $CBrF_2CF_2CH_2CH_2$ | $CH_3CH_2$ | H | H | H |
| $CF_3CFHCF_2CH(CH_3)$ | $CH_3CH_2$ | H | H | H |
| $CF_3(CF_2)_3CH_2$ | $CH_3CH_2$ | H | H | H |
| $CF_3(CF_2)_4CH_2$ | $CH_3CH_2$ | H | H | H |
| $CF_3(CF_2)_3CH_2CH_2$ | $CH_3CH_2$ | H | H | H |
| $CF(CF_3)_2CF_2CF_2CH_2CH_2$ | $CH_3CH_2$ | H | H | H |
| $CF_2H(CF_2)_3CH_2$ | $CH_3CH_2$ | H | H | H |
| $CF_2H(CF_2)_5CH_2$ | $CH_3CH_2$ | H | H | H |
| $CF_3(CF_2)_3CH_2CH_2CH_2$ | $CH_3CH_2$ | H | H | H |
| $CF_3CF_2(CH_2)_5CH_2$ | $CH_3CH_2$ | H | H | H |
| $CF_3(CF_2)_5CH_2CH_2CH_2$ | $CH_3CH_2$ | H | H | H |
| $CF_3(CF_2)_3CH_2(CH_2)_4CH_2$ | $CH_3CH_2$ | H | H | H |
| $CF_3(CF_2)_5CH_2CH_2$ | $CH_3CH_2$ | H | H | H |
| $CF(CF_3)_2CH_2(CH_2)_4CH_2$ | $CH_3CH_2$ | H | H | H |
| $CH_2FCF_2CH_2$ | $CH_3CH_2$ | H | H | H |
| $CH_2ClCF_2CH_2$ | $CH_3CH_2$ | H | H | H |
| $CH_2BrCF_2CH_2$ | $CH_3CH_2$ | H | H | H |

TABLE 13

| $R^{1N}$ | $R^{4N}$ | $R^{51N}$ | $R^{52N}$ | $R^{53N}$ |
|---|---|---|---|---|
| $CH_2F(CF_2)_2CH_2$ | $CH_3CH_2$ | H | H | H |
| $CH_2Cl(CF_2)_2CH_2$ | $CH_3CH_2$ | H | H | H |
| $CH_2Br(CF_2)_2CH_2$ | $CH_3CH_2$ | H | H | H |
| $CH_2F(CF_2)_3CH_2$ | $CH_3CH_2$ | H | H | H |
| $CH_2Cl(CF_2)_3CH_2$ | $CH_3CH_2$ | H | H | H |
| $CH_2Br(CF_2)_3CH_2$ | $CH_3CH_2$ | H | H | H |
| $CH_2F(CF_2)_4CH_2$ | $CH_3CH_2$ | H | H | H |
| $CH_2Cl(CF_2)_4CH_2$ | $CH_3CH_2$ | H | H | H |
| $CH_2Br(CF_2)_4CH_2$ | $CH_3CH_2$ | H | H | H |

TABLE 14

| $R^{1N}$ | $R^{4N}$ | $R^{51N}$ | $R^{52N}$ | $R^{53N}$ |
|---|---|---|---|---|
| $CF_2HCH_2$ | $CH_3CH_2$ | H | $CF_3$ | H |
| $CH_3CF_2$ | $CH_3CH_2$ | H | $CF_3$ | H |
| $CF_3CH_2$ | $CH_3CH_2$ | H | $CF_3$ | H |
| $CCl_3CH_2$ | $CH_3CH_2$ | H | $CF_3$ | H |
| $CF_2HCF_2$ | $CH_3CH_2$ | H | $CF_3$ | H |
| $CHClFCF_2$ | $CH_3CH_2$ | H | $CF_3$ | H |
| $CF_3CH_2CH_2$ | $CH_3CH_2$ | H | $CF_3$ | H |
| $CF_2HCF_2CH_2$ | $CH_3CH_2$ | H | $CF_3$ | H |
| $CF_3CF_2CH_2$ | $CH_3CH_2$ | H | $CF_3$ | H |
| $CBrF_2CF_2$ | $CH_3CH_2$ | H | $CF_3$ | H |
| $CF_3CFHCF_2$ | $CH_3CH_2$ | H | $CF_3$ | H |
| $CH_3CF_2CH_2$ | $CH_3CH_2$ | H | $CF_3$ | H |
| $CF_3CH(CH_3)$ | $CH_3CH_2$ | H | $CF_3$ | H |
| $CF_3C(CH_3)_2$ | $CH_3CH_2$ | H | $CF_3$ | H |
| $CH(CH_3)_2CH(CF_3)$ | $CH_3CH_2$ | H | $CF_3$ | H |
| $(CF_3)_2CH$ | $CH_3CH_2$ | H | $CF_3$ | H |
| $CH_3CH_2CH(CF_3)$ | $CH_3CH_2$ | H | $CF_3$ | H |
| $CF_3CCl_2CH_2$ | $CH_3CH_2$ | H | $CF_3$ | H |
| $CF_3CF_2CH(CH_3)$ | $CH_3CH_2$ | H | $CF_3$ | H |
| $CF_3CF_2CH(CH_2CH_3)$ | $CH_3CH_2$ | H | $CF_3$ | H |

TABLE 15

| $R^{1N}$ | $R^{4N}$ | $R^{51N}$ | $R^{52N}$ | $R^{53N}$ |
|---|---|---|---|---|
| C(CH$_3$)(CF$_3$)$_2$CH$_2$ | CH$_3$CH$_2$ | H | CF$_3$ | H |
| CF$_3$CFHCF$_2$CH$_2$ | CH$_3$CH$_2$ | H | CF$_3$ | H |
| CF$_3$(CF$_2$)$_2$CH$_2$ | CH$_3$CH$_2$ | H | CF$_3$ | H |
| CBrF$_2$CF$_2$CH$_2$CH$_2$ | CH$_3$CH$_2$ | H | CF$_3$ | H |
| CF$_3$CFHCF$_2$CH(CH$_3$) | CH$_3$CH$_2$ | H | CF$_3$ | H |
| CF$_3$(CF$_2$)$_3$CH$_2$ | CH$_3$CH$_2$ | H | CF$_3$ | H |
| CF$_3$(CF$_2$)$_4$CH$_2$ | CH$_3$CH$_2$ | H | CF$_3$ | H |
| CF$_3$(CF$_2$)$_3$CH$_2$CH$_2$ | CH$_3$CH$_2$ | H | CF$_3$ | H |
| CF(CF$_3$)$_2$CF$_2$CF$_2$CH$_2$CH$_2$ | CH$_3$CH$_2$ | H | CF$_3$ | H |
| CF$_2$H(CF$_2$)$_3$CH$_2$ | CH$_3$CH$_2$ | H | CF$_3$ | H |
| CF$_2$H(CF$_2$)$_5$CH$_2$ | CH$_3$CH$_2$ | H | CF$_3$ | H |
| CF$_3$(CF$_2$)$_3$CH$_2$CH$_2$CH$_2$ | CH$_3$CH$_2$ | H | CF$_3$ | H |
| CF$_3$CF$_2$(CH$_2$)$_5$CH$_2$ | CH$_3$CH$_2$ | H | CF$_3$ | H |
| CF$_3$(CF$_2$)$_5$CH$_2$CH$_2$CH$_2$ | CH$_3$CH$_2$ | H | CF$_3$ | H |
| CF$_3$(CF$_2$)$_3$CH$_2$(CH$_2$)$_4$CH$_2$ | CH$_3$CH$_2$ | H | CF$_3$ | H |
| CF$_3$(CF$_2$)$_5$CH$_2$CH$_2$ | CH$_3$CH$_2$ | H | CF$_3$ | H |
| CF(CF$_3$)$_2$CH$_2$(CH$_2$)$_4$CH$_2$ | CH$_3$CH$_2$ | H | CF$_3$ | H |
| CH$_2$FCF$_2$CH$_2$ | CH$_3$CH$_2$ | H | CF$_3$ | H |
| CH$_2$ClCF$_2$CH$_2$ | CH$_3$CH$_2$ | H | CF$_3$ | H |
| CH$_2$BrCF$_2$CH$_2$ | CH$_3$CH$_2$ | H | CF$_3$ | H |

TABLE 16

| $R^{1N}$ | $R^{4N}$ | $R^{51N}$ | $R^{52N}$ | $R^{53N}$ |
|---|---|---|---|---|
| CH$_2$F(CF$_2$)$_2$CH$_2$ | CH$_3$CH$_2$ | H | CF$_3$ | H |
| CH$_2$Cl(CF$_2$)$_2$CH$_2$ | CH$_3$CH$_2$ | H | CF$_3$ | H |
| CH$_2$Br(CF$_2$)$_2$CH$_2$ | CH$_3$CH$_2$ | H | CF$_3$ | H |
| CH$_2$F(CF$_2$)$_3$CH$_2$ | CH$_3$CH$_2$ | H | CF$_3$ | H |
| CH$_2$Cl(CF$_2$)$_3$CH$_2$ | CH$_3$CH$_2$ | H | CF$_3$ | H |
| CH$_2$Br(CF$_2$)$_3$CH$_2$ | CH$_3$CH$_2$ | H | CF$_3$ | H |
| CH$_2$F(CF$_2$)$_4$CH$_2$ | CH$_3$CH$_2$ | H | CF$_3$ | H |
| CH$_2$Cl(CF2)$_4$CH2 | CH$_3$CH$_2$ | H | CF$_3$ | H |
| CH$_2$Br(CF$_2$)$_4$CH$_2$ | CH$_3$CH$_2$ | H | CF$_3$ | H |

The compound represented by formula (1-N11) wherein $R^{2N}$ represents a methyl group, $R^{3N}$ represents a hydrogen group, and $R^{1N}$, $R^{4N}$, $R^{51N}$, $R^{52N}$, and $R^{53N}$ represent any one combination indicated in Table 11 to Table 16.

The compound represented by formula (1-N11) wherein $R^{2N}$ represents a trifluoromethyl group, $R^{3N}$ represents a hydrogen group, and $R^{1N}$, $R^{4N}$, $R^{51N}$, $R^{52N}$, and $R^{53N}$ represent any one combination indicated in Table 11 to Table 16.

The compound represented by formula (1-N11) wherein $R^{2N}$ represents a chlorine group, $R^{3N}$ represents a hydrogen group, and $R^{1N}$, $R^{4N}$, $R^{51N}$, $R^{52N}$, and $R^{53N}$ represent any one combination indicated in Table 11 to Table 16.

The compound represented by formula (1-N11) wherein $R^{2N}$ represents a fluorine group, $R^{3N}$ represents a hydrogen group, and $R^{1N}$, $R^{4N}$, $R^{51N}$, $R^{52N}$, and $R^{53N}$ represent any one combination indicated in Table 11 to Table 16.

The compound represented by formula (1-N11) wherein $R^{2N}$ represents a hydrogen group, $R^{3N}$ represents a methyl group, and $R^{1N}$, $R^{4N}$, $R^{51N}$, $R^{52N}$, and $R^{53N}$ represent any one combination indicated in Table 11 to Table 16.

The compound represented by formula (1-N11) wherein $R^{2N}$ represents a chlorine group, $R^{3N}$ represents a trifluoromethyl group, and $R^{1N}$, $R^{4N}$, $R^{51N}$, $R^{52N}$, and $R^{53N}$ represent any one combination indicated in Table 11 to Table 16.

The compound represented by formula (1-N11) wherein $R^{2N}$ represents a hydrogen group, $R^{3N}$ represents a chlorine group, and $R^{1N}$, $R^{4N}$, $R^{51N}$, $R^{52N}$, and $R^{53N}$ represent any one combination indicated in Table 11 to Table 16.

The compound represented by formula (1-N11) wherein $R^{2N}$ represents a hydrogen group, $R^{3N}$ represents a fluorine group, $R^{1N}$, $R^{4N}$, $R^{51N}$, $R^{52N}$, and $R^{53N}$ represent any one combination indicated in Table 11 to Table 16.

A compound represented by formula (1-N12):

(1-N12)

wherein $R^{2N}$ and $R^{3N}$ represent each a hydrogen atom, and $R^{1N}$, $R^{4N}$, $R^{51N}$, $R^{52N}$, and $R^{53N}$ represent any one combination indicated in Table 11 to Table 16.

The compound represented by formula (1-N12) wherein $R^{2N}$ represents a methyl group, $R^{3N}$ represents a hydrogen group, and $R^{1N}$, $R^{4N}$, $R^{51N}$, $R^{52N}$, and $R^{53N}$ represent any one combination indicated in Table 11 to Table 16.

The compound represented by formula (1-N12) wherein $R^{2N}$ represents a trifluoromethyl group, $R^{3N}$ represents a hydrogen group, and $R^{1N}$, $R^{4N}$, $R^{51N}$, $R^{52N}$, and $R^{53N}$ represent any one combination indicated in Table 11 to Table 16.

The compound represented by formula (1-N12) wherein $R^{2N}$ represents a chlorine group, $R^{3N}$ represents a hydrogen group, and $R^{1N}$, $R^{4N}$, $R^{51N}$, $R^{52N}$, and $R^{53N}$ represent any one combination indicated in Table 11 to Table 16.

The compound represented by formula (1-N12) wherein $R^{2N}$ represents a fluorine group, $R^{3N}$ represents a hydrogen group, and $R^{1N}$, $R^{4N}$, $R^{51N}$, $R^{52N}$, and $R^{53N}$ represent any one combination indicated in Table 11 to Table 16.

The compound represented by formula (1-N12) wherein $R^{2N}$ represents a hydrogen group, $R^{3N}$ represents a methyl group, and $R^{1N}$, $R^{4N}$, $R^{51N}$, $R^{52N}$, and $R^{53N}$ represent any one combination indicated in Table 11 to Table 16.

The compound represented by formula (1-N12) wherein $R^{2N}$ represents a chlorine group, $R^{3N}$ represents a trifluoromethyl group, and $R^{1N}$, $R^{4N}$, $R^{51N}$, $R^{52N}$, and $R^{53N}$ represent any one combination indicated in Table 11 to Table 16.

The compound represented by formula (1-N12) wherein $R^{2N}$ represents a hydrogen group, $R^{3N}$ represents a chlorine group, and $R^{1N}$, $R^{4N}$, $R^{51N}$, $R^{52N}$, and $R^{53N}$ represent any one combination indicated in Table 11 to Table 16.

The compound represented by formula (1-N12) wherein $R^{2N}$ represents a hydrogen group, $R^{3N}$ represents a fluorine group, $R^{1N}$, $R^{4N}$, $R^{51N}$, $R^{52N}$, and $R^{53N}$ represent any one combination indicated in Table 11 to Table 16.

A compound represented by formula (1-N13):

(1-N13)

wherein $R^{2N}$ and $R^{3N}$ represent each a hydrogen atom, $R^{6N}$ represent a hydrogen atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a methyl group, $R^{3N}$ represents a hydrogen group, $R^{6N}$ represent a hydrogen atom, and $R^{1N}$, $R^{4N}$, $R^{51N}$, $R^{52N}$ and $R^{53N}$ represent any one combination indicated in Table 11 to Table 16.

The compound represented by formula (1-N13) wherein $R^{2N}$ represents a trifluoromethyl group, $R^{3N}$ represents a hydrogen group, $R^{6N}$ represent a hydrogen atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a chlorine group, $R^{3N}$ represents a hydrogen group, $R^{6N}$ represent a hydrogen atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a fluorine group, $R^{3N}$ represents a hydrogen group, $R^{6N}$ represent a hydrogen atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a hydrogen group, $R^{3N}$ represents a methyl group, $R^{6N}$ represent a hydrogen atom, and $R^{1N}$, $R^{4N}$, $R^{51N}$, $R^{52N}$ and $R^{53N}$ represent any one combination indicated in Table 11 to Table 16.

The compound represented by formula (1-N13) wherein $R^{2N}$ represents a chlorine group, $R^{3N}$ represents a trifluoromethyl group, $R^{6N}$ represent a hydrogen atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a hydrogen group, $R^{3N}$ represents a chlorine group, $R^{6N}$ represent a hydrogen atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a hydrogen group, $R^{3N}$ represents a fluorine group, $R^{6N}$ represent a hydrogen atom, and $R^{1N}$, $R^{4N}$, $R^{5N}$, $R^{52N}$, and $R^{53N}$ represent any one combination indicated in Table 11 to Table 16.

The compound represented by formula (1-N13) wherein $R^{2N}$ represents a methyl group, $R^{3N}$ represents a hydrogen group, $R^{6N}$ represent a fluorine atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a trifluoromethyl group, $R^{3N}$ represents a hydrogen group, $R^{6N}$ represent a fluorine atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a chlorine group, $R^{3N}$ represents a hydrogen group, $R^{6N}$ represent a fluorine atom, and $R^{1N}$, $R^{4N}$, $R^{51N}$, $R^{52N}$, and $R^{53N}$ represent any one combination indicated in [Table 11 to Table 16.

The compound represented by formula (1-N13) wherein $R^{2N}$ represents a fluorine group, $R^{3N}$ represents a hydrogen group, $R^{6N}$ represent a fluorine atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a hydrogen group, $R^{3N}$ represents a methyl group, $R^{6N}$ represent a fluorine atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a chlorine group, $R^{3N}$ represents a trifluoromethyl group, $R^{6N}$ represent a fluorine atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a hydrogen group, $R^{3N}$ represents a chlorine group, $R^{6N}$ represent a fluorine atom, and $R^{1N}$, $R^{4N}$, $R^{51N}$, $R^{52N}$, and $R^{53N}$ represent any one combination indicated in Table 11 to Table 16.

The compound represented by formula (1-N13) wherein $R^{2N}$ represents a hydrogen atom, $R^{3N}$ represents a fluorine group, $R^{6N}$ N represent a fluorine atom, $R^{1N}$, $R^{4N}$, $R^{51N}$, $R^{52N}$, and $R^{53N}$ represent any one combination indicated in Table 1 to Table 10.

Examples of the harmful arthropod on which the compound of the present invention has a control efficacy include harmful insects and harmful mites. Specific examples of such harmful arthropod are as follows.

Hemiptera Pests:

Delphacidae (for example, *Laodelphax striatellus, Nilaparvata lugens, Sogatella furcifera*, or *Peregrinus maidis*), Deltocephalidae (for example, *Nephotettix cincticeps, Nephotettix virescens, Nephotettix nigropictus* (Rice green leafhopper), *Recilia dorsalis, Empoasca onukii, Empoasca fabae, Dalbulus maidis, Mahanarva posticata* (Sugarcane froghopper), *Mahanarva fimbriolota* (Sugarcane root spittlebug), *Cofana spectra, Nephotettix nigropictus*, or *Recilia dorsalis*), Aphididae (for example, *Aphis gossypii, Myzus persicae, Brevicoryne brassicae, Aphis spiraecola, Macrosiphum euphorbiae, Aulacorthum solani, Rhopalosiphum padi, Toxqptera citricidus, Hyalopterus pruni, Aphis glycines Matsumura, Rhopalosiphum maidis, Tetraneura nigriabdominalis, Viteus vitifoliae, Daktulosphaira vitifoliae* (Grape Phylloxera), *Phylloxera devastatrix Pergande* (Pecan *phylloxera*), *Phylloxera notabilis pergande* (Pecan leaf *phylloxera*), or *Phylloxera russellae Stoetzel* (Southern pecan leaf *phylloxera*), Pentatomidae (for example, *Scotinophara lurida, Scotinophara coarctata* (Malayan rice black bug), *Nezara antennata, Eysarcoris parvus, Ralyomorpha mista, Nezara viridula, Euschistus heros* (Brown stink bug), *Nezara viridula* (Southern green stink bug), *Piezodorus guildinii* (Red banded stink bug), *Scaptocoris castanea* (Burrower brown bug), *Oebalus pugnax*, or *Dichelops melacanthus*), Alydidae (for example, *Riptortus clavetus, Leptocorisa chinensis, Leptocorisa acuta*, or *Leptocorisa* spp.), Miridae (for example, *Trigonotylus caelestialium, Stenotus rubrovittatus, Lygus lineolaris*, or *Blissus leucopterus leucopterus* (Chinchi bug)), Aleyrodidae (for example, *Trialeurodes vaporariorum, Bemisia tabaci, Dialeurodes citri*, or *Aleurocanthus spiniferus*), Coccoidea (for example, *Aonidiella aurantii, Comstockaspis perniciosa, Unaspis citri, Ceroplastes rubens, Icerya purchasi, Planococcus Kraunhiae, Pseudococcus longispinis, Pseudaulacaspis Pentagona*, or *Brevennia rehi*), Psyllidae (for example, *Diaphorina citri, Psylla pyrisuga, Bactericerca cockerelli*), Tingidae (for example, *Stephanitis nasi*),
Cimicoidea (for example, *Cimex lectularius*),
*Quesada gigas* (Giant Cicada);
and the others.

Lepidoptera Pests:

Pyralidae (for example, *Chilo suppressalis*, *Chilo polychrysus* (Darkheaded stm borer), *Tryporyza incertulas*, *Chilo polychrysus*, *Scirpophaga innotata*, *Scirpophaga incertulas* (Yellow stem borer), *Sesamia inferens* (Pink borer), *Rupela albinella*, *Cnaphalocrocis medinalis*, *Marasmia patnalis*, *Marasmia exigna*, *Notarcha derogata*, *Plodia interpunctella*, *Ostrinia furnacalis*, *Hellula undalis*, *Pediasia teterrellus*, *Nymphula depunctalis*, *Marasmia* spp., *Hydraecia immanis* (Hop vine borer), *Ostrinia nubilalis* (European corn borer), *Elasmopalpus lignosellus* (Lesser cornstalk borer), *Epinotia aporema* (Bean Shoot Borer), *Diatraea saccharalis* (Sugarcane borer), *Telchin licus* (Giant Sugarcane borer)), Noctuidae (for example, *Spodoptera litura*, *Spodoptera exigua*, *Pseudaletia separata*, *Mamestra brassicae*, *Sesamia inferens*, *Spodoptera mauritia*, *Spodoptera frugiperda*, *Spodoptera exempta*, *Agrotis Ipsilon*, *Plusia nigrisigna*, *Pseudoplusia includens* (Soybean looper), *Trichoplusia* spp., *Heliothis* spp. (for example, *Heliothis virescens*), *Helicoverpa* spp. (for example, *Helicoverpa armigera*), *Anticarsia gammatalis* (Velvetbean caterpillar), or *Alabama argillacea* (Cotton leafworm)), Pieridae (for example, *Pieris rapae*),
Adokisofiesu genus,
Tortricidae (for example, *Grapholita molesta*, *Leguminivora glycinivorella*, *Matsumuraeses azukivora*, *Adoxophyes orana fasciata*, *Adoxophyes honmai*, *Homona magnanima*, *Archips fuscocupreanus*, or *Cydia pomonella*),
Gracillariidae (for example, *Caloptilia theivora*, or *Phyllonorycter ringoneella*),
Carposinidae (for example, *Carposina niponensis*, *Ecdytolopha aurantiana* (Citrus fruit borer)),
Lyonetiidae (for example, *Leucoptera coffeela* (Coffee Leaf miner), or *Lyonetia* spp.)),
Lymantriidae (for example, *Lymantria* spp., or *Euproctis* spp.),
Yponomeutidae (for example, *Plutella xylostella*),
Gelechiidae (for example, *Pectinophora gossypiella*, or *Phthorimaea operculella*),
Arctiidae (for example, *Hyphantria cunea*);
and the others.

Thysanoptera Pests:

Thysanopterae (for example, *Frankliniella occidentalis*, *Thrips parmi*, *Scirtothrips dorsalis*, *Thrips tabaci*, *Frankliniella intonsa*, *Frankliniella occidentalis*, *Haplothrips aculeatus*, *Stenchaetothrips biformis*);
and the others.

Diptera Pests:

House mosquitoes (*Culex* spp.) (for example, *Culex* pipiens pollens, *Culex tritaeniorhynchus*, or *Culex quinquefasciatus*),
*Aedes* spp. (for example, *Aedes aegypti*, or *Aedes albopictus*),
*Anopheles* spp. (for example, *Anopheles sinensis*),
Chironomidae,
Muscidae (for example, *Musca domestica*, or *Muscina stabulans*),
Anthomyiidae (for example, *Delia platura*, *Delia antiqua*, or *Tetanops myopaeformis*),
Agromyzidae (for example, *Agromyza oryzae*, *Hydrellia griseola*, *Liriomyza sativae*, *Liriomyza trifolii*, or *Chromatomyia horticola*),
Chloropidae (for example, *Chlorops oryzae*),
Tephritidae (for example, *Dacus cucurbitae*, or *Ceratitis capitata*),
Ephydridae (for example, *Hydrellia philippina*, or *Hydrellia sasakii*),
Drosophilidae,
Phoridae (for example, *Megaselia spiracularis*),
Psychodidae (for example, *Clogmia albipunctata*),
Sciaridae,
Cecidomyiidae (for example, *Mayetiola destructor*, or *Orseolia oryzae*),
Diopsidae (for example, *Diopsis macrophthalma*),
Tipulidae (for example, *Tipula oleracea* (Common cranefly), or *Tipula paludosa* (European cranefly));
and the others.

Coleoptera Pests:

Chrysomelidae (for example, *Diabrotica virgifera virgifera*, *Diabrotica undecimpunctata howardi*, *Diabrotica barberi*, *Diabrotica virgifera zeae*, *Diabrotica balteata LeConte*, *Diabrotica speciosa*, *Diabrotica speciosa* (Cucurbit Beetle), *Cerotoma trifurcata*, *Oulema melanopus*, *Aulacophora femoralis*, *Phyllotreta striolata*, *Leptinotarsa decemlineata*, *Oulema oryzae*, *Colaspis brunnea*, *Chaetocnema pulicaria*, *Epitrix cucumeris*, *Dicladispa armigera*, *Stenolophus lecontei* (Seedcorn beetle), or *Clivinia impressifrons* (Slender seedcorn beetle)), Scarabaeidae (for example, *Anomala cuprea*, *Anomala rufocuprea*, *Popillia japonica*, *Rhizotrogus majalis* (European Chafer), *Bothynus gibbosus* (Carrot beetle), *Colaspis brunnea* (Grape Colaspis), *Myochrous denticollis* (southern Corn leaf beetle), *Holotrichia* spp., or *Phyllophaga* spp. (for example, *Phyllophaga crinita*)), Erirhinidae (for example, *Sitophilus zeamais*, *Echinocnemus squameus*, *Lissorhoptrus oryzophilus*, or *Sphenophorus venatus*), Curculionidae (for example, *Anthonomus grandis*, *Sphenophorus callosus* (Southern Corn Billbug), *Sternechus subsignatus* (Soybean stalk weevil), or *Sphenophorus* spp. (for example, *Sphenophorus levis*)),

*Epilachna* (for example, *Epilachna vigintioctopunctata*),
Scolytidae (for example, *Lyctus brunneus*, or *Tomicus piniperda*),
Bostrichidae,
Ptinidae,
Cerambycidae (for example, *Anoplophora malasiaca*, or *Migdolus fryanus*),
Elateridae (*Agriotes* sp., *Aelous* sp., *Anchastus* sp., *Melanotus* sp., *Limonius* sp., *Conoderus* sp., *Ctenicera* sp.) (for example, *Melanotus okinawensis*, *Agriotes ogurae fuscicollis*, or *Melanotus legatus*),
Staphylinidae (for example, *Paederus fuscipes*),
*Hypothenemus hampei* (Coffee Barry Borer);
and the others.

Orthoptera Pests:

*Locusta migratoria*, *Gryllotalpa africana*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Twostriped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria*, *Gastrimargus musicus* (Yellow-winged locust), *Austracris guttulosa* (Spur-throated locust), *Oxya yezoensis*, *Oxya*

*japonica, Patanga succincta, Grylloidea* (for example, *Acheta domesticus, Teleogryllus emma*, or *Anabrus simplex* (Mormon cricket));
and the others.
Hymenoptera Pests:
Tenthredinidae (for exmaple, *Athalia rosae*, or *Athalia japonica*),
*Solenopsis* spp.,
*Attini* spp. (for example, *Atta capiguara* (Brown leaf-cutting ant));
and the others.
Blattariae Pests:
*Blattella germanica, Periplaneta fuliginosa, Periplaneta americana, Periplaneta brunnea, Blatta orientalis*, and the others.
Isoptera Pests:
*Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapritermes nitobei, Sinocapritermes mushae*, or *Cornitermes cumulans;*
and the others.
Acarina Pests:
Tetranychidae (for example, *Tetranychus urticae, Tetranychus kanzawai, Panonychus citri, Panonychus ulmi, Oligonychus* spp., or *Brevipalpus phoenicis* (Southern Turkey spider mites)),
Eriophyidae (for example, *Aculops pelekassi, Phyllocoptruta citri, Aculops lycopersici, Calacarus carinatus, Acaphylla theavagrans, Eriophyes chibaensis*, or *Aculus schlechtendali*),
Tarsonemidae (for example, *Polyphagotarsonemus latus*),
Tenuipalpidae (for Example, *Brevipalpus phoenicis*),
Tuckerellidae;
Ixodidae (for Example, *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus*, or *Rhipicephalus sanguineus*),
Acaridae (for example, *Tyrophagus* putrescentiae, or *Tyrophagus similis*),
Pyroglyphidae (for example, *Dermatophagoides farinae*, or *Dermatophagoides ptrenyssnus*);
Cheyletidae (for example, *Cheyletus eruditus, Cheyletus malaccensis*, or *Cheyletus moorei*);
Sarcoptidae (for example, *Octodectes cynotis*, or *Sacroptes scabiei*),
*Demodex folliculorum* (for example, *Demodex canis*),
Listrophoridae,
Oribatid mites,
Dermanyssidae (for example, *Ornithonyssus bacoti, Ornithonyssus sylvairum*, or *Dermanyssus* gallinae),
Trombiculid mites (for example, *Leptotrombidium akamushi*),
and the others.
The agent for controlling harmful arthropods of the present invention comprises the present compound and an inert active carrier. The agent for controlling harmful arthropods is usually prepared by mixing the present compound with an inert active carrier such as solid carrier, liquid carrier and gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment. Also, the agent for controlling harmful arthropods of the present invention may be mixed with other pesticides, miticides, nematicides, fungicides, plant growth regulators, herbicides, and synergists.

The agent for controlling harmful arthropods of the present invention comprises usually 0.01 to 95% by weight of the present compound.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate, or hydrated silica) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethylmethacrylate and polyethylene terephthalate; nylon resins (for example, nylon-6, nylon-11 and nylon-66); polyamide resins; polyvinyl chloride, polyvinylidene chloride, vinyl chloride-propylene copolymers, and the others).

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether, or 3-methoxy-3-methyl-1-butanol); acid amides (for example, DMF, or N,N-dimethylacetamide); halogenated hydrocarbons (for example, dichloromethane, trichloroethane, or carbon tetrachloride); sulfoxides (for example, dimethyl sulfoxide); propylene carbonate; and vegetable oils (for example, soybean oil, or cottonseed oil).

Examples of the gaseous carrier include fluorocarbon, butane gas, LPG (liquefied petroleum gas), dimethyl ether, and carbon dioxide gas.

Examples of the surfactant include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agent for formulation include a binder, a dispersant, a colorant and a stabilizer. Specific examples include casein, gelatin, polysaccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

Examples of a base material of the resin formulation include polyvinyl chloride polymers, polyurethane and the others, and a plasticizer such as phthalate esters (for example, dimethyl phthalate, dioctyl phthalate), adipic acid esters and stearic acid may be added to the base material, if necessary. The resin formulation can be prepared by mixing the present compound with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. The resin formulation can be processed into animal collars, animal ear tags, sheet products, trap strings, gardening supports, and other products.

Examples of a base material for the poison bait include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is conducted by applying an effective amount of the present compound to a harmful arthropod directly and/or a habitat thereof (for example, plant bodies, soil, an interior of a house, and animal bodies). In the method for controlling harmful arthropods of the present invention, the present compound is usually used in the form of a harmful arthropod controlling agent.

When an agent for controlling harmful arthropods of the present invention is used for controlling harmful arthropods in an agricultural field, the application dose as an amount of the present compound is usually within a range from 1 to 10,000 g per 10,000 m$^2$. The emulsifiable concentrate, the wettable powder, or the flowable formulation etc. of an agent for controlling harmful arthropods of the present invention is usually applied by diluting it with water in such a way that a concentration of the active ingredient of the present invention is within a range from 0.01 to 10,000 ppm. The granular formulation, or the dust formulation etc., is usually applied as itself without diluting it.

These formulations and diluents of the formulations with water may be directly sprayed to a harmful arthropod or a plant such as a crop to be protected from a harmful arthropod, or applied to a soil in a cultivated area to control a harmful arthropod that inhabits the soil.

Also, a resin formulation processed into sheet shape or string shape may be wrapped around a crop, stretched near a crop, spread on a plant foot soil, or the like.

When the agent for controlling harmful arthropods of the present invention is used to control harmful arthropods that live inside a house, the application dose as an amount of the present compound is usually within a range from 0.01 to 1,000 mg per 1 m$^2$ of an area to be treated, in the case of using it on a planar area. In the case of using it spatially, the application dose as an amount of the present compound is usually within a range from 0.01 to 500 mg per 1 m$^3$ of the space to be treated. When the agent for controlling harmful arthropods of the present invention is formulated into emulsifiable concentrates, wettable powders, flowables or the others, the formulation is usually applied after diluting it with water in such a way that a concentration of the active ingredient is within a range from 0.1 to 10,000 ppm, and then sparging it. In the case of being formulated into oil solutions, aerosols, smoking agents, poison baits and the others, the formulation is used as itself without diluting it.

When the agent for controlling harmful arthropods of the present invention is used for controlling external parasites of livestock such as cows, horses, pigs, sheep, goats and chickens, and small animals such as dogs, cats, rats and mice, the pest control agent of the present invention can be applied to the animal by a known method in the veterinary field. Specifically, when systemic control is intended, the pest control agent of the present invention is administered to the animal as a tablet, a mixture with feed or a suppository, or by injection (including intramuscular, subcutaneous, intravenous and intraperitoneal injections). On the other hand, when non-systemic control is intended, the pest control agent of the present invention is applied to the animal by means of spraying of the oil solution or aqueous solution, pour-on or spot-on treatment, or washing of the animal with a shampoo formulation, or by putting a collar or ear tag made of the resin formulation to the animal. In the case of administering to an animal body, the dose of the present compound is usually within a range from 0.1 to 1,000 mg per 1 kg of an animal body weight.

EXAMPLES

The following examples including Preparation examples, Formulation examples and Test examples serve to illustrate the present invention in more detail, which should not intend to limit the present invention.

First, regarding the preparation of the present compound, Preparation examples are shown as follows.

Preparation Example 1(1)

Eighty (80) ml of the mixture of 3-chloro-6-methoxypyridazine 17 g, 2-fluoro-4-(trifluoromethyl)phenylboron acid pynacol ester 12 g, tetrakis(triphenylphosphine)palladium(0) 2.3 g, 2M solution of sodium carbonate 50 ml, and 1,2-dimethoxyethane (hereinafter, referred to as "DME") 80 ml was stirred at 80° C. for 5 hours. The reaction mixture was allowed to stand to room temperature and to the mixture was added water, and the mixture was extracted with ethyl acetate, and dried over anhydrous sodium sulfate. The mixture was concentratated under reduced pressure, and the resulting residue was then subjected to a silica gel column chromatography to give Intermediate compound (1-1) 4.81 g.

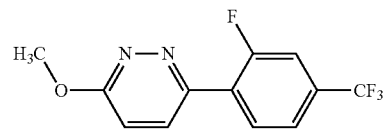 [SMILES: COc1ccc(-c2ccc(C(F)(F)F)cc2F)nn1]

$^1$H-NMR (CDCl$_3$) δ: 8.28 (1H, dd), 7.90 (1H, dd), 7.58 (1H, d), 7.47 (1H, d), 7.09 (1H, d), 4.21 (3H, s).

Preparation Example 1(2)

To the reaction mixure of the Intermediate compound (1-1) 4.8 g and NMP 40 ml, ethanethiol 1.6 ml and sodium hydride (60%, oily) 0.99 g were added under ice-cooling, and the mixture was stirred at room temperature for 2 hours.

To the reaction mixtures was added water, and the mixtures were extracted with ethyl acetate and dried over anhydrous sodium sulfate. The obtained organic layer was concentrated under reduced pressure to give an Intermediate compound (1-2).

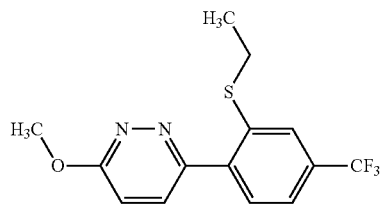 [SMILES: CCSc1cc(C(F)(F)F)ccc1-c1ccc(OC)nn1]

$^1$H-NMR (CDCl$_3$) δ: 7.72 (1H, d), 7.68-7.63 (2H, m), 7.55 (1H, d), 7.05 (1H, d), 4.21 (3H, s), 2.89 (2H, q), 1.25 (3H, t).

Preparation Example 1(3)

To the mixture of a full amount of the Intermediate compound (1-2) obtained in Preparation example 1(2) and chloroform 40 ml, mCPBA (purity 65% or more) 8.9 g was added under ice-cooling, and the mixture was stirred at room temperature for one day. To the reaction mixtures was added 10% aqueous sodium thiosulfate solution, and the mixtures were extracted with chloroform. The organic layer was washed with saturated aqueous sodium hydrocarbonate solution, dried over anhydrous sodium sulfate, and concentrated under reduced pressure. The obtained residue was subjected to a silica gel column chromatography to give Intermediate compound (1-3) 3.3 g.

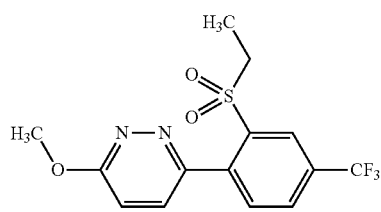 [SMILES: CCS(=O)(=O)c1cc(C(F)(F)F)ccc1-c1ccc(OC)nn1]

$^1$H-NMR (CDCl$_3$) δ: 8.45 (1H, s), 8.00 (1H, d), 7.60 (1H, d), 7.53 (1H, d), 7.12 (1H, d), 4.21 (3H, s), 3.46 (2H, q), 1.29 (3H, t).

Preparation Example 1(4)

The mixture of the Intermediate compound (1-3) 3.3 g and concentrated hydrochloric acid 25 mL was heated to reflux for 1 hour. The obtained mixture was allwed to stand to room temperature, and thereto was added water. The precipitated solid was filtered and the filtrate was concentrated under reduced pressure to give an Intermediate compound (1-4) 2.9 g.

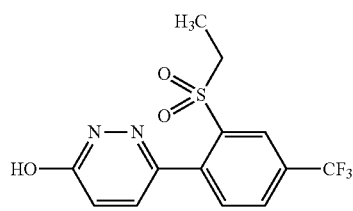 [SMILES: CCS(=O)(=O)c1cc(C(F)(F)F)ccc1-c1ccc(O)nn1]

$^1$H-NMR (CDCl$_3$) δ: 11.74 (1H, s), 8.41 (1H, s), 8.01 (1H, d), 7.62 (1H, d), 7.42 (1H, d), 7.06 (1H, d), 3.30 (2H, q), 1.30 (3H, t).

Preparation Example 1(5)

To the mixture of the Intermediate (1-4) 0.30 g, cesium carbonate 0.35 g, and NMP 4 ml, 2,2,2-trifluoroethyl nonafluorobutane sulfonate 0.37 g were added at room temperature, and the mixture was stirred at room temperature for 2 hours. To the obtained reaction mixture was added water, and the mixture was extracted with ethyl acetate and dried over anhydrous sodium sulfate. After the organic layer was concentrated under reduced pressure, the obtained residue was subjected to a silica gel column chromatography to give Present compound 1 0.02 mg and By-product 1 0.31 g.

Present Compound 1

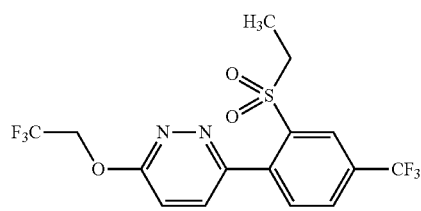 [SMILES: CCS(=O)(=O)c1cc(C(F)(F)F)ccc1-c1ccc(OCC(F)(F)F)nn1]

$^1$H-NMR (CDCl$_3$) δ: 8.46 (1H, s), 8.02 (1H, d), 7.65-7.59 (2H, m), 7.27 (1H, d), 5.00 (2H, q), 3.43 (2H, q), 1.30 (3H, t).

By-Product 1

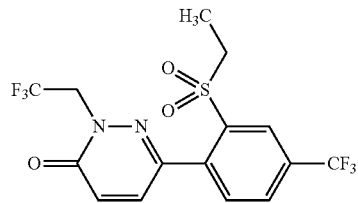 [SMILES: CCS(=O)(=O)c1cc(C(F)(F)F)ccc1-c1ccc(=O)n(CC(F)(F)F)n1]

$^1$H-NMR (CDCl$_3$) δ: 8.40 (1H, s), 8.02 (1H, d), 7.61 (1H, d), 7.37 (1H, d), 7.05 (1H, d), 4.81 (2H, q), 3.19 (2H, q), 1.28 (3H, t).

The present compound was prepared according to the method described in Preparation example 1(5) using the compound represented by Formula R$^1$—OSO$_2$CF$_3$ instead of 2,2,2-trifluoroethyl nonafluorobutane sulfonate, and is shown in Table 17.

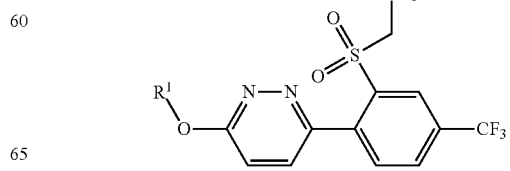

TABLE 17

| Present compound No. | R¹ |
|---|---|
| 2 | $CF_3CF_2CH_2$ |
| 3 | $CF_3CHFCF_2CH_2$ |

Present compound 2; ¹H-NMR (CDCl₃) δ: 8.46 (1H, s), 8.02 (1H, d), 7.63 (1H, d), 7.61 (1H, d), 7.27 (1H, d), 5.08 (2H, t), 3.43 (2H, q), 1.30 (3H, t).

Present compound 3; ¹H-NMR (CDCl₃) δ: 8.46 (1H, s), 8.02 (1H, d), 7.63 (1H, d), 7.61 (1H, d), 7.24 (1H, d), 5.28-5.06 (1H, m), 5.04-4.95 (2H, m), 3.42 (2H, q), 1.30 (3H, t).

The by-product prepared with the present compound is shown in Table 18.

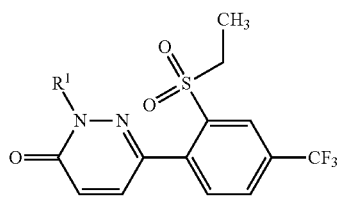

TABLE 18

| By-product No. | R¹ |
|---|---|
| 2 | $CF_3CF_2CH_2$ |
| 3 | $CF_3CHFCF_2CH_2$ |

By-product 2; ¹H-NMR (CDCl₃) δ: 8.40 (1H, s), 8.02 (1H, d), 7.61 (1H, d), 7.38 (1H, d), 7.04 (1H, d), 4.84 (2H, t), 3.17 (2H, q), 1.27 (3H, t).

By-product 3; ¹H-NMR (CDCl₃) δ: 8.41 (1H, s), 8.02 (1H, d), 7.61 (1H, d), 7.38 (1H, d), 7.05 (1H, d), 5.18-5.01 (1H, m), 4.90-4.69 (2H, m), 3.19 (2H, q), 1.28 (3H, t).

Preparation Example 2(1)

To 3-chloropyridine-2-carbonitrile 54 g, and THF 300 mL, 1M THF solution of methyl magnesium bromide 500 mg was added dropwise under ice-cooling. The obtained reaction mixtures were stirred under ice-cooling for 2 hours. The obtained reaction mixtures were added to 2N hydrochloric acid under ice-cooling, and stirred for 30 minutes. To the mixtures was added 1N sodium hydroxide solution to adjust to pH 8, and the mixtures were extracted with ethyl acetate. The obtained organic layer was washed with brine and dried over anhydrous sodium sulfate. The organic layer was concentrated to give the Intermediate compound (4-1) 58 g.

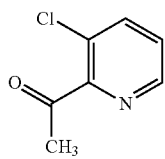

¹H-NMR (CDCl₃) δ: 8.55 (1H, dd), 7.80 (1H, dd), 7.38 (1H, dd), 2.70 (3H, s).

Preparation Example 2(2)

To the suspension of sodium hydride (60%, oily) 57 g and DMF 560 mL, ethanethiol 100 mL was added dropwise under ice-cooling. To the mixtures, a mixed solution of the Intermediate compound (4-1) 204 g and DMF 190 mL were added dropwise under ice-cooling. The obtained reaction mixtures were stirred under ice-cooling for 1 hour, and thereto was added iced water. The precipitated solid was filtered and washed with water. The obtained solid was dissolved in ethyl acetate, and the solution was washed with brine, and then the organic layer was dried with sodium sulfate. After the organic layer was concentrated under reduced pressure, the obtained solid was washed with hexane to give the Intermediate compound (4-2) 160 g.

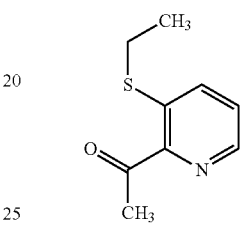

¹H-NMR (CDCl₃) δ: 8.40 (1H, dd), 7.69 (1H, dd), 7.37 (1H, dd), 2.92 (2H, q), 2.72 (3H, s), 1.40 (3H, t).

Preparation Example 2(3)

To the mixture of the Intermediate compound (4-2) 5.4 g, glyoxylic acid monohydrate 2.8 g and methanol 90 ml, sodium hydroxide 2.4 g and methanol 60 mL were added dropwise under ice-cooling. The reaction mixture was stirred at 60° C. for 2 hours. The obtained reaction mixture was allowed to stand to room temperature, and thereto were sequentially added acetic acid 11 mL and hydrazine monohydrate 2.3 g. The obtained mixtures were allowed to stand to room temperature, followed by thereto was added saturated ammonium chloride solution, and the mixture was extracted with chloroform. The obtained organic layer was dried over sodium sulfate and concentrated under reduced pressure. The obtained residue was subjected to a silica gel column chromatography to give the Intermediate compound (4-3) 3.8 g.

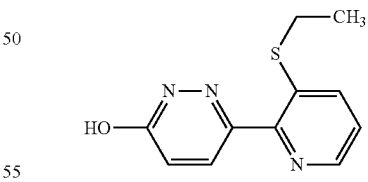

¹H-NMR (CDCl₃) δ: 10.60 (1H, br s), 8.43 (1H, dd), 8.13 (1H, d), 7.71 (1H, dd), 7.29 (1H, dd), 7.05 (1H, d), 2.95 (2H, q), 1.35 (3H, t).

Preparation Example 2(4)

To the mixture of the Intermediate compound (4-3) 2.0 g and toluene 9 ml, DMF and phosphorus oxychloride 1.6 mL were added sequentially. The mixtures were stirred at 100° C. for 2 hours. The obtained mixtures were allowed to stand to room temperature and then concentrated under reduced pressure. The obtained residue was diluted with chloroform and to the mixtures were added water under ice-cooling. The obtained mixtures were extracted with chloroform, washed with water and brine, and then dried over sodium sulfate. The obtained organic layer was concentrated under reduced pressure to give the Intermediate compound (4-4) 2.2 g.

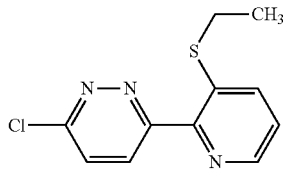 [SMILES: CCSc1cccnc1-c1ccc(Cl)nn1]

$^1$H-NMR (CDCl$_3$) δ: 8.48 (1H, dd), 8.25 (1H, d), 7.79 (1H, dd), 7.63 (1H, d), 7.34 (1H, dd), 2.95 (2H, q), 1.33 (3H, t).

Preparation Example 2(5)

To the mixture of the Intermediate compound (4-4) 2.2 g and chloroform 43 ml, mCPBA (75%) 4.2 g was added under ice-cooling. The reaction mixtures were stirred at room temperature for 24 hours. To the mixtures, sodium sulfite 11 g and saturated sodium hydrogen carbonate solution were added, and the mixtures weres extracted with chloroform. The obtained organic layer was dried over sodium sulfate and concentrated under reduced pressure. The obtained residue was subjected to a silica gel column chromatography to give the Intermediate compound (4-5) 2.2 g.

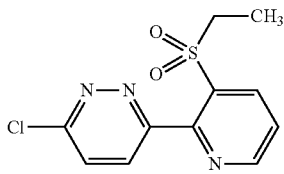 [SMILES: CCS(=O)(=O)c1cccnc1-c1ccc(Cl)nn1]

$^1$H-NMR (CDCl$_3$) δ: 8.93 (1H, dd), 8.54 (1H, dd), 7.95 (1H, d), 7.71 (1H, d), 7.66 (1H, dd), 3.89 (2H, q), 1.41 (3H, t).

Preparation Example 2(6)

To the mixture of the Intermediate compound (4-5) 3.0 g, tetrabutylammonium chloride 880 mg and DMF 26 mL, sodium methanesulfinate 1.6 g was added at room temperature. The mixtures were stirred at 100° C. for 5 hours. The obtained mixtures were allowed to stand to room temperature and thereto was added water, and the mixtures were then extracted with ethyl acetate. The obtained organic layer was dried over sodium sulfate and concentrated under reduced pressure. The obtained residue was subjected to a silica gel column chromatography to give the Intermediate compound (4-6) 3.0 g.

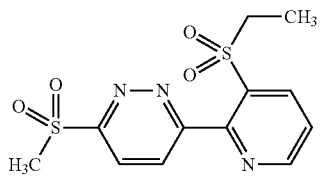

$^1$H-NMR (CDCl$_3$) δ: 8.98 (1H, dd), 8.57 (1H, dd), 8.37 (1H, d), 8.25 (1H, d), 7.72 (1H, dd), 3.90 (2H, q), 3.48 (3H, s), 1.43 (3H, t).

Preparation Example 2(7)

To the mixture of the Intermediate compound (4-6) 0.2 g, cesium carbonate 0.23 g, and NMP 2 mL, 2,2,2-trichloroethanol 0.1 g was added at room temperature, and the mixtures were stirred at room temperature for 1 hours, followed by at 50° C. for 30 minutes. The reaction mixtures were allowed to stand to room temperature, and thereto was added water, and the mixtures were then extracted with ethyl acetate and dried over sodium sulfate. After the mixture was concentrated under reduced pressure, the obtained residue was subjected to a silica gel column chromatography to give Present compound 4 0.19 g.

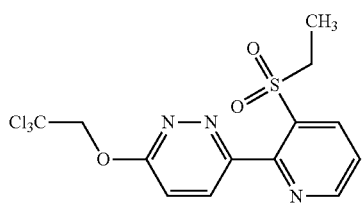

$^1$H-NMR (CDCl$_3$) δ: 8.92 (1H, dd), 8.53 (1H, dd), 7.95 (1H, d), 7.63 (1H, dd), 7.34 (1H, d), 5.28 (2H, s), 3.88 (2H, q), 1.40 (3H, t).

The present compound was prepared according to the method described in Preparation example 2(7) using the compound represented by Formula R$^1$—OH instead of 2,2, 2-trichloroethanol and shown in Table 19.

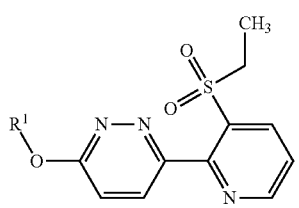

TABLE 19

| Present compound No. | R$_1$ |
| --- | --- |
| 5 | CF$_3$CH$_2$ |
| 6 | CF$_3$CH$_2$CH$_2$ |
| 10 | CF$_3$CH$_2$CH$_2$CH$_2$ |
| 12 | CF$_3$CH$_2$CH$_2$CH$_2$CH$_2$ |
| 14 | F$_3$C-CF(F)-CH(CH$_3$)- |
| 15 | CF$_2$HCH$_2$ |
| 16 | CF$_3$CH$_2$OCH$_2$CH$_2$ |
| 17 | CF$_3$CF$_2$CF$_2$CH$_2$ |
| 18 | CF$_3$CF$_2$CF$_2$CF$_2$CH$_2$ |
| 19 | CF$_3$CF$_2$CF$_2$CF$_2$CH$_2$CH$_2$ |
| 20 | CF$_3$CF$_2$CF$_2$CF$_2$CF$_2$CH$_2$ |
| 21 | CF(CF$_3$)$_2$CF$_2$CF$_2$CH$_2$CH$_2$ |

TABLE 19-continued

| Present compound No. | R₁ |
|---|---|
| 22 | 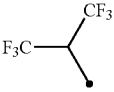 |
| 23 | 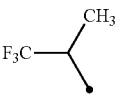 |
| 24 | 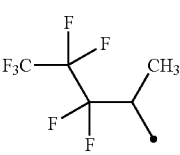 |
| 25 | 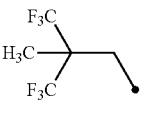 |
| 26 | 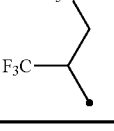 |

Present compound 5; $^1$H-NMR (CDCl$_3$) δ: 8.92 (1H, dd), 8.53 (1H, dd), 7.94 (1H, d), 7.63 (1H, dd), 7.29 (1H, d), 5.01 (2H, q), 3.87 (2H, q), 1.40 (3H, t).

Present compound 6; $^1$H-NMR (CDCl$_3$) δ: 8.91 (1H, dd), 8.52 (1H, dd), 7.87 (1H, d), 7.61 (1H, dd), 7.17 (1H, d), 4.83 (2H, t), 3.89 (2H, q), 2.79-2.66 (2H, m), 1.40 (3H, t).

Present compound 10; $^1$H-NMR (CDCl$_3$) δ: 8.91 (1H, dd), 8.52 (1H, dd), 7.86 (1H, d), 7.61 (1H, dd), 7.14 (1H, d), 4.65 (2H, t), 3.89 (2H, q), 2.42-2.28 (2H, m), 2.19-2.10 (2H, m), 1.39 (3H, t).

Present compound 12; $^1$H-NMR (CDCl$_3$) δ: 8.91 (1H, dd), 8.51 (1H, dd), 7.84 (1H, d), 7.60 (1H, dd), 7.13 (1H, d), 4.61 (2H, t), 3.90 (2H, q), 2.27-2.13 (2H, m), 2.00-1.92 (2H, m), 1.86-1.76 (2H, m), 1.39 (3H, t).

Present compound 14; $^1$H-NMR (CDCl$_3$) δ: 8.91 (1H, dd), 8.52 (1H, dd), 7.90 (1H, d), 7.62 (1H, dd), 7.20 (1H, d), 6.19 (1H, m), 3.93-3.77 (2H, m), 1.66 (3H, d), 1.39 (3H, t).

Present compound 15; $^1$H-NMR (CDCl$_3$) δ: 8.91 (1H, dd), 8.52 (1H, dd), 7.90 (1H, d), 7.62 (1H, dd), 7.23 (1H, d), 6.22 (1H, tt), 4.81 (2H, dt), 3.87 (2H, q), 1.40 (3H, t).

Present compound 16; $^1$H-NMR (CDCl$_3$) δ: 8.91 (1H, dd), 8.51 (1H, dd), 7.86 (1H, d), 7.60 (1H, dd), 7.19 (1H, d), 4.80-4.77 (2H, m), 4.08 (2H, t), 3.97 (2H, q), 3.88 (2H, q), 1.39 (3H, t).

Present compound 17; $^1$H-NMR (CDCl$_3$) δ: 8.92 (1H, dd), 8.53 (1H, dd), 7.94 (1H, d), 7.62 (1H, dd), 7.29 (1H, d), 5.13 (2H, t), 3.87 (2H, q), 1.40 (3H, t).

Present compound 18; $^1$H-NMR (CDCl$_3$) δ: 8.92 (1H, dd), 8.53 (1H, dd), 7.94 (1H, d), 7.63 (1H, dd), 7.27 (1H, d), 5.14 (2H, t), 3.87 (2H, q), 1.40 (3H, t).

Present compound 19; $^1$H-NMR (CDCl$_3$) δ: 8.91 (1H, dd), 8.52 (1H, dd), 7.87 (1H, d), 7.61 (1H, dd), 7.16 (1H, d), 4.92 (2H, t), 3.88 (2H, q), 2.78-2.68 (2H, m), 1.40 (3H, t).

Present compound 20; $^1$H-NMR (CDCl$_3$) δ: 8.92 (1H, dd), 8.53 (1H, dd), 7.94 (1H, d), 7.62 (1H, dd), 7.29 (1H, d), 5.14 (2H, t), 3.87 (2H, q), 1.40 (3H, t).

Present compound 21; $^1$H-NMR (CDCl$_3$) δ: 8.91 (1H, dd), 8.52 (1H, dd), 7.87 (1H, d), 7.61 (1H, dd), 7.16 (1H, d), 4.91 (2H, t), 3.88 (2H, q), 2.74 (2H, tt), 1.40 (3H, t).

Present compound 22; $^1$H-NMR (CDCl$_3$) δ: 8.92 (1H, dd), 8.53 (1H, dd), 8.01 (1H, d), 7.64 (1H, dd), 7.38 (1H, d), 6.86 (1H, dd), 3.82 (2H, q), 1.39 (3H, t).

Present compound 23; $^1$H-NMR (CDCl$_3$) δ: 8.91 (1H, dd), 8.52 (1H, dd), 7.91 (1H, t), 7.62 (1H, dd), 7.22 (1H, d), 6.12-6.03 (1H, m), 3.93-3.79 (2H, m), 1.63 (3H, d), 1.39 (3H, t).

Present compound 24; $^1$H-NMR (CDCl$_3$) δ: 8.91 (1H, dd), 8.52 (1H, dd), 7.90 (1H, t), 7.62 (1H, dd), 7.20 (1H, d), 6.23 (1H, m), 3.85 (2H, m), 1.67 (3H, d), 1.39 (3H, t).

Present compound 25; $^1$H-NMR (CDCl$_3$) δ: 8.91 (1H, dd), 8.52 (1H, dd), 7.90 (1H, d), 7.62 (1H, dd), 7.22 (1H, d), 4.89 (2H, s), 3.88 (2H, q), 1.59 (3H, d), 1.40 (3H, t).

Present compound 26; $^1$H-NMR (CDCl$_3$) δ: 8.91 (1H, dd), 8.52 (1H, dd), 7.91 (1H, t), 7.61 (1H, dd), 7.23 (1H, d), 6.17-6.09 (1H, m), 3.91-3.77 (2H, m), 2.12-1.88 (2H, m), 1.38 (3H, t), 1.09 (3H, t).

Preparation Example 3(1)

The Intermediate compound (7-1) was prepared according to the method described in Preparation example 2(7) using the compound represented by 1-hydroxy-acetone instead of 2,2,2-trichloroethanol.

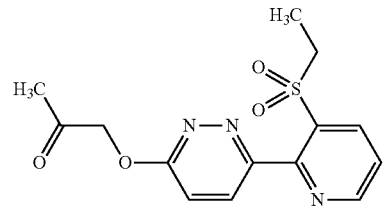 [SMILES: CCS(=O)(=O)c1cccnc1-c1ccc(OCC(C)=O)nn1]

$^1$H-NMR (CDCl$_3$) δ: 8.91 (1H, dd), 8.51 (1H, dd), 7.90 (1H, d), 7.61 (1H, dd), 7.29 (1H, d), 5.20 (2H, s), 3.85 (2H, q), 2.28 (3H, s), 1.38 (3H, t).

Preparation Example 3(2)

To the mixture of the Intermediate compound (7-1) 110 mg, and chloroform 2 mL, bis(2-methoxyethyl)aminosulfur trifluoride 150 mg was added dropwise under ice-cooling. The mixtures were stirred at room temperature for 6.5 hours. The obtained mixtures were added to saturated aqueous sodium hydrocarbonate solution and extracted with ethyl acetate. The obtained organic layers were washed with brine, followed by dried over sodium sulfate and concentrated under reduced pressure. The obtained residue was subjected to a silica gel column chromatography to give 3-(2,2-difluoropropoxy)-6-(3-ethanesulfonylpyridin-2-yl)pyridazine (hereinafter, referring to as "Present compound 7") 31 mg.

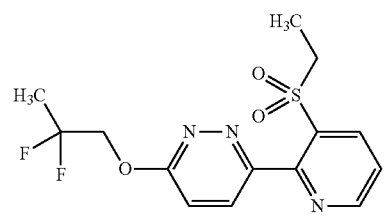 [SMILES: CCS(=O)(=O)c1cccnc1-c1ccc(OCC(C)(F)F)nn1]

$^1$H-NMR (CDCl$_3$) δ: 8.92 (1H, dd), 8.52 (1H, dd), 7.91 (1H, d), 7.62 (1H, dd), 7.25 (1H, d), 4.76 (2H, t), 3.89 (2H, q), 1.81 (3H, t), 1.40 (3H, t).

Preparation Example 4(1)

The Intermediate compound (8-1) was prepared according to the method described in Preparation example 2(5) using the Intermediate compound (4-3) instead of the Intermediate compound (4-4).

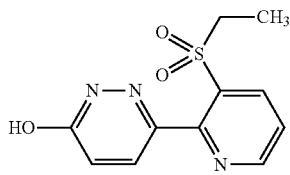 [SMILES: CCS(=O)(=O)c1cccnc1-c1ccc(O)nn1]

$^1$H-NMR (CDCl$_3$) δ: 12.07 (1H, s), 8.90 (1H, dd), 8.49 (1H, dd), 7.80 (1H, d), 7.61 (1H, dd), 7.11 (1H, d), 3.67 (2H, q), 1.39 (3H, t).

Preparation Example 4(2)

Present compound 8 and the by-product 8 were prepared according to the method described in Preparation example 1(5) using the Intermediate compound (8-1) instead of the Intermediate compound (1-4) and 2,2,3,3,3-pentafluoropropyl trifluoromethane sulfonate instead of 2,2,2-trifluoroethyl nonafluorobutane sulfonate.

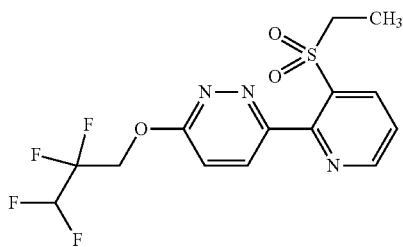 [SMILES: CCS(=O)(=O)c1cccnc1-c1ccc(OCC(F)(F)C(F)F)nn1]

$^1$H-NMR (CDCl$_3$) δ: 8.92 (1H, dd), 8.53 (1H, dd), 7.93 (1H, d), 7.63 (1H, dd), 7.27 (1H, d), 6.21-5.90 (1H, m), 5.01 (2H, t), 3.88 (2H, q), 1.40 (3H, t).
By-Product 8

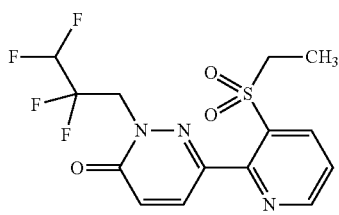 [SMILES: CCS(=O)(=O)c1cccnc1-c1ccc(=O)n(CC(F)(F)C(F)F)n1]

$^1$H-NMR (CDCl$_3$) δ: 8.91 (1H, dd), 8.49 (1H, dd), 7.73 (1H, d), 7.63 (1H, dd), 7.10 (1H, d), 6.13-5.82 (1H, m), 4.78 (2H, t), 3.56 (2H, q), 1.38 (3H, t).

The present compound was prepared according to the method described in Preparation example 4(2) using the compound represented by Formula R$^1$—OSO$_2$CF$_3$ instead of 2,2,3,3,3-pentafluoropropyl trifluoromethane sulfonate and is shown in Table 20.

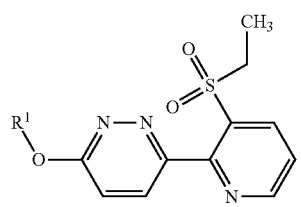

TABLE 20

| Present compoun No. | R$^1$ |
|---|---|
| 9 | CF$_3$CF$_2$CH$_2$ |
| 11 | CF$_3$CHFCF$_2$CH$_2$ |

Present compound 9; $^1$H-NMR (CDCl$_3$) δ: 8.92 (1H, dd), 8.53 (1H, dd), 7.94 (1H, d), 7.63 (1H, dd), 7.29 (1H, d), 5.08 (2H, t), 3.87 (2H, q), 1.40 (3H, t).
Present compound 11; $^1$H-NMR (CDCl$_3$) δ: 8.92 (1H, dd), 8.53 (1H, dd), 7.95 (1H, d), 7.63 (1H, dd), 7.27 (1H, d), 5.28-5.06 (1H, m), 5.05-4.96 (2H, m), 3.87 (2H, q), 1.40 (3H, t).

The by-product prepared with the present compound described in Table 20 is shown in Table 21.

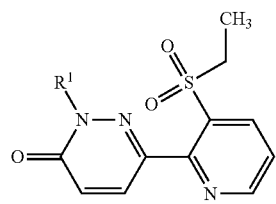

TABLE 21

| Side product No. | R$^1$ |
|---|---|
| 9 | CF$_3$CF$_2$CH$_2$ |
| 11 | CF$_3$CHFCF$_2$CH$_2$ |

By-product 9; $^1$H-NMR (CDCl$_3$) δ: 8.92 (1H, dd), 8.50 (1H, dd), 7.74 (1H, d), 7.64 (1H, dd), 7.10 (1H, d), 4.86 (2H, t), 3.54 (2H, q), 1.38 (3H, t).
By-product 11; $^1$H-NMR (CDCl$_3$) δ: 8.92 (1H, dd), 8.49 (1H, dd), 7.73 (1H, d), 7.64 (1H, dd), 7.11 (1H, d), 5.21-5.00 (1H, m), 4.93-4.69 (2H, m), 3.54 (2H, q), 1.38 (3H, t).

Preparation Example 5(1)

To the mixture of 5.0 g of 3-ethylsulfanyl-5-(trifluoromethyl)pyridine-2-carbonic acid prepared according to the process described in WO 2013/018928, N,O-dimethylhydroxyamine hydrochloride salt 1.9 g, and acetonitrile 100 mL, 1-ethyl-3-(3-dimethylaminopropyl)carbodiimide hydrochloride salt 4.6 g, 1-hydroxybenzotriazole 0.27 g, and triethylamine 5.5 mL were sequentially added at room temperature. The reaction mixtures were stirred at room temperature for 1 hour, thereto was added water, and the mixtures were extracted with ethyl acetate. The obtained organic layer was washed with water and brine, followed by dried over sodium sulfate and concentrated under reduced pressure. The obtained residue was subjected to a silica gel column chromatography to give the Intermediate compound (5-1) 4.8 g.

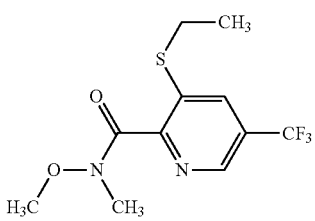

¹H-NMR (CDCl₃) δ: 8.67 (1H, s), 7.90 (1H, s), 3.58 (3H, s), 3.41 (3H, s), 3.00 (2H, q), 1.34 (3H, t).

Preparation Example 5(2)

To the mixture of the Intermediate compound (5-1) 0.60 g and tetrahydrofuran 8 mL, 1M THF solution of methylmagnesium bromide 2.5 mL was added under ice-cooling. The reaction mixtures were stirred at room temperature for 2 hours, thereto was added 2N hydrochloric acid, and the mixtures were extracted with ethyl acetate. The obtained organic layer was washed with water and brine, followed by dried over anhydrous sodium sulfate and concentrated under reduced pressure. The obtained residue was subjected to a silica gel column chromatography to give the Intermediate compound (5-2) 3.7 g.

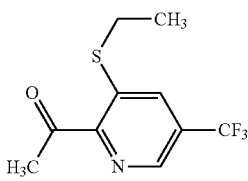

¹H-NMR (CDCl₃) δ: 8.62 (1H, d), 7.84 (1H, d), 2.96 (2H, q), 2.74 (3H, s), 1.42 (3H, t).

Preparation Example 5(3)

The Intermediate compound (5-3) was prepared according to the method described in Preparation example 2(3) using the Intermediate compound (5-2) instead of the Intermediate compound (4-2).

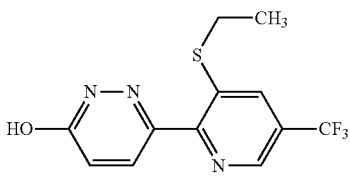 [SMILES: CCSc1cc(C(F)(F)F)cnc1-c1ccc(O)nn1]

¹H-NMR (CDCl₃) δ: 10.94 (1H, br s), 8.64 (1H, d), 8.21 (1H, d), 7.85 (1H, d), 7.08 (1H, d), 2.99 (2H, q), 1.39 (3H, t).

Preparation Example 5(4)

To 2.7 g of the Intermediate compound (5-3), phosphorus oxychloride 10 mL was added, and the mixtures were stirred at 100° C. for 6 hours. After it was confirmed that TLC indicated the consumption of the Intermediate compound 3, the mixtures were concentrated under reduced pressure with an evaporator, followed by to the obtained residue was added saturated sodium hydrogen carbonate solution under ice-cooling, and the mixtures were then extracted with MTBE. The obtained organic layer was washed with brine, followed by dried over anhydrous sodium sulfate and concentrated under reduced pressure. The obtained residue was subjected to a silica gel column chromatography to give the Intermediate compound (5-4) 1.73 g.

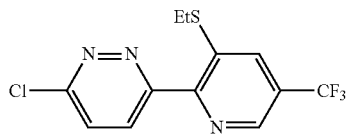

¹H-NMR (CDCl₃) δ: 8.69 (1H, s), 8.34 (1H, d), 7.94 (1H, s), 7.68 (1H, d), 3.00 (2H, q), 1.38 (3H, t).

Preparation Example 5(5)

The Intermediate compound (5-5) was prepared according to the method described in Preparation example 2(5) using the Intermediate compound (5-4) instead of the Intermediate compound (4-4).

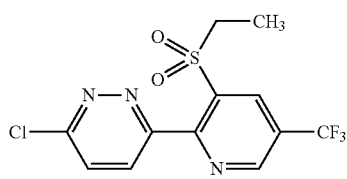 [SMILES: CCS(=O)(=O)c1cc(C(F)(F)F)cnc1-c1ccc(Cl)nn1]

¹H-NMR (CDCl₃) δ: 9.18 (1H, d), 8.78 (1H, d), 8.01 (1H, d), 7.76 (1H, d), 3.96 (2H, q), 1.45 (3H, t).

Preparation Example 5(6)

To the mixture of the Intermediate compound (5-5) 0.24 pentafluoropropanol 0.10 mL was added at room temperature. The reaction mixtures were stirred at 60° C. for 1 hour. After the obtained mixtures were allowed to stand to room temperature, thereto was added water, and the mixtures were extracted with ethyl acetate. The obtained organic layer was washed with water and brine, followed by dried over anhydrous sodium sulfate and concentrated under reduced pressure. The obtained residue was subjected to a silica gel column chromatography to give Present compound 28.

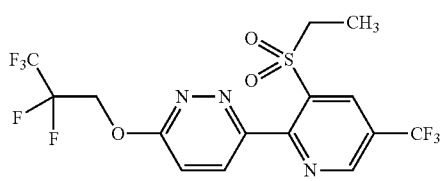

¹H-NMR (CDCl₃) δ: 9.16 (1H, s), 8.77 (1H, s), 8.01 (1H, d), 7.32 (1H, d), 5.10 (2H, t), 3.96 (2H, q), 1.44 (3H, t).

The present compound was prepared according to the method described in Preparation example 5(6) using the compound represented by Formula R¹-OH instead of 2,2,3,3-pentafluoropropanol and is shown in Table 22.

TABLE 22

| Present compound No. | R¹ |
| --- | --- |
| 31 | CF₂HCF₂CH₂ |
| 32 | CF₃CHFCF₂CH₂ |

Present compound 31; ¹H-NMR (CDCl₃) δ: 9.16 (1H, s), 8.77 (1H, s), 8.00 (1H, d), 7.30 (1H, d), 6.18-5.93 (1H, m), 5.03 (2H, t), 3.96 (2H, q), 1.44 (3H, t).

Present compound 32; ¹H-NMR (CDCl₃) δ: 8.68 (1H, s), 8.39 (1H, d), 7.92 (1H, s), 7.24 (1H, s), 5.07 (3H, m 4.15-4.08 (1H, q), 1.39 (3H, t).

Preparation Example 6

Present compound 39 was prepared according to the method described in Preparation example 5(6) using the Intermediate compound (5-4) instead of the Intermediate compound (5-5).

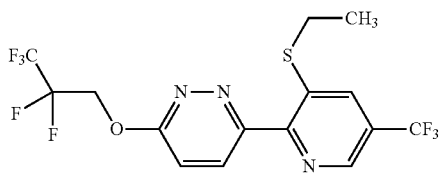 [SMILES: CCSc1cc(C(F)(F)F)cnc1-c1ccc(OCC(F)(F)C(F)(F)F)nn1]

¹H-NMR (CDCl₃) δ: 8.68 (1H, d), 8.40 (1H, d), 7.93 (1H, d), 7.28 (1H, d), 5.17-5.11 (2H, m), 3.01 (2H, q), 1.39 (3H, t).

Preparation Example 7

Present compound 40 was prepared according to the method described in Preparation example 5(6) using the Intermediate compound (5-4) intead of the Intermediate compound (5-5) and 2,2,3,3-tetrafluoropropanol instead of 2,2,3,3-pentafluoropropanol.

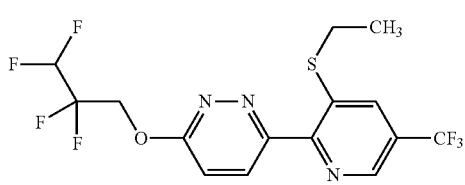 [SMILES: CCSc1cc(C(F)(F)F)cnc1-c1ccc(OCC(F)(F)C(F)F)nn1]

¹H-NMR (CDCl₃) δ: 8.68 (1H, d), 8.38 (1H, d), 7.92 (1H, d), 7.25 (1H, d), 6.05 (1H, tt), 5.10-5.03 (2H, m), 3.01 (2H, q), 1.39 (3H, t).

Preparation Example 8

To the mixure of 1.0 g of Intermediate (4-4), cesium carbonate 1.8 g, and NMP 7 mL, 2,2,3,3,3-pentafluoropropanol 1.6 mL was added at room temperature. The mixtures were heated and stirred at 70° C. for 47 hours. After the obtained mixtures were allowed to stand to room temperature, thereto was added water, and the mixtures were then extracted with ethyl acetate. The obtained organic layer was washed with water and brine, followed by dried over anhydrous sodium sulfate and concentrated under reduced pressure. The obtained residue was subjected to a silica gel column chromatography to give 1.3 g of Present compound 27.

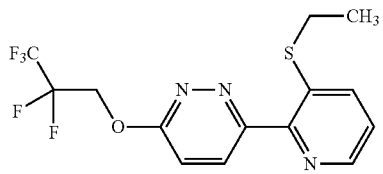 [SMILES: CCSc1cccnc1-c1ccc(OCC(F)(F)C(F)(F)F)nn1]

¹H-NMR (CDCl₃) δ: 8.46 (1H, dd), 8.32 (1H, d), 7.78 (1H, dd), 7.32 (1H, dd), 7.24 (1H, d), 5.12 (2H, t), 2.96 (2H, q), 1.35 (3H, t).

Preparation Example 9

To the mixure of 790 mg of Present compound 27, and chloroform 7 mL, 75% mCPBA 510 mg was added under ice-cooling. The mixtures were stirred under ice-cooling for 0.5 hours. To the obtained reaction mixtures, saturated sodium hydrogen carbonate solution was added, and the mixtures were extracted with chloroform. The obtained organic layer was washed with brine, followed by dried over anhydrous sodium sulfate and concentrated under reduced pressure. The obtained residue was subjected to a silica gel column chromatography to give 780 mg of Present compound 29.

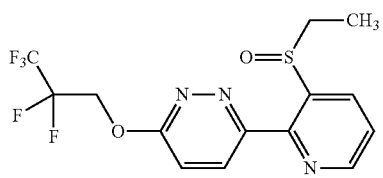

¹H-NMR (CDCl₃) δ: 8.78 (1H, dd), 8.68 (1H, dd), 8.60 (1H, d), 7.64 (1H, dd), 7.30 (1H, d), 5.21-5.02 (2H, m), 3.54-3.42 (1H, m), 3.06-2.95 (1H, m), 1.41 (3H, t).

Preparation Example 10

The mixture of N-oxide 3 0.45 g, paradium carbon 50 mg, ammonium formate 0.66 g, and methanol 3 ml was stirred at room temperature for 10 minutes. The mixtures was warmed to 60° C. and heated to stir for 2 hours. The obtained mixtures were allowed to stand to room temperature, thereto was added water, and the mixtures were extracted with ethyl acetate. The obtained organic layer was washed with brine, followed by dried over anhydrous sodium sulfate and concentrated under reduced pressure. The obtained residue was subjected to a silica gel column chromatography to give 200 mg of Present compound 30.

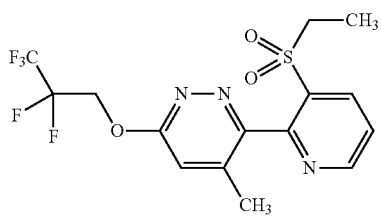

¹H-NMR (CDCl₃) δ: 8.94 (1H, dd), 8.48 (1H, dd), 7.65 (1H, dd), 7.10 (1H, m), 5.03 (2H, dt), 3.46 (2H, q), 2.22 (3H, t), 1.31 (3H, t).

Preparation Example 11(1)

The solution of the Intermediate compound (4-2) 0.5 g and THF 3 mL was cooled to −78° C., and to the solution, LDA 2.7 mL (1.1 M THF solution) was added dropwise. After stirring for 1 hour, to the mixtures, ethyl trifluoropyruvate 0.53 mL was added, and the mixtures were stirred for 30 minutes. To the obtained mixtures, saturated ammonium chloride solution was added at room temperature, and the mixtures were extracted with MTBE. The obtained organic layer was washed with brine, followed by dried over anhydrous sodium sulfate and concentrated under reduced pressure. The obtained residue was subjected to a silica gel column chromatography to give 0.74 g of the Intermediate compound (11-1).

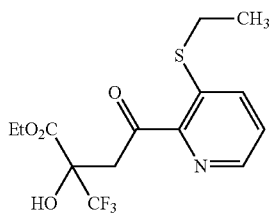

$^1$H-NMR (CDCl$_3$) δ: 8.41 (1H, dd), 7.69 (1H, dd), 7.40 (1H, dd), 4.56 (1H, br s), 4.45-4.32 (2H, m), 4.16-4.08 (2H, m), 2.92 (2H, q), 1.39 (3H, t), 1.30 (3H, t).

Preparation Example 11(2)

To the solution of the Intermediate compound (11-1) 0.74 g and ethanol 10 mL, 12 N hydrochloric acid 0.10 mL and hydrazine monohydrate 0.21 mL was added dropwise. After stirring at 80° C. for 10 hours, the mixtures were concentrated under reduced pressure with an evaporator. The obtained residue was subjected to a silica gel column chromatography to give 0.25 g of the Intermediate compound (11-2).

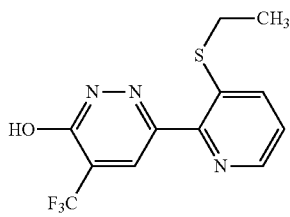 [SMILES: CCSc1cccnc1-c1cc(C(F)(F)F)c(O)nn1]

$^1$H-NMR (CDCl$_3$) δ: 10.71 (1H, s), 8.55 (1H, s), 8.45 (1H, dd), 7.74 (1H, dd), 7.33 (1H, dd), 2.97 (2H, q), 1.37 (3H, t).

Preparation Example 11(3)

To 0.579 g of the Intermediate compound (11-2), phosphorus oxychloride 10 mL was added, and the mixtures were stirred 100° C. for 6 hours. After it was confirmed that TLC indicated the consumption of the Intermediate compound (11-2), the mixtures were concentrated under reduced pressure with an evaporator, and to the obtained residue was added saturated sodium hydrogen carbonate solution under ice-cooling, and the mixtures were extracted with MTBE. The obtained organic layer was washed with brine, followed by dried over anhydrous sodium sulfate and concentrated under reduced pressure. The obtained residue was subjected to a silica gel column chromatography to give 0.51 g of the Intermediate compound (11-3).

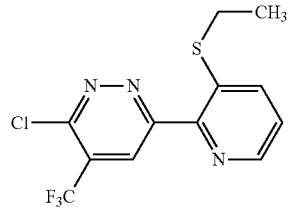 [SMILES: CCSc1cccnc1-c1cc(C(F)(F)F)c(Cl)nn1]

$^1$H-NMR (CDCl$_3$) δ: 8.65 (1H, s), 8.51 (1H, dd), 7.83 (1H, dd), 7.39 (1H, dd), 2.99 (2H, q), 1.35 (3H, t).

Preparation Example 11(4)

To the solution of the Intermediate compound (11-3) 0.26 g and NMP 3 mL, 2,2,3,3,3-pentafluoroalcohol 0.11 mL and cesium carbonate 0.36 g were added, and the mixtures were then heated and stirred at 70° C. for 2 hours. To the obtained reaction mixtures, saturated ammonium chloride solution was added at room temperature, and the mixtures were extracted with MTBE. The obtained organic layer was washed with brine, followed by dried over anhydrous sodium sulfate and concentrated under reduced pressure. The obtained residue was dissolved in chloroform 5 mL, and thereto was added 75% mPBA 0.41 g under ice-cooling, and the mixtures were stirred for 1 hour. To the obtained reaction mixtures, saturated sodium hydrogen carbonate solution and sodium thiosulfate solution were added at room temperature, and the mixtures were then extracted with chloroform. The obtained organic layer was washed with brine, followed by dried over anhydrous sodium sulfate and concentrated under reduced pressure. The obtained residue was subjected to a silica gel column chromatography to give 0.20 g of Present compound 34.

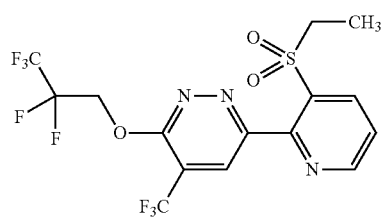

$^1$H-NMR (CDCl$_3$) δ: 8.95 (1H, dd), 8.56 (1H, dd), 8.22 (1H, s), 7.70-7.66 (1H, m), 5.21-5.15 (2H, m), 3.88 (2H, q), 1.43 (3H, dt).

Preparation Example 12

Present compound 33 was prepared according to the method described in Preparation example 11(4) using 2,2,3,3-tetrafluoropropanol instead of 2,2,3,3,3-pentafluoropropanol.

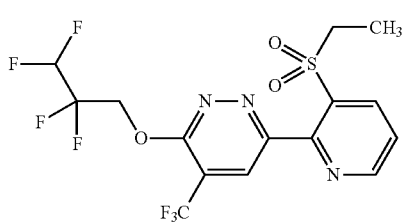

¹H-NMR (CDCl₃) δ: 8.96-8.94 (1H, m), 8.56 (1H, dd), 8.21 (1H, s), 7.67 (1H, dd), 6.19-5.91 (1H, m), 5.11 (2H, t), 3.93-3.85 (2H, m), 1.43 (3H, t).

Preparation Example 13(1)

The solution of the Intermediate compound (4-2) 5.0 g and THF 25 mL was cooled to −78° C., and thereto was added LDA 27 mL (1.1 M THF solution). After stirring for 30 minutes, to the mixtures was added ethyl pyruvate 6.1 mL, and the mixtures were stirred for 30 minutes. To the obtained reaction mixtures, saturated ammonium chloride solution was added at room temperature, and the mixtures were extracted with MTBE. The obtained organic layer was washed with brine, followed by dried over anhydrous sodium sulfate and concentrated under reduced pressure. The obtained residue was subjected to a silica gel column chromatography to give 4.2 g of the Intermediate compound (13-1).

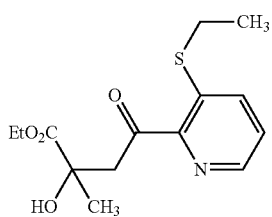 [SMILES: CCOC(=O)C(C)(O)CC(=O)c1ncccc1SCC]

¹H-NMR (CDCl₃) δ: 8.40 (1H, dd), 7.69 (1H, dd), 7.38 (1H, dd), 4.29 (1H, s), 4.23 (2H, q), 3.86 (1H, d), 3.61 (1H, d), 2.91 (2H, q), 1.52 (3H, s), 1.39 (3H, t), 1.30-1.22 (3H, m).

Preparation Example 13(2)

To the solution of the Intermediate compound (13-1) 4.2 g and ethanol 55 mL, 2 N hydrochloric acid 2.0 mL and hydrazine monohydrate 1.36 mL were added dropwise. The mixtures were stirred at 60° C. for 10 hours and concentrated under reduced pressure with an evaporator. The obtained residue was subjected to a silica gel column chromatography to give 2.1 g of the Intermediate compound (13-2).

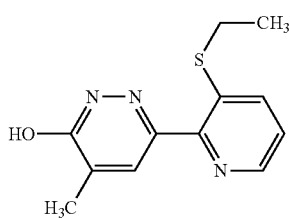

¹H-NMR (CDCl₃) δ: 10.70 (1H, s), 8.43 (1H, dd), 7.93 (1H, q), 7.71 (1H, dd), 7.28 (1H, dd), 2.94 (2H, q), 2.29 (3H, d), 1.34 (3H, t).

Preparation Example 13(3)

To the Intermediate compound (13-2) 2.0 g and phosphorus oxychloride 9 mL, toluene 30 mL was added, and the mixtures were stirred at 100° C. for 4 hours. After it was confirmed that TLC indicated the consumption of Intermediate (13-2), the mixtures weres concentrated under reduced pressure with an evaporator, and to the obtained residue was added saturated sodium hydrogen carbonate solution under ice-cooling, and the mixtures were extracted with MTBE. The obtained organic layer was washed with brine, followed by dried over anhydrous sodium sulfate and concentrated under reduced pressure. The obtained residue was subjected to a silica gel column chromatography to give 1.9 g of the Intermediate compound (13-3).

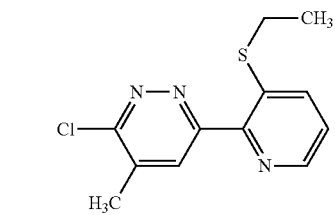

¹H-NMR (CDCl₃) δ: 8.47 (1H, dd), 8.10 (1H, d), 7.79 (1H, dd), 7.33 (1H, dd), 2.95 (2H, q), 2.49 (3H, d), 1.33 (3H, t).

Preparation Example 13(4)

To the solution of Intermediate (13-3) 0.92 g and NMP mL, 2,2,3,3-tetrafluoropropanol 0.46 mL and cesium carbonate 1.57 g were added, and the mixtures were then heated to 70° C. and stirred for 4 hours. To the obtained mixtures, saturated ammonium chloride solution was added at room temperature, and the mixtures were extracted with MTBE. The obtained organic layer was washed with brine, followed by dried over anhydrous sodium sulfate and concentrated under reduced pressure. The obtained residue was dissolved in chloroform 20 mL, thereto was added mCPBA 1.7 g under ice-cooling, and the mixtures were stirred for 1 hour. To the obtained reaction mixtures, saturated sodium hydrogen carbonate solution and sodium thiosulfate solution were added at room temperature, and the mixtures were extracted with chloroform. The obtained organic layer was washed with brine, followed by dried over anhydrous sodium sulfate and concentrated under reduced pressure. The obtained residue was subjected to a silica gel column chromatography to give 0.25 g of Present compound 37 and 0.73 g of Present compound 35.

Present Compound 37

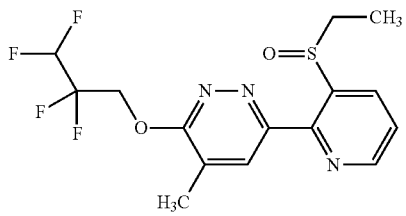 [SMILES: CCS(=O)c1cccnc1-c1cc(C)c(OCC(F)(F)C(F)F)nn1]

¹H-NMR (CDCl₃) δ: 8.45 (1H, dd), 8.08 (1H, d), 7.77 (1H, dd), 7.31 (1H, dd), 6.03 (1H, tt), 5.04 (2H, ddd), 2.95 (2H, q), 2.34 (3H, d), 1.34 (3H, t).

Present Compound 35

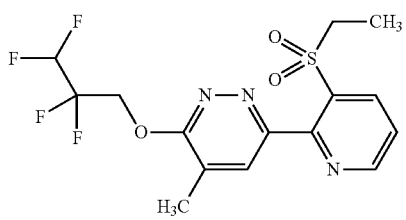 [SMILES: CCS(=O)(=O)c1cccnc1-c1cc(C)c(OCC(F)(F)C(F)F)nn1]

¹H-NMR (CDCl₃) δ: 8.91 (1H, s), 8.52 (1H, dd), 7.73 (1H, s), 7.62 (1H, dd), 6.03 (1H, tt), 5.00 (2H, t), 3.89 (2H, q), 2.35 (3H, d), 1.40 (3H, t).

Preparation Example 14

Present compound 38 and Present compound 36 were prepared according to the method described in Preparation example 13(4) using 2,2,3,3,3-pentafluoropropanol instead of 2,2,3,3-tetrafluoropropanol.

Present Compound 38

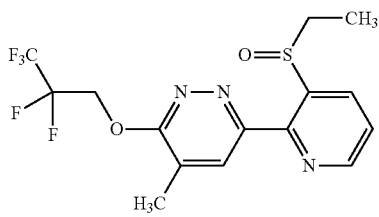 [SMILES: CCS(=O)c1cccnc1-c1cc(C)c(OCC(F)(F)C(F)(F)F)nn1]

¹H-NMR (CDCl₃) δ: 8.45 (1H, dd), 8.09 (1H, d), 7.77 (1H, dd), 7.31 (1H, dd), 5.11 (2H, td), 2.95 (2H, q), 2.35 (3H, d), 1.34 (3H, t).

Present Compound 36

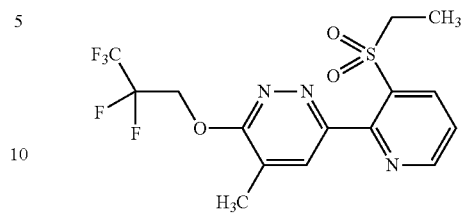

¹H-NMR (CDCl₃) δ: 8.91 (1H, dd), 8.52 (1H, dd), 7.74 (1H, s), 7.62 (1H, dd), 5.06 (2H, t), 3.89 (2H, q), 2.35 (3H, s), 1.40 (3H, t).

Preparation Example 15

To the solution of Present compound 9 500 mg and chloroform 2.5 mL, 75% mCPBA 610 mg was added under ice-cooling, and the mixtures were stirred for 24 hours. To the obtained reaction mixtures, saturated sodium hydrogen carbonate solution and sodium sulfite solution were added at room temperature, and the mixtures were extracted with chloroform. The obtained organic layer was washed with brine, followed by dried over anhydrous sodium sulfate and concentrated under reduced pressure. The obtained residue was subjected to a silica gel column chromatography to give 230 mg of N-oxide 1, and 300 mg of N-oxide 2.

N-Oxide 1

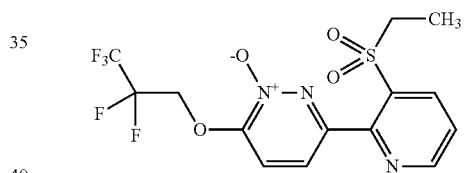

¹H-NMR (CDCl₃) δ: 8.94 (1H, dd), 8.39 (1H, dd), 7.73 (1H, d), 7.67 (1H, dd), 6.95 (1H, d), 4.99-4.76 (2H, m), 3.64-3.50 (2H, m), 1.39 (3H, t).

N-Oxide 2

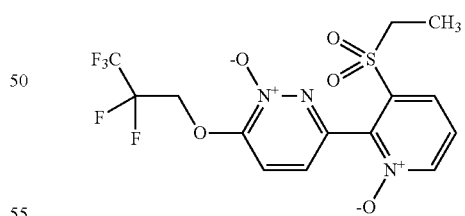

¹H-NMR (CDCl₃) δ: 8.50 (1H, dd), 7.91 (1H, dd), 7.74 (1H, d), 7.61 (1H, dd), 6.96 (1H, d), 4.86 (2H, t), 3.30-3.24 (2H, m), 1.31 (3H, t).

Preparation Example 16(1)

To the dispersion of sodium hydride (60%, oily) 3.44 g and DMF 50 mL, ethylmercaptan 6 mL was added dropwise under ice bath. After stirring under ice-cooling for 15 minutes, to the reaction mixtures was added 12 g of 1-(3-chloropyridin-2-yl)propan-1-one. The reaction mixtures were stirred at room temperature for 2 hours. To the obtained reaction mixtures, saturated sodium hydrogen carbonate solution was added at room temperature, and the mixtures were extracted with MTBE. The obtained organic layer was washed with water and brine, followed by dried over anhydrous sodium sulfate and concentrated under reduced pressure. The obtained residue was subjected to a silica gel column chromatography to give 14 g of the Intermediate compound (16-1).

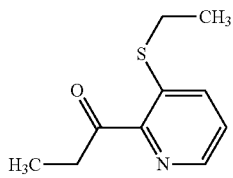

$^1$H-NMR (CDCl$_3$) δ: 8.39 (1H, dd), 7.69 (1H, dd), 7.36 (1H, dd), 3.22 (2H, q), 2.92 (2H, q), 1.39 (3H, t), 1.21 (3H, t).

Preparation Example 16(2)

To 2 N sodium hydroxide 12 mL, glyoxylic acid monohydrate 1.41 g was added under ice-cooling, and the mixtures were stirred for 10 minutes. To the reaction mixtures, MeOH 12 mL and 1.5 g of Intermediate (16-1) were added, and the mixtures were stirred for 1 hour. After it was confirmed that TLC indicated the consumption of Intermediate (16-1), to the reaction solution was added 12 N hydrochloric acid, and the mixtures were stirred for 1 hour, and the obtained solid was filtered and dried to give 1.3 g of the Intermediate compound (16-2).

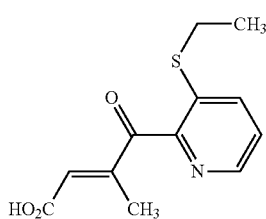 [SMILES: CCSc1cccnc1C(=O)/C(C)=C/C(=O)O]

$^1$H-NMR (CDCl$_3$) δ: 8.46 (1H, dd), 7.78 (1H, dd), 7.38 (1H, dd), 6.19 (1H, q), 2.93 (2H, q), 2.43 (3H, d), 1.33 (3H, t).

Preparation Example 16(3)

To the solution of the Intermediate compound (16-2) 0.10 g and water 3 mL, sodium sulfite 0.06 g was added, and the mixtures were stirred at 60° C. for 1 hour. After it was confirmed that TLC indicated the consumption of the Intermediate compound 2, to the reaction solution were added 12 N hydrochloric acid 1 mL and hydrazine monohydrate 0.05 mL, and the mixtures were warmed to 90° C. After stirring for 4 hours, the mixtures were slowly stirred under ice-cooling, and the formed crystal was filtered and dried to give 84 mg of the Intermediate compound (16-3).

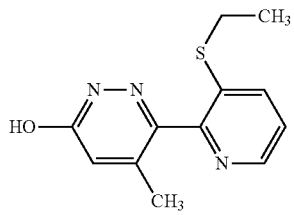 [SMILES: CCSc1cccnc1-c1nnc(O)cc1C]

$^1$H-NMR (CDCl$_3$) δ: 8.48 (1H, dt), 7.74 (1H, d), 7.33 (1H, ddd), 6.86 (1H, t), 2.89 (2H, q), 2.06 (3H, br s), 1.28 (3H, t).

Preparation Example 16(4)

To 7.4 g of the Intermediate compound (16-3), phosphorus oxychloride 10 mL was added, and the mixtures were stirred at 100° C. for 6 hours. After it was confirmed that TLC indicated the consumption of the Intermediate compound 3, the mixtures were concentrated under reduced pressure with an evaporator, and to the obtained residue was added saturated sodium hydrogen carbonate solution, and the mixtures were extracted with MTBE. The obtained organic layer was washed with brine, followed by dried over anhydrous sodium sulfate and concentrated under reduced pressure. The obtained residue was subjected to a silica gel column chromatography to give 5.7 g of the Intermediate compound (16-4).

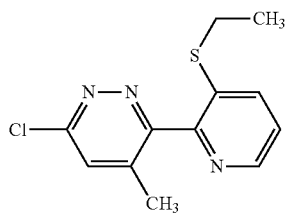 [SMILES: CCSc1cccnc1-c1nnc(Cl)cc1C]

$^1$H-NMR (CDCl$_3$) δ: 8.95 (1H, dd), 8.50 (1H, dd), 7.68 (1H, dd), 7.52 (1H, d), 3.48 (2H, q), 2.24 (3H, s), 1.31 (3H, t).

Preparation Example 16(5)

To the solution of the Intermediate compound (16-4) 5.7 g and chloroform 150 mL, mCPBA 11 g was added under ice-cooling, and the mixtures were stirred for 1 hour. To the obtained reaction mixtures, saturated sodium hydrogen carbonate solution and sodium thiosulfate solution were added at room temperature, and the mixtures were extracted with chloroform. The obtained organic layer was washed with brine, followed by dried over anhydrous sodium sulfate and concentrated under reduced pressure. The obtained residue was subjected to a silica gel column chromatography to give 2.3 g of the Intermediate compound (16-5).

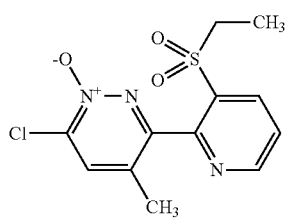

$^1$H-NMR (CDCl$_3$) δ: 9.00 (1H, dd), 8.43 (1H, dd), 7.69 (1H, dd), 7.17 (1H, d), 3.52-3.33 (2H, m), 2.10 (3H, d), 1.31 (3H, t).

Preparation Example 16(6)

To the solution of the Intermediate compound (16-5) 0.40 g and NMP 5 mL, 2,2,3,3,3-pentafluoropropanol 0.2 mL and cesium carbonate 0.57 g were added, and the mixtures were then heated to 70° C. and stirred for 2 hours. To the obtained reaction mixtures, saturated ammonium chloride solution was added at room temperature, and the mixtures were extracted with MTBE. The obtained organic layer was washed with brine, followed by dried over anhydrous sodium sulfate and concentrated under reduced pressure. The obtained residue was subjected to a silica gel column chromatography to give 0.45 g of N-oxide 3.

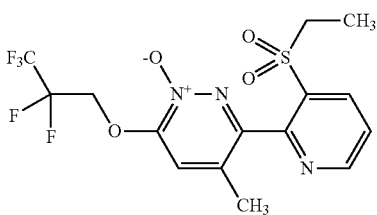

$^1$H-NMR (CDCl$_3$) δ: 9.00 (1H, dd), 8.43 (1H, dd), 7.70-7.66 (1H, m), 6.82 (1H, s), 4.94-4.75 (2H, m), 3.44 (2H, m), 2.08 (3H, s), 1.31 (3H, t).

Preparation Example 17

To the solution of Present compound 28 0.37 g and chloroform 5 mL, 75% mCPBA 0.22 g was added under ice-cooling, and the mixture was then stirred for 1 hour. To the obtained reaction mixtures, saturated sodium hydrogen carbonate solution and sodium thiosulfate solution were added at room temperature, and the mixtures were extracted with chloroform. The obtained organic layer was washed with brine, followed by dried over anhydrous sodium sulfate and concentrated under reduced pressure. The obtained residue was subjected to a silica gel column chromatography to give 0.25 g of N-oxide 4.

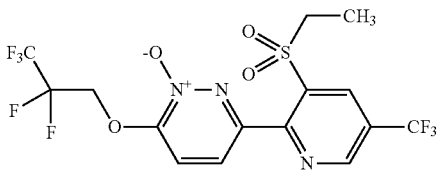

$^1$H-NMR (CDCl$_3$) δ: 9.18 (1H, d), 8.60 (1H, d), 7.74 (1H, d), 6.99 (1H, d), 4.98-4.79 (2H, m), 3.63 (2H, m), 1.42 (3H, t).

Preparation Example 18

N-oxide compound 5 was prepared according to the method described in Preparation example 17 using Present compound 31 instead of Present compound 28.

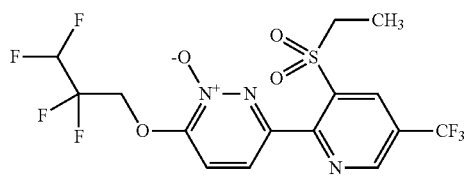

$^1$H-NMR (CDCl$_3$) δ: 9.18 (1H, d), 8.60 (1H, d), 7.73 (1H, d), 6.96 (1H, d), 6.13-5.87 (1H, m), 4.83 (2H, dd), 3.63 (2H, td), 1.42 (3H, t).

Next, the formulation examples of the present compound are shown below. The "parts" represents "part by weight".

Formulation Example 1

Into a mixture of 35 parts of xylene and 35 parts of DMF, 10 parts of any one of the Present compounds 1 to 40 and the N-oxides 1 to 5 is dissolved, and then 14 parts of polyoxyethylene styryl phenyl ether and 6 parts of calcium dodecylbenzene sulfonate are added thereto, followed by mixing them to obtain each formulation.

Formulation Example 2

Four(4) parts of sodium lauryl sulfate, 2 parts of calcium lignin sulfonate, 20 parts of synthetic hydrated silicon oxide fine powder and 54 parts of diatomaceous earth are mixed, and further 20 parts of any one of the Present compounds 1 to 40 and the N-oxides 1 to 5 is added thereto, followed by mixing them to obtain each wettable powders.

Formulation Example 3

To 2 parts of any one of the Present compounds 1 to 40 and the N-oxides 1 to 5, 1 part of synthetic hydrated silicon oxide fine powder, 2 parts of calcium lignin sulfonate, 30 parts of bentonite and 65 parts of kaolin clay are added and mixing. To the mixture is then added an appropriate amount of water, and the resulting mixture is further stirred, and subjected to granulation with a granulator, and forced-air drying to obtain each granular formulation.

Formulation Example 4

Into an appropriate amount of acetone, 1 part of any one of the Present compounds 1 to 40 and the N-oxides 1 to 5 is dissolved, and then 5 parts of synthetic hydrated silicon oxide fine powder, 0.3 parts of isopropyl acid phosphate and 93.7 parts of Fubasami clay are added thereto, followed by mixing with stirring thoroughly and removal of acetone from the mixture by evaporation to obtain each powder formulation.

Formulation Example 5

Thirty five (35) parts of a mixture of polyoxyethylene alkyl ether sulfate ammonium salt and white carbon (weight ratio of 1:1), 10 parts of any one of the Present compounds 1 to 40 and the N-oxides 1 to 5, and 55 parts of water are mixed, followed by finely grounding by a wet grinding method to obtain each flowable formulation.

Formulation Example 6

Into a mixture of 5 parts of xylene and 5 parts of trichloroethane, 0.1 parts of any one of the Present compounds 1 to 40 and the N-oxides 1 to 5 is dissolved, and the resulting mixture is then mixed with 89.9 parts of deodorized kerosene to obtain each oil solution.

Formulation Example 7

Into 0.5 mL of acetone, 10 mg of any one of the Present compounds 1 to 40 and the N-oxides 1 to 5 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of any one of the Present compounds 1 to 40 or the N-oxides 1 to 5 and 49.9 parts of Neothiozole (Chuo Kasei Co., Ltd.) are placed. After mounting an aerosol valve, 25 parts of dimethylether and 25 parts of LPG are filled, followed by shaking and further mounting an actuator to obtain each oily aerosol.

Formulation Example 9

A mixture of 0.6 part of any one of the Present compounds 1 to 40 and the N-oxides 1 to 5, 0.01 part of BHT (2,6-di-tert-butyl-4-methylphenol), 5 parts of xylene, 3.39 parts of deodorized kerosine and 1 part of an emulsifier {Rheodol MO-60 (manufactured by Kao Corporation)}, and 50 parts of distilled water are filled into an aerosol container, and a valve part is attached. Then, 40 parts of a propellant (LPG) is filled therein through the valve under pressure to obtain each aqueous aerosol.

Formulation Example 10

Zero point one (0.1) parts of any one of the Present compounds 1 to 40 and the N-oxides 1 to 5 is mixed into 2 mL of propylene glycol, and the resulting solution is impregnated into a porous ceramic plate having a size of 4.0 cm×4.0 cm and a thickness of 1.2 cm, to obtain each thermal fumigant.

Formulation Example 11

Five (5) parts of any one of the Present compounds 1 to 40 or the N-oxides 1 to 5, and 95 parts of ethylene-methyl methacrylate copolymer (the ratio of the methyl methacrylate in the copolymer: 10 weight %, Acryft (registered by trademark) WD 301, manufactured by Sumitomo Chemical Co. Ltd.) are melted and kneaded with a closed type pressure kneader (manufactured by Moriyama Manufacturing Co., Ltd.), and the resulting kneaded product is extruded from an extrusion molding machine through a molding die to obtain each rod-shaped molded product having a length of 15 cm and a diameter of 3 mm.

Formulation Example 12

Five (5) parts of any one of the Present compounds 1 to 40 and the N-oxides 1 to 5, and 95 parts of plasticized polyvinyl chloride resin are melted and kneaded with a closed type pressure kneader (manufactured by Moriyama Manufacturing Co., Ltd.), and the resulting kneaded product is extruded from an extrusion molding machine through a molding die to obtain each rod-shaped molded product having a length of 15 cm and a diameter of 3 mm.

Formulation Example 13

One-hundred(100) mg of any one of the Present compounds 1 to 40 and the N-oxides 1 to 5, 68.75 mg of lactose, 237.5 mg of corn starch, 43.75 mg of microcrystalline cellulose, 18.75 mg of polyvinylpyrrolidone, 28.75 mg of sodium carboxymethyl starch and 25 mg of magnesium stearate are mixed, and the resulting mixture is compressed to an appropriate size to obtain each tablet.

Formulation Example 14

Twenty-five(25) mg of any one of the Present compounds 1 to 40 and the N-oxides 1 to 5, 60 mg of lactose, 25 mg of corn starch, 6 mg of carmellose calcium and an appropriate amount of 5% of hydroxypropyl methylcellulose are mixed, and the resulting mixture is filled into a hard shell gelatin capsule or a hydroxypropyl methylcellulose capsule to obtain each capsule.

Formulation Example 15

To 100 mg of any one of the Present compounds 1 to 40 and the N-oxides 1 to 5, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum K (manufactured by Vanderbilt Co.), 35 mg of perfume, and 500 mg of coloring agent, distilled water is added so that a final volume is set to be 100 mL, followed by mixing them to obtain each suspension for oral administration.

Formulation Example 16

Into a mixture of 5% by weight of polysorbate 85, 3% by weight of benzyl alcohol and 30% by weight of propylene glycol, 5% by weight of any one of the Present compounds 1 to 40 and the N-oxides 1 to 5 is dissolved, and phosphate buffer is added thereto so that a pH of the solution is set to be 6.0 to 6.5, and then water is added as the rest part to obtain each solution for oral administration.

Formulation Example 17

To a mixture of 57% by weight of fractional distillated palm oil and 3% by weight of polysorbate 85, 5% by weight of aluminum distearate is added, and the mixture is heated to disperse it. The resulting mixture is cooled to room temperature, and 25% by weight of saccharin is dispersed in the oil vehicle. Ten(10) % by weight of any one of the Present compounds 1 to 40 and the N-oxides 1 to is divided thereto to obtain each paste for oral administration.

Formulation Example 18

Five(5) % by weight of any one of the Present compounds 1 to 40 and the N-oxides 1 to 5 is mixed with 95% by weight of limestone filler, followed by a wet-granulation of the resulting mixture to obtain each granule for oral administration.

Formulation Example 19

Into 80 parts of diethylene glycol monoethyl ether, 5 parts of any one of the Present compounds 1 to 40 and the N-oxides 1 to 5 is dissolved, and 15 parts of propylene carbonate are added thereto, and the resulting mixture is mixed to obtain each spot-on solution.

Formulation Example 20

Into 70 parts of diethylene glycol monoethyl ether, 10 parts of any one of the Present compounds 1 to 40 and the N-oxides 1 to 5 is dissolved, and 20 parts of 2-octyldodecanol are added thereto, and the resulting mixture is mixed to obtain each pour-on solution.

Formulation Example 21

To 0.5 parts of any one of the Present compounds 1 to 40 and the N-oxides 1 to 5, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly to obtain a homogeneous solution, and 19.5 parts of water is then added thereto and the resulting mixture is further mixed with stirring thoroughly to obtain each homogeneous solution of shampoo formulation.

Formulation Example 22

Zero point fifteen(0.15)% by weight of any one of the Present compounds 1 to 40 and the N-oxides 1 to 5, 95% by weight of animal feed, as well as 4.85% by weight of a mixture of dibasic calcium phosphate, diatomaceous earth, aerosol and carbonate (or chalk) are mixed with stirring thoroughly to obtain each premix for animal feed.

Formulation Example 23

Seven point two(7.2) g of any one of the Present compounds 1 to 40 and the N-oxides 1 to 5, and 92.8 g of Hosco (registered trademark) S-55 (manufactured by Maruishi Pharmaceuticals) are melted and mixed at 100° C., and the resulting mixture is poured into a suppository mold, followed by performing a cooling solidification to obtain each suppository.

Next, Test examples are used to show an efficacy of the present compounds on controlling harmful arthropods.

Test Example 1

Each formulation comprising the Present compound 4, 5, 6, 8, 9, 10, 14, 15, 17, 18, 19, 22, 23, 24, 25, 26, 27, 29, 31, 32, 33, 34, 35, 36, 37 or 38, or the N-oxide 2, the N-oxide 3, the N-oxide 4, or the N-oxide 5 prepared by the process according to the Formulation example 5 was diluted with water until each concentration of the active ingredient reached 500 ppm to prepare each test chemical solution.

Meanwhile, cucumber seedling (on the developmental stage of the first true leaf) was planted in a plastic cup, and approximately 30 heads of cotton aphid (*Aphis gossypii*) (all stages of life) were released onto the leaves of the cucumber and the seedling was left to stand for 1 day. The test chemical solution was sprayed into the seedling in a ratio of 20 mL/seedling.

After 6 days from the spraying, the number of the surviving cotton aphrid (*Aphris gossypii*) was investigated and the controlling value was calculated by the following equation.

Controlling value (%)={1−(Cb×Tai)/(Cai×Tb)}×100 wherein the symbols in the equation represent the following descriptions.

Cb: Number of the test insects before treatment in untreated group;

Cai: Number of the surviving insects at the time of the investigation in untreated group;

Tb: Number of the test insects before treatment in treated group;

Tai: Number of the surviving insects lived on the leaves at the time of the investigation in treated group;

Here the "untreated group" represents a group where a test chemical solution which was prepared by diluting a formulation prepared according to the Formulation example 5 except for not comprising present compound with the same amount of water as that used in the case of the treated group was sprayed. As a result, the treated group that was treated with each of the test chemical solution comprising the Present compound 4, 5, 6, 8, 9, 10, 14, 15, 17, 18, 19, 22, 23, 24, 25, 26, 27, 29, 31, 32, 33, 34, 35, 36, 37 or 38, or the N-oxide 2, the N-oxide 3, the N-oxide 4, or the N-oxide 5 showed 90% or greater as the controlling value.

Test Example 2

Each formulation comprising the Present compound 4, 5, 8, 9, 11, 14, 17, 22, 23, 24, 25, 27, 28, 29, 31, 32, 35, 36, 37 or 38, or the N-oxide 1, the N-oxide 2, the N-oxide 4, or the N-oxide 5 prepared by the process according to the Formulation example 5 was diluted with water until each concentration of the active ingredient reached 200 ppm to prepare each test chemical solution.

Meanwhile, cucumber seedling (on the developmental stage of the first true leaf) was planted in a plasticcup, and approximately 30 heads of cotton aphid (*Aphis gossypii*) (all stages of life) were released onto the leaves of the cucumber, and the seedling was left to stand for 1 day. The test chemical solution was sprayed into the seedling in a ratio of 20 mL/seedling.

After 6 days from the spraying, the number of the surviving cotton aphid lived on the leaves was investigated, and the controlling value was calculated by the following equation.

Controlling value (%)={1−(Cb×Tai)/(Cai×Tb)}×100 wherein the symbols in the equation represent the following descriptions.

Cb: Number of the test insects before treatment in untreated group;

Cai: Number of the surviving insects lived on the leaves at the time of the investigation in untreated group;

Tb: Number of the test insects before treatment in treated group;

Tai: Number of the surviving insects lived on the leaves at the time of the investigation in treated group;

Here the "untreated group" represents a group a test chemical solution which was prepared by diluting a formulation prepared according to the Formulation example 5 except for not comprising present compound with the same amount of water as that used in the case of the treated group was sprayed.

As a result, the treated group that was treated with each of the test chemical solution comprising the Present compound 4, 5, 8, 9, 11, 14, 17, 22, 23, 24, 25, 27, 28, 29, 31, 32, 35, 36, 37 or 38, or the N-oxide 1, the N-oxide 2, the N-oxide 4, or the N-oxide 5 showed 90% or greater as the controlling value.

Test Example 3

Each formulation comprising the Present compound 5, 6, 8, 9, 11, 14, 17, 25, 29, 31, 35, 36, 37 or 38, or the N-oxide 1, the N-oxide 2, or the N-oxide 4 prepared by the process according to the Formulation example 5 was diluted with water until each concentration of the active ingredient reached 200 ppm to prepare each test chemical solution.

Meanwhile, cucumber seedling (on the developmental stage of the second true leaf) was planted in a plastic cup, and 5 mL of each of the above test chemical solution was applied to the seedling by irrigation at plant foot, and the seedling was left to stand in a greenhouse at 25° C. for days. Approximately 30 heads of cotton aphid (Aphis gossypii) (all stages of life) were released onto the leaves of the cucumber, and the seedling was left to stand for additional 6 days in the greenhouse, followed by the number of the surviving insects was examined, and then the number of the surviving cotton aphid lived on the leaves of the cucumber was investigated, and the controlling value was calculated by the following equation.

Controlling value (%)={1−(Cb×Tai)/(Cai×Tb)}×100 wherein the symbols in the equation represent the following descriptions.

Cb: Number of the test insects before treatment in untreated group;

Cai: Number of the surviving insects lived on the leaves at the time of the investigation in untreated group;

Tb: Number of the test insects before treatment in treated group;

Tai: Number of the surviving insects lived on the leaves at the time of the investigation in treated group;

Here the "untreated group" represents a group where a test chemical solution which was prepared by diluting a formulation prepared according to the Formulation example 5 except for not comprising present compound with the same amount of water as that used in the case of the treated group was sprayed.

As a result, the treated group that was treated with each of the test chemical solution comprising the Present compounds 5, 6, 8, 9, 11, 14, 17, 25, 29, 31, 35, 36, 37 or 38, or the N-oxide 1, the N-oxide 2, or the N-oxide 4 showed 90% or greater as the controlling value.

Test Example 4

Each formulation comprising the Present compound 6, 8, 9, 14, 17, 22, 23, 25, 26, 27, 29, 31, 32, 35, 36, 37 or 38, or the N-oxide 4, or the N-oxide 5 prepared by the process according to the Formulation example 5 was diluted with water until each concentration of the active ingredient reached 500 ppm to prepare each test chemical solution.

Rice seedling (on the developmental stage of the second true leaf) was planted in a polyethylene cup, and 10 mL of each of the above test chemical solution was sprayed into the seedling. After air-drying the seedling, 20 heads of 3rd to 4th instar larvae of brown planthopper (Nilaparvata lugens) were released onto the rice leaves, and the seedling was left to stand at 25° C. in a greenhouse. After 6 days, the number of the surviving brown planthopper lived on the rice leaves was investigated, and the controlling value was calculated by the following equation.

Controlling value (%)={1−(Cb×Tai)/(Cai×Tb)}×100 wherein the symbols in the equation represent the following descriptions.

Cb: Number of the test insects before treatment in untreated group;

Cai: Number of the surviving insects lived on the leaves at the time of the investigation in untreated group;

Tb: Number of the test insects before treatment in treated group;

Tai: Number of the surviving insects lived on the leaves at the time of the investigation in treated group;

Here the "untreated group" represents a group where a test chemical solution which was prepared by diluting a formulation prepared according to the Formulation example 5 except for not comprising present compound with the same amount of water as that used in the case of the treated group was sprayed.

As a result, the treated group that was treated with each of the test chemical solution comprising the Present compound 6, 8, 14, 17, 22, 23, 25, 26, 27, 29, 31, 32, 35, 36, 37 or 38, or the N-oxide 4, or the N-oxide 5 showed 90% or greater as the controlling value.

Test Example 5

Each formulation comprising the Present compound 5, 6, 8, 9, 14, 17, 22, 23, 24, 25, 27, 28, 29, 31, 35, 36, 37 or 38, or the N-oxide 1, or the N-oxide 4 prepared by the process according to the Formulation example 5 was diluted with water until each concentration of the active ingredient reached 200 ppm to prepare each test chemical solution.

Rice seedling (on the developmental stage of the second true leaf) was planted in a polyethylene cup, and 10 mL of each of the above test chemical solution was sprayed into the seedling. After air-drying the seedling, 20 heads of 3rd to 4th instar larvae of brown planthopper (Nilaparvata lugens) were released onto the rice leaves, and the seedling was left to stand at 25° C. in a greenhouse. After 6 days, the number of the surviving brown planthopper lived on the rice leaves was investigated, and the controlling value was calculated by the following equation.

Controlling value (%)={1−(Cb×Tai)/(Cai×Tb)}×100 wherein the symbols in the equation represent the following descriptions.

Cb: Number of the test insects before treatment in untreated group;

Cai: Number of the surviving insects lived on the leaves at the time of the investigation in untreated group;

Tb: Number of the test insects before treatment in treated group;

Tai: Number of the surviving insects lived on the leaves at the time of the investigation in treated group;

Here the "untreated group" represents a group where a test chemical solution which was prepared by diluting a formulation prepared according to the Formulation example 5 except for not comprising present compound with the same amount of water as that used in the case of the treated group was sprayed.

As a result, the treated group that was treated with each of the test chemical solution comprising the Present compound 5, 6, 8, 9, 14, 17, 22, 23, 24, 25, 27, 28, 29, 31, 35, 36, 37 or 38, or the N-oxide 1, or the N-oxide 4 showed 90% or greater as the controlling value.

Test Example 6

Each formulation comprising the Present compound 4, 5, 6, 8; 9, 11, 14, 15, 17, 22, 23, 25, 28, 31, 35, 36, 37 or 38, or the N-oxide 1, the N-oxide 4, or the N-oxide 5 prepared by the process according to the Formulation example 5 was diluted with water until each concentration of the active ingredient reached 200 ppm to prepare each test chemical solution.

Meanwhile, rice seedling (on the developmental stage of the second true leaf at two weeks after seedling) was planted in a plastic cup, and 5 mL of each of the above test chemical solution was applied to the seedling by irrigation at plant foot and the seedling was left to stand at 25° C. in a greenhouse for 7 days. Twenty(20) heads of 3rd to 4th instar larvae of brown planthopper (Nilaparvata lugens) were released onto the rice leaves, and the seedling was left to stand for additional 6 days in the greenhouse, and then the number of the surviving brown planthopper lived on the rice leaves was investigated, and the controlling value was calculated by the following equation.

Controlling value (%)={1−($Cb×Tai$)/($Cai×Tb$)}×100 wherein the symbols in the equation represent the following descriptions.

Cb: Number of the test insects before treatment in untreated group;

Cai: Number of the surviving insects lived on the leaves at the time of the investigation in untreated group;

Tb: Number of the test insects before treatment in treated group;

Tai: Number of the surviving insects lived on the leaves at the time of the investigation in treated group;

Here the "untreated group" represents a group where a test chemical solution which was prepared by diluting a formulation prepared according to the Formulation example 5 except for not comprising present compound with the same amount of water as that used in the case of the treated group was sprayed.

As a result, the treated group that was treated with each of the test chemical solution comprising the Present compound 4, 5, 6, 8, 9, 11, 14, 15, 17, 22, 23, 25, 28, 31, 35, 36, 37 or 38, or the N-oxide 1, the N-oxide 4, or the N-oxide 5 showed 90% or greater as the controlling value.

Test Example 7

Each formulation comprising the Present compound 6, 8, 9, 10, 14, 15, 17, 18, 20, 21, 22, 23, 24, 25, 26, 27, 31, 32, 33, 34, 35, 36, 37 or 38, or the N-oxide 4, or the N-oxide 5 prepared by the process according to the Formulation example 5 was diluted with water until each concentration of the active ingredient reached 500 ppm to prepare each test chemical solution.

Meanwhile, cabbage seedling (on the developmental stage of the third true leaf) was planted in a polyethylene cup, and each of the test chemical solution was sprayed into the cabbage seedling in a ratio of 20 mL/cup. After the test chemical solution was dried, the stem and leaf thereof was cut out and then installed into a 50 mL cup. Five (5) heads of 2nd instar larvae of cabbage moth (Plutella xylostella) were released into the cup, and the cup was covered with a lid. After the cup was stored at 25° C. for 5 days, the number of the dead insects was counted, and the mortality of insects was calculated by the following equation.

Morality (%)=(1−the number of the dead insects/the number of the test insects)×100

As a result, the treated group that was treated with each of the test chemical solution of the Present compound 6, 8, 9, 10, 14, 15, 17, 18, 20, 21, 22, 23, 24, 25, 26, 27, 31, 32, 33, 34, 35, 36, 37 or 38, or the N-oxide 4, or the N-oxide 5 showed 80% or greater as the morality of insects.

Test Example 8

Each formulation comprising the Present compound 6, 8, 9, 10, 11, 14, 17, 18, 20, 22, 23, 24, 25, 26, 27, 28, 30, 31, 32, 33, 34, 35, 36 or 38, or the N-oxide 1, the N-oxide 4, or the N-oxide 5 prepared by the process according to the Formulation example 5 was diluted with water until each concentration of the active ingredient reached 200 ppm to prepare each test chemical solution.

Meanwhile, cabbage seedling (on the developmental stage of the third true leaf) was planted in a polyethylene cup, and each of the test chemical solution was sprayed into the cabbage seedling in a ratio of 20 mL/cup. After the test chemical solution was dried, the stem and leaf thereof was cut out and then installed into a 50 mL cup. Five (5) heads of 2nd instar larvae of cabbage moth (Plutella xylostella) were released into the cup, and the cup was covered with a lid. After the cup was stored at 25° C. for 5 days, the number of the dead insects was counted, and the mortality of insects was calculated by the following equation.

Morality (%)=(1−the number of the surviving insects/the number of the test insects)×100

As a result, the treated group that was treated with each of the test chemical solution comprising the Present compound 6, 8, 9, 10, 11, 14, 17, 18, 20, 22, 23, 24, 25, 26, 27, 28, 30, 31, 32, 33, 34, 35, 36 or 38, or the N-oxide 1, the N-oxide 4, or the N-oxide 5 showed 80% or greater as the morality of insects.

Test Example 9

Each formulation comprising the Present compound 5, 17, 25, 26, 27, 31, 35, 36, 37 or 38, or the N-oxide 3, the N-oxide 4, or the N-oxide 5 prepared by the process according to the Formulation example 5 was diluted with water until the concentration of the active ingredient reached 500 ppm to prepare a test chemical solution.

The bottom of the polyethylene cup having 5.5 cm diameter was matted with the same size of a filter paper, and 0.7 mL of the test chemical solution was added dropwise to the filter paper, and 30 mg sucrose as bait was placed in the cup uniformly. Ten (10) heads of female adult housefly (Musca domestica) were released into the polyethylene cup, and the cup was covered with a lid. After 24 hours, the life and death of housefly was investigated, and the number of dead insects was counted, and the mortality of insects was calculated by the following equation.

Mortality of insects (%)=(the number of dead insects/the number of test insects)×100

As a result, the treated group that was treated with each of the test chemical solution comprising the Present compound 5, 17, 25, 26, 27, 31, 35, 36, 37 or 38, or the N-oxide 3, the N-oxide 4, or the N-oxide 5 showed 100% as the morality of insects.

Test Example 10

The formulation comprising the Present compounds 4 prepared by the process according to the Formulation example 5 was diluted with water until the concentration of the active ingredient reached 500 ppm to prepare a test chemical solution.

Zero point seven(0.7) mL of the testg chemical solution was added to ion-changed water 100 ml (the concentrataion of the active ingredient was 3.5 ppm). Twenty (20) heads of the last instar larvae of female adult house mosquito (Culex pipiens pallens) were released on the leaves, and after 1 day, the life and death of house mosquito was investigated, and the number of dead insects was counted, and the mortality of insects was calculated by the following equation.

Mortality of insects (%)=(the number of the dead insects/the number of the test insects)×100

As a result, the treated group that was treated with the test chemical solution comprising the Present compound 4 showed 95% or greater as the morality of insects.

Test Example 11

Each formulation comprising the Present compound 1, 2, 4, 5, 6, 8, 9, 11, 15, 16, 17, 18, 19, 20, 21, 22, 23, 24, 25, 27, 28, 29, 31, 34 or 35, or the N-oxide 1, the N-oxide 2, the N-oxide 4, or the N-oxide 5 prepared by the process according to the Formulation example 1 was diluted with water until each concentration of the active ingredient reached 50 ppm to prepare each test chemical solution.

Meanwhile, cucumber seedling (on the developmental stage of the third true leaf) was planted in a polyethylene cup, and each of the test chemical solution was sprayed into the seedling in a ratio of 30 mL/cup. After the test chemical solution was dried, the second leaf thereof was cut out, and then installed into a 200 mL cup. Ten (10) heads of the second instar larvae of cucurbit leaf beetle (Aulacophora femoralis) were released into the cup, and the cup was covered with a lid. After the cup was stored at 25° C. for 5 days, the number of the dead insects was counted, and the mortality of insects was calculated by the following equation.

Morality (%)={the number of the dead insects/the number of the test isects}×100

As a result, the treated group that was treated with each of the test chemical solution comprising the Present compound 1, 2, 4, 5, 6, 8, 9, 11, 15, 16, 17, 18, 19, 20, 21, 22, 23, 24, 25, 27, 28, 29, 31, 34 or 35, or the N-oxide 1, the N-oxide 2, the N-oxide 4, or the N-oxide 5 showed 85% or greater as the morality of insects.

Test Example 12

Each 1 mg of any one of the present compounds is dissolved into the mixed solution of acetone and polyoxyethylene sorbitan mono-cocoate (acetone and polyoxyethylene sorbitan mono-cocoate=95:5 (weight ratio)) in a ratio of 50 µL of the mixed solution per 1 mg of the present compound. Thereto is added ion-exchanged water containing 0.03% (v/v) of Sindain (registered trademark, manufactured by Sumitomo Chemical Company, Limited) until each concentration of the present compound reached 200 ppm to prepare each diluted solution.

Corns (Zea mays) are sown on a tray overlaid with damped KimWipes. After corns are grown for 5 days, the entire seedling of the corn is immersed into the diluted solution for 30 seconds. After drying, each two grains of the seedling are installed in a plastic petri dish (90 mm radius), and 10 heads of the second instar larvae of Western corn rootworm (Diabrotica virgifera virgifera) are released onto the cup and the cup is covered with a lid. After the cup is stored at 25° C. for 5 days, the number of the dead insects is counted, and the mortality of insects is calculated by the following equation.

Morality (%)={the number of the deadinsects/10}×100

In the test, the following present compounds showed 80% or greater as the morality of insects.
Present compounds: 33, 34, and 38

INDUSTRIAL APPLICABILITY

The present compounds show an excellent control effect against a harmful arthropod.

The invention claimed is:
1. A pyridazine compound represented by formula (1):

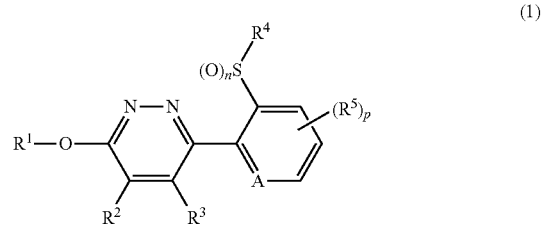

wherein,
A represents a nitrogen atom or a $CR^6$;
$R^1$ represents a C2-C10 alkyl group, a C3-C10 alkenyl group, a C3-C10 alkynyl group, a (C1-C5 alkyl)-O—(C2-C5 alkyl) group, a (C3-C5 alkenyl)-O—(C2-C5 alkyl) group, a (C3-C5 alkynyl)-O—(C2-C5 alkyl) group, a (C1-C5 alkyl)-S(O)$_m$—(C2-C5 alkyl) group, a (C3-C5 alkenyl)-S(O)$_m$—(C2-C5 alkyl) group, a (C3-C5 alkynyl)-S(O)$_m$—(C2-C5 alkyl) group, or a (C1-C5 alkyl)-C(O)—(C1-C5 alkyl) group, wherein $R^1$ has one or more halogen atoms;
$R^2$ and $R^3$ represent independently of each other a hydrogen atom, a C1-C6 alkyl group optionally having one or more halogen atoms, a C2-C6 alkoxycarbonyl group, a cyano group, or a halogen atom;
$R^4$ represents a C1-C6 chain hydrocarbon group optionally having one or more halogen atoms;
$R^5$ represents a C1-C6 chain hydrocarbon group optionally having one or more halogen atoms, a phenyl group optionally having one or more atoms or groups selected from Group A, a 5-membered aromatic heterocyclic group selected from Group B, wherein said 5-membered aromatic heterocyclic group may optionally have one or more atoms or groups selected from Group A, a 6-membered aromatic heterocyclic group selected from Group C, wherein said 6-membered aromatic heterocyclic group may optionally have one or more atoms or groups selected from Group A, a 3 to 7 membered nonaromatic heterocyclic group selected from Group D, wherein the 3 to 7 membered nonaromatic heterocyclic group may optionally have one or more atoms or groups selected from the group consisting of a halogen atom and a C1-C6 alkyl group, a $OR^7$, a $NR^8R^9$, a $NR^8C(O)R^{10}$, a $NR^8C(O)OR^{11}$, a $NR^8C(O)NR^{12}R^{13}$, a N=CHNR$^{12}$R$^{13}$, a N=S(O)R$^{12}$R$^{13}$, a S(O)$_x$R$^{12}$, a C(O)OR$^8$, a cyano group, or a halogen atom;
$R^6$ represents a hydrogen atom, or a halogen atom;
$R^7$ represents a hydrogen atom, a C1-C6 alkyl group, a C3-C6 alkenyl group, a C3-C6 alkynyl group, a (C1-C3 alkyl)-O—(C1-C3 alkyl) group, a (C1-C3 alkyl)-S(O)$_y$—(C1-C3 alkyl) group, a C3-C7 cycloalkyl group, a (C3-C7 cycloalkyl)-(C1-C3 alkyl) group, wherein said C1-C6 alkyl group, said C3-C6 alkenyl group, said C3-C6 alkynyl group, said (C1-C3 alkyl)-O—(C1-C3 alkyl) group, said (C1-C3 alkyl)-S(O)$_y$—(C1-C3 alkyl) group, said C3-C7 cycloalkyl group, and said (C3-C7 cycloalkyl)-(C1-C3 alkyl) group may optionally have one or more halogen atoms, or a phenyl C1-C3 alkyl group, wherein the phenyl moiety in said phenyl C1-C3 alkyl group may optionally have one or more atoms or groups selected from Group A;

$R^8$ represents a hydrogen atom, a C1-C6 alkyl group optionally having one or more halogen atoms, a C3-C6 alkenyl group optionally having one or more halogen atoms, or a C3-C6 alkynyl group optionally having one or more halogen atoms;

$R^9$ represents a hydrogen atom, a C1-C6 alkyl group, a C3-C6 alkenyl group, a C3-C6 alkynyl group, a (C1-C3 alkyl)-O—(C1-C3 alkyl) group, a (C1-C3 alkyl)-S(O)$_y$—(C1-C3 alkyl) group, a C3-C7 cycloalkyl group, a (C3-C7 cycloalkyl)-(C1-C3 alkyl) group, wherein said C1-C6 alkyl group, said C3-C6 alkenyl group, said C3-C6 alkynyl group, said (C1-C3 alkyl)-O—(C1-C3 alkyl) group, said (C1-C3 alkyl)-S(O)$_y$—(C1-C3 alkyl) group, said C3-C7 cycloalkyl group, and said (C3-C7 cycloalkyl)-(C1-C3 alkyl) group may optionally have one or more halogen atoms, a cyano C1-C6 alkyl group, a phenyl C1-C3 alkyl group, wherein the phenyl moiety in said phenyl C1-C3 alkyl group may optionally have one or more atoms or groups selected from Group A, or a (5 or 6 membered heteroaryl)C1-C3 alkyl group, wherein the 5 or 6 membered heteroaryl moiety in said (5 or 6 membered heteroaryl)C1-C3 alkyl group may optionally have one or more atoms or groups selected from Group A;

$R^{10}$ represents a hydrogen atom, a C1-C6 alkyl group, a C3-C6 alkenyl group, a C3-C6 alkynyl group, a C3-C7 cycloalkyl group, a (C3-C7 cycloalkyl)-(C1-C3 alkyl) group, wherein said C1-C6 alkyl group, said C3-C6 alkenyl group, said C3-C6 alkynyl group, said C3-C7 cycloalkyl group, and said (C3-C7 cycloalkyl)-(C1-C3 alkyl) group may optionally have one or more halogen atoms, or a phenyl C1-C3 alkyl group, wherein the phenyl moiety in said phenyl C1-C3 alkyl group may optionally have one or more atoms or substituents selected from Group A;

$R^{11}$ represents a C1-C6 alkyl group optionally having one or more halogen atoms, a C3-C6 alkenyl group optionally having one or more halogen atoms, a C3-C6 alkynyl group optionally having one or more halogen atoms, a C3-C7 cycloalkyl group optionally having one or more halogen atoms, a (C3-C7 cycloalkyl)-(C1-C3 alkyl) group optionally having one or more halogen atoms, wherein said (C3-C7 cycloalkyl)-(C1-C3 alkyl) group may optionally have one or more halogen atoms, or a phenyl C1-C3 alkyl group, wherein the phenyl moiety in said phenyl C1-C3 alkyl group may optionally have one or more atoms or groups selected from Group A;

$R^{12}$ and $R^{13}$ represent independently of each other a C1-C6 alkyl group optionally having one or more halogen atoms;

$R^{14}$ represents a hydrogen atom, a C1-C6 alkyl group optionally having one or more halogen atoms, a C2-C6 alkylcarbonyl group optionally having one or more halogen atoms, or a C2-C6 alkoxycarbonyl group optionally having one or more halogen atoms;

n represents 0, 1, or 2;

m represents 0, 1, or 2;

p represents 0, 1, 2, or 3, wherein when p represents 2 or 3, a plurality of $R^5$ may be identical or different;

x represents 0 or 1;

y represents 0, 1, or 2;

Group A: a group consisting of a C1-C6 alkyl group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a cyano group, and a halogen atom;

Group B:

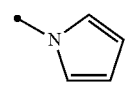

B-1

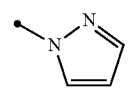

B-2

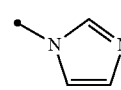

B-3

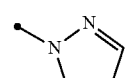

B-4

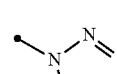

B-5

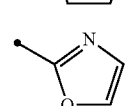

B-6

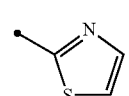

B-7

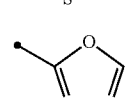

B-8

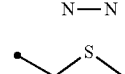

B-9

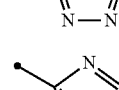

B-10

Group C:

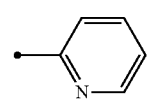

C-1

-continued

C-1 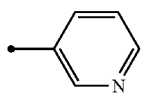

C-2 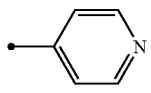

C-3 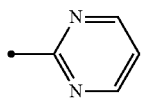

C-4 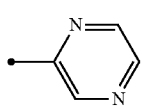

C-5 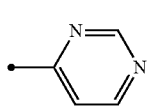

C-6 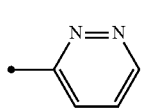

C-7 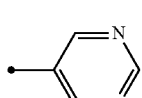

C-8 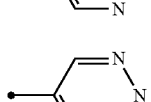

Group D:

D-1 

D-2 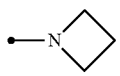

D-3 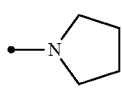

D-4 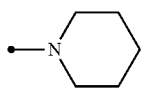

D-5 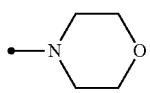

D-6 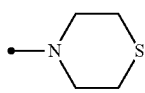

D-7 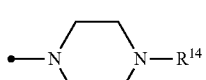

-continued

C-2 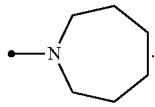

2. The compound according to claim 1, wherein A represents $CR^6$.

3. The compound according to claim 1, wherein A represents a nitrogen atom.

4. The compound according to claim 1, wherein $R^4$ represents a C1-C6 alkyl group optionally having one or more halogen atoms.

5. The compound according to claim 1, wherein $R^4$ represents an ethyl group.

6. The compound according to claim 1, wherein
   $R^1$ represents a C2-C10 haloalkyl group;
   $R^2$ and $R^3$ represent independently of each other a hydrogen atom, a C1-C3 alkyl group optionally having one or more halogen atoms, or a halogen atom;
   $R^4$ represents a C1-C6 alkyl group optionally having one or more halogen atoms;
   $R^5$ represents a C1-C6 alkyl group optionally having one or more halogen atoms; and
   p represents 0 or 1.

7. The compound according to claim 1, wherein
   $R^1$ represents a C2-C10 haloalkyl group;
   $R^2$ and $R^3$ represent each a hydrogen atom;
   $R^4$ represents a C1-C6 alkyl group optionally having one or more halogen atoms;
   $R^5$ represents a C1-C6 alkyl group optionally having one or more halogen atoms; and
   p represents 0 or 1.

8. The compound according to claim 1, wherein
   $R^1$ represents a C3-C6 alkyl having four or more fluorine atoms;
   $R^2$ and $R^3$ represent each a hydrogen atom;
   $R^4$ represents an ethyl group;
   $R^5$ represents a C1-C6 alkyl group optionally having one or more halogen atoms; and
   p represents 0 or 1.

9. A compound represented by formula (1-N):

(1-N)

wherein
   $Q^1$ represents a $N^+$—$O^-$ or a nitrogen atom,
   $Q^2$ represents a $N^+$—$O^-$, a $CR^{6N}$, or a nitrogen atom, wherein at least one of $Q^1$ and $Q^2$ represents an $N^+$—$O^-$;
   $R^{6N}$ represents a hydrogen atom, or a halogen atom;
   $R^{1N}$ represents a C2-C10 haloalkyl group;
   $R^{2N}$ and $R^{3N}$ represent independently of each other a hydrogen atom, a C1-C3 alkyl group optionally having one or more halogen atoms, or a halogen group;

$R^{4N}$ represents a C1-C6 alkyl group optionally having one or more halogen atoms;

$R^{5N}$ represents a C1-C6 alkyl group optionally having one or more halogen atoms; and q represents 0 or 1.

10. A composition for controlling a harmful arthropod, comprising the compound according to claim 1, and an inert carrier.

11. A method for controlling a harmful arthropod, comprising applying an effective amount of the compound according to claim 1 to a harmful arthropod or a habitat where a harmful arthropod lives.

12. A composition for controlling a harmful arthropod, comprising the compound according to claim 9, and an inert carrier.

13. A method for controlling a harmful arthropod, comprising applying an effective amount of the compound according to claim 9 to a harmful arthropod or a habitat where a harmful arthropod lives.

\* \* \* \* \*